United States Patent
Yoon et al.

(10) Patent No.: US 12,236,682 B2
(45) Date of Patent: Feb. 25, 2025

(54) METHOD FOR TRACKING SPORT PARTICIPANTS, DEVICE FOR TRACKING SPORT PARTICIPANTS, AND SYSTEM FOR TRACKING SPORT PARTICIPANTS

(71) Applicant: Fitogether Inc., Seoul (KR)

(72) Inventors: Jinsung Yoon, Seoul (KR); Jonghyun Lee, Seoul (KR)

(73) Assignee: Fitogether Inc., Seoul (KR)

( * ) Notice: Subject to any disclaimer, the term of this patent is extended or adjusted under 35 U.S.C. 154(b) by 0 days.

(21) Appl. No.: 18/341,679

(22) Filed: Jun. 26, 2023

(65) Prior Publication Data

US 2023/0334860 A1 Oct. 19, 2023

Related U.S. Application Data

(62) Division of application No. 17/131,148, filed on Dec. 22, 2020, now Pat. No. 11,688,166.

(30) Foreign Application Priority Data

Nov. 16, 2020 (KR) ........................ 10-2020-0153137
Nov. 16, 2020 (KR) ........................ 10-2020-0153138

(51) Int. Cl.
  *G06V 20/40* (2022.01)
  *A63B 24/00* (2006.01)
  (Continued)

(52) U.S. Cl.
  CPC .......... *G06V 20/42* (2022.01); *A63B 24/0062* (2013.01); *G06F 18/214* (2023.01);
  (Continued)

(58) Field of Classification Search
  None
  See application file for complete search history.

(56) References Cited

U.S. PATENT DOCUMENTS

| | | | |
|---|---|---|---|
| 2015/0116501 A1* | 4/2015 | McCoy | H04N 23/661 348/169 |
| 2016/0377698 A1* | 12/2016 | Nielsen | G06T 7/292 342/450 |

FOREIGN PATENT DOCUMENTS

| | | |
|---|---|---|
| JP | 2015089119 | 5/2015 |
| JP | 2017-531979 A | 10/2017 |

(Continued)

OTHER PUBLICATIONS

Feuerhake et al. "GPS-Aided Video Tracking." ISPRS International Journal of Geo-Information, 2015, 4(3), 1317-1335.
(Continued)

*Primary Examiner* — Leon Viet Q Nguyen
(74) *Attorney, Agent, or Firm* — BROADVIEW IP LAW, PC

(57) ABSTRACT

A multi-mode tracking method according to the present disclosure includes receiving, a sensor signal, obtaining a sensor-based location of a sports participant based on the sensor signal, obtaining a first credibility information related to a credibility of the sensor-based location, receiving a sports image captured at a camera disposed peripheral to a playfield, the sports image including the sports participant in the playfield, obtaining an image-based location of the sports participant, obtaining an second credibility information related to a credibility of the image-based location, wherein the credibility of the image-based location is related to an occlusion related to the sports participant, calculating an weight value based on the first credibility information and the second credibility information, calculating a location of the sports participant based on the weight value.

9 Claims, 22 Drawing Sheets

(51) Int. Cl.
  *G06F 18/214* (2023.01)
  *G06N 3/08* (2023.01)
  *G06V 10/25* (2022.01)
  *G06V 10/75* (2022.01)

(52) U.S. Cl.
  CPC ............... *G06N 3/08* (2013.01); *G06V 10/25* (2022.01); *G06V 10/751* (2022.01)

(56) References Cited

FOREIGN PATENT DOCUMENTS

| JP | 2020-13216 A | 1/2020 |
|---|---|---|
| KR | 10-2004-0041297 | 5/2004 |
| KR | 10-2015-0066941 A | 6/2015 |
| KR | 10-2017-0059266 A | 5/2017 |
| KR | 10-2020-0073229 | 6/2020 |

OTHER PUBLICATIONS

Notice of submission of opinion in Korean patent application No. 10-2020-0153137, mailed Mar. 25, 2022.

Tuan et al. "Visual-GPS Combined Drone Follow-Me Selfie Drone." Proceedings of the Korea Information Processing Society Conference, Nov. 2017, 134-137.

Notice of Allowance dated Jul. 19, 2022 in Korean Patent Application No. 10-2020-0153137.

Office Action dated Sep. 7, 2022 in Korean Patent Application No. 10-2020-0153138.

Tong et al. "A Best View Selection Method in Videos of Interested Player Captured by Multiple Cameras" Journal of KIISE, Dec. 2017, vol. 44, No. 12, pp. 1319-1332.

\* cited by examiner

1000

(a)　　　　　　　　(b)

(c)　　　　　　　　(d)

(a)

(b)

BB1

(a)

(b)

(c)

(d)

(a)          (b)          (c)          (d)

METHOD FOR TRACKING SPORT PARTICIPANTS, DEVICE FOR TRACKING SPORT PARTICIPANTS, AND SYSTEM FOR TRACKING SPORT PARTICIPANTS

CROSS-REFERENCE TO RELATED APPLICATION

This application is a Divisional Application of U.S. patent application Ser. No. 17/131,148 filed on Dec. 22, 2020, which claims priority to and the benefit of Korean Patent Application No. 10-2020-0153137 filed on Nov. 16, 2020, and Korean Patent Application No. 10-2020-0153138 filed on Nov. 16, 2020, the disclosure of which is incorporated herein by reference in its entirety.

BACKGROUND

1. Field of the Invention

The present disclosure is related to a player tracking method, a player tracking device, and a player tracking system capable of tracking players' locations.

2. Discussion of Related Art

With the improvement of image analysis technology and positioning technology, it has become possible to analyze the movements or motions of players during sport events, and thus sport analysis technology that quantifies the performance of sport players has recently attracted attention. When quantifying the performance of a sport player, the analysis of the player's location is considered as the most basic factor.

As a representative method of calculating a sport player's location, a method of calculating a position where a player is located in a stadium from an image captured by a camera and a method of using positioning instruments such as a Global Positioning System (GPS) device or a local positioning system (LPS) device are known.

However, a positioning method using a video has several limitations due to camera technology, including the inability to cope with a blockage situation in which a player to be tracked is hidden by other players in a video, and a positioning method using positioning instruments such as a GPS module has fundamental problems due to the decrease in positioning accuracy or the delay or reflection of signals which are caused by the locations of satellites, so each method has its limitations in situations where high precision is required.

SUMMARY OF THE INVENTION

The present disclosure is directed to providing a player tracking method, a player tracking device, and a player tracking system with improved accuracy of player location tracking.

A player tracking method according to the present disclosure may include receiving sensor signals from a plurality of positioning sensors located on a plurality of sport participants wherein the sensor signals each include a participant identifier and location data, receiving a sport image captured by a camera located near a playfield wherein the sport image includes at least a target participant among the plurality of sport participants on the playfield, detecting an occlusion related to the target participant in the sport image, determining the severity of the occlusion on the basis of sensor signals received from specific positioning sensors installed on specific sport players located in a region of interest related to the occlusion, determining a location of the sport participant on the basis of a pixel location related to the target participant in the sport image when it is not detected that the severity of the occlusion is greater than a threshold value, and determining a location of the sport participant on the basis of location data of a sensor signal having a participant identifier indicating the target participant when it is detected that the severity of the occlusion is greater than the threshold value.

A player tracking method according to the present disclosure may include acquiring image-based location data indicating a first location of a sport participant defined in a first coordinate system from a sport image which is captured by a camera located near a playfield and which includes sport participants on the playfield, wherein the image-based location data is acquired based on a pixel location related to the sport participant in the sport image, detecting an occlusion event related to the sport participant in the sport image, verifying the image-based location data on the basis of a result of the detection, acquiring a positioning sensor-based location indicating a second location of the sport participant defined in a second coordinate system on the basis of a sensor signal acquired from a positioning sensor located on the sport participant, acquiring a positioning sensor-based velocity indicating a velocity of the sport participant defined in the second coordinate system on the basis of the second location or the sensor signal, preparing a neural network for converting a location in the second coordinate system to the first coordinate system, wherein the neural network includes an input layer for receiving a location and a velocity corresponding to the second coordinate system, an output layer for outputting a result indicating a location value, and a hidden layer having a plurality of nodes connecting the input layer and the output layer, preparing a training set, wherein the training set includes image-based location data determined to be valid and positioning sensor-based location data and positioning sensor-based velocity data corresponding to the image-based location data determined to be valid; and training the neural network using the training set by inputting the positioning sensor-based location data and the positioning sensor-based velocity data of the training set to the input layer and adjusting weight values of the nodes on the basis of a difference between the location value of the result and the image-based location data corresponding to the input positioning sensor-based location data and positioning sensor-based velocity data.

A player tracking method according to the present disclosure may include receiving a sport image captured by a camera located near a playfield, wherein the sport image includes a sport participant on the playfield, receiving a sensor signal from a positioning sensor installed on the sport participant, detecting an occlusion event related to the sport participant in the sport image, determining a location of the sport participant on the basis of image-based location data indicating a location defined in a first coordinate system when the occlusion event is not detected, acquiring a positioning sensor-based location indicating a location defined in a second coordinate system on the basis of the sensor signal when the occlusion event is detected, acquiring a positioning sensor-based velocity indicating a velocity defined in the second coordinate system on the basis of the sensor signal or the positioning sensor-based location, and determining the location of the sport participant defined in the first coordinate system from the positioning sensor-based location and the positioning sensor-based velocity using a neural network for converting a location in the second coordinate system to the first coordinate system, wherein the neural network may include an input layer for receiving a location and a velocity according to the second coordinate system, an output layer for outputting a result indicating a location value corresponding to the first coordinate system, and a hidden layer having a plurality of nodes connecting the input layer and the output layer and may be trained by adjusting weight values of the plurality of nodes using a location and a velocity which correspond to the second coordinate system and which are labeled with the location corresponding to the first coordinate system.

A player tracking method according to the present disclosure may include receiving a sensor signal from a positioning sensor located on a sport participant, acquiring a positioning sensor-based location on the basis of the sensor signal, verifying the positioning sensor-based location on the basis of a change in the positioning sensor-based location compared to the previous positioning sensor-based location, determining a location of the sport participant on the basis of the positioning sensor-based location when the positioning sensor-based location is valid, acquiring a sport image captured by a camera located near a playfield when the positioning sensor-based location is invalid, wherein the sport image includes a sport participant on the playfield, predicting the validity of an image-based location acquired by projecting a pixel of the sport participant in the sport image onto a reference plane having the same height as the playfield, wherein the predicting includes at least one of detecting an occlusion related to the sport participant, detecting a vertical movement related to the sport participant, and computing a change in the image-based location compared to the previous image-based location, acquiring the image-based location on the basis of a pixel location of the sport participant in the sport image and determining the location of the sport participant on the basis of the image-based location when the image-based location is predicted to be valid, and determining the location of the sport participant on the basis of the positioning sensor-based location when the image-based location is predicted to be invalid.

A player tracking method according to the present disclosure may include receiving a sensor signal from a positioning sensor located on a sport participant, acquiring a positioning sensor-based location of the sport participant on the basis of the sensor signal, acquiring a sport image captured by a camera located near a playfield, wherein the sport image includes a sport participant on the playfield, acquiring an image-based location of the sport participant on the basis of a pixel location of the sport participant in the sport image, computing a disparity index between the positioning sensor-based location and the image-based location, wherein the disparity index is acquired from a difference between the positioning sensor-based location and the image-based location, determining a location of the sport participant on the basis of a first location, which is one of the positioning sensor-based location and the image-based location, when the disparity index is smaller than a predetermined first threshold value, acquiring a first reliability index related to one of the positioning sensor-based location and the image-based location when the disparity index is greater than a predetermined second threshold value, acquiring a second reliability index related to the other one of the positioning sensor-based location and the image-based location, determining the location of the sport participant on the basis of the first location when the first reliability index is greater than the second reliability index, and determining the location of the sport participant on the basis of a second location, which is the other one of the positioning sensor-based location and the image-based location when the first reliability index is smaller than the second reliability index.

A player tracking method according to the present disclosure may include receiving a sensor signal from a positioning sensor located on a sport participant, acquiring a positioning sensor-based location of the sport participant on the basis of the sensor signal, acquiring first reliability information related to reliability of the positioning sensor-based location, acquiring a sport image captured by a camera located near a playfield, wherein the sport image includes a sport participant on the playfield, acquiring an image-based location of the sport participant on the basis of a pixel location of the sport participant in the sport image, acquiring second reliability information related to reliability of the image-based location, wherein the reliability of the image-based location is related to at least one of an occlusion related to the sport participant, a vertical movement related to the sport participant, and a change in the image-based location compared to the previous image-based location, computing a weight value on the basis of the first reliability information and the second reliability information, wherein the weight value includes a sensor-based weight value and an image-based weight value, and computing a location of the sport participant, wherein the location of the sport participant is acquired from the positioning sensor-based location considering the sensor-based weight value and the image-based location considering the image-based weight value.

A player tracking method according to the present disclosure may include receiving a sensor signal from a positioning sensor located on a sport participant, acquiring a positioning sensor-based location of the sport participant on the basis of the sensor signal, preparing a reliability map corresponding to a playfield, wherein the reliability map includes a plurality of regions having reliability information including first reliability information related to reliability of the positioning sensor-based location, acquiring a sport image captured by a camera located near the playfield, wherein the sport image includes a sport participant on the playfield, acquiring an image-based location of the sport participant on the basis of a pixel location of the sport participant in the sport image, determining a specific region occupied by the sport participant on the basis of the positioning sensor-based location, determining a first weight value and a second weight value according to the first reliability information of the specific region; and determining a location of the sport participant on the basis of a weighted average of the positioning sensor-based location and the image-based location computed in consideration of the first weight value and the second weight value.

A player tracking method according to the present disclosure may include receiving a plurality of sport images from a plurality of cameras installed at different locations near a playfield, wherein each of the plurality of sport images includes the playfield and at least some sport participants, detecting a target participant in the plurality of sport images, selecting at least one candidate image from among the plurality of sport images according to a result of the detection of the target participant, detecting an occlusion related to the target participant in the at least one candidate image, selecting at least one valid image from the at least one candidate image according to a result of the detection of the occlusion, and determining a location of the target participant on the basis of a pixel location corresponding to the target participant in the at least one valid image.

A player tracking method according to the present disclosure may include receiving a plurality of sport images from a plurality of cameras installed at different locations near a playfield, wherein each of the plurality of sport images includes the playfield and at least some sport participants, detecting a target participant in the plurality of sport images, selecting at least one candidate image from among the plurality of sport images according to a result of the detection of the target participant, detecting an occlusion related to the target participant in the at least one candidate image, selecting at least one target image from the at least one candidate image according to a result of the detection of the occlusion, determining whether the sport participant hides another sport participant in the at least one candidate image or whether the sport participant is hidden by another sport participant in the at least one candidate image and selecting the target image from the at least one candidate image according to the determination when the occlusion is detected in all of the one or more candidate images, and determining a location of the target participant on the basis of a pixel location corresponding to the target participant in the at least one target image.

A player tracking method according to the present disclosure may include acquiring camera arrangement information including locations and orientations of a plurality of cameras located near a playfield, receiving sensor signals from a plurality of positioning sensors located on a plurality of sport participants, acquiring locations of the plurality of sport participants on the basis of the sensor signals, generating a virtual playfield including a plurality of fixed points corresponding to the plurality of cameras and a plurality of moving points corresponding to the plurality of sport participants, wherein locations of the plurality of fixed points in the virtual playfield are determined based on the camera arrangement information and locations of the plurality of moving points in the virtual playfield are determined based on the locations of the plurality of sport participants, computing a relationship between the plurality of sport participants and the plurality of cameras on the basis of a relative location between the plurality of fixed points and the plurality of moving points, predicting an occlusion of the plurality of sport participants by the plurality of cameras on the basis of relative locations between the plurality of moving points and angles between a plurality of virtual lines extending from the plurality of fixed points to the plurality of moving points, and generating a matching table between the sport participant and the plurality of cameras on the basis of the occlusion prediction and the relationship.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
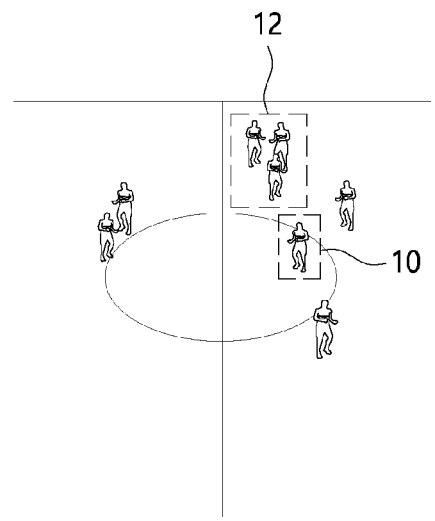
FIG. 1 is a diagram illustrating an exemplary conventional positioning method.

The above objects, features, and advantages of the present disclosure will become more apparent from the following detailed description taken in conjunction with the accompanying drawings. However, since the present disclosure may be variously modified and have several exemplary embodiments, specific exemplary embodiments will be shown in the accompanying drawings and described in detail.

Like reference numerals refer to like elements throughout the specification. Further, like reference numerals will be used to designate like elements within the same scope shown in the drawings of the embodiments, and a relevant description thereof will be omitted.

Detailed descriptions about well-known functions or configurations associated with the present disclosure will be omitted in order not to unnecessarily obscure the subject matter of the present disclosure. It should also be noted that, even though ordinal numbers (such as first and second) are used in the following description, they are used only to distinguish similar elements.

The suffixes "module" and "unit" for elements used in the following embodiments are given or used interchangeably only for facilitation of preparing this specification, and thus they are not assigned a specific meaning or function.

As used herein, the singular forms "a," "an," and "one" are intended to include the plural forms as well, unless the context clearly indicates otherwise.

It should be further understood that the terms "comprises" and/or "comprising" used herein specify the presence of stated features or components, but do not preclude the presence or addition of one or more other features or components.

Additionally, the sizes of components depicted in the drawings may be exaggerated or reduced for convenience of description. For example, since the sizes and thicknesses of components in the drawings are arbitrarily illustrated for convenience of description, the following embodiments are not limited thereto.

When a certain embodiment may be implemented differently, a specific process order may be performed differently from the described order. For example, two consecutively described processes may be performed substantially at the same time or performed in the order opposite to the described order.

In the following embodiments, when elements are connected to each other, the elements are connected to each other not only directly but also indirectly with other elements interposed therebetween.

For example, in the following embodiments, when elements are electrically connected to each other, the elements are electrically connected to each other not only directly but also indirectly with other elements interposed therebetween.

A player tracking method according to the present disclosure may include receiving sensor signals from a plurality of positioning sensors located on a plurality of sport participants wherein the sensor signals each include a participant identifier and location data, receiving a sport image captured by a camera located near a playfield wherein the sport image includes at least a target participant among the plurality of sport participants on the playfield, detecting an occlusion related to the target participant in the sport image, determining the severity of the occlusion on the basis of sensor signals received from specific positioning sensors installed on specific sport players located in a region of interest related to the occlusion, determining a location of the sport participant on the basis of a pixel location related to the target participant in the sport image when it is not determined that the severity of the occlusion is greater than a threshold value, and determining a location of the sport participant on the basis of location data of a sensor signal having a participant identifier indicating the target participant when it is determined that the severity of the occlusion is greater than the threshold value.

The region of interest may be a predetermined region for the target participant associated with the occlusion, and the determining of the severity may include determining the severity of the occlusion on the basis of the number of sensor signals located in the region of interest.

The determining of the severity may include assigning a value indicating a severe occlusion for the severity when the number of sensor signals is greater than the threshold value and assigning a value indicating a mild occlusion for the severity when the number of sensor signals is smaller than the threshold value.

The determining of the severity may further include acquiring team information indicating whether the target participant is on the same team as at least one sport participant different from the target participant on the basis of a participant identifier corresponding to the target participant and the sport participant, and the sport participant may hide or be hidden by the target participant.

The determining of the severity may include assigning the value indicating the severe occlusion for the severity when the target participant and the sport participant are on the same team and assigning the value indicating the mild occlusion for the severity when the target participant and the sport participant are on different teams.

The team information may be acquired from pixel data corresponding to the target participant and the sport participant in the sport image.

A player tracking method according to the present disclosure may include acquiring image-based location data indicating a first location of a sport participant defined in a first coordinate system from a sport image which is captured by a camera located near a playfield and which includes sport participants on the playfield, wherein the image-based location data is acquired based on a pixel location related to the sport participant in the sport image, detecting an occlusion event related to the sport participant in the sport image, verifying the image-based location data on the basis of a result of the detection, acquiring a positioning sensor-based location indicating a second location of the sport participant defined in a second coordinate system on the basis of a sensor signal acquired from a positioning sensor located on the sport participant, acquiring a positioning sensor-based velocity indicating a velocity of the sport participant defined in the second coordinate system on the basis of the second location or the sensor signal, preparing a neural network for converting a location in the second coordinate system to the first coordinate system, wherein the neural network includes an input layer for receiving a location and a velocity corresponding to the second coordinate system, an output layer for outputting a result indicating a location value, and a hidden layer having a plurality of nodes connecting the input layer and the output layer, preparing a training set, wherein the training set includes image-based location data determined to be valid and positioning sensor-based velocity data and positioning sensor-based location data corresponding to the image-based location data determined to be valid; and training the neural network using the training set by inputting the positioning sensor-based location data and positioning sensor-based velocity data of the training set to the input layer and adjusting weight values of the nodes on the basis of a difference between the location value of the result and the image-based location data corresponding to the input positioning sensor-based location data and positioning sensor-based velocity data.

The verifying may include determining that the image-based location data is valid when the occlusion event is not detected and determining that the image-based location data is invalid when the occlusion event is detected.

The occlusion event may indicate that the number of sensor signals of at least one sport participant in a region of interest related to the occlusion is greater than a threshold value, and the region of interest may be a predetermined region for a region where the occlusion has occurred.

A player tracking method according to the present disclosure may include receiving a sport image captured by a camera located near a playfield, wherein the sport image includes a sport participant on the playfield, receiving a sensor signal from a positioning sensor installed on the sport participant, detecting an occlusion event related to the sport participant in the sport image, determining a location of the sport participant on the basis of image-based location data indicating a location defined in a first coordinate system when the occlusion event is not detected, acquiring a positioning sensor-based location indicating a location defined in a second coordinate system on the basis of the sensor signal when the occlusion event is detected, acquiring a positioning sensor-based velocity indicating a velocity defined in the second coordinate system on the basis of the sensor signal or the positioning sensor-based location, and determining the location of the sport participant defined in the first coordinate system from the positioning sensor-based location and the positioning sensor-based velocity using a neural network for converting the location in the second coordinate system to the first coordinate system, wherein the neural network may include an input layer for receiving a location and a velocity according to the second coordinate system, an output layer for outputting a result indicating a location value corresponding to the first coordinate system, and a hidden layer having a plurality of nodes connecting the input layer and the output layer and may be trained by adjusting weight values of the plurality of nodes using a location and a velocity which correspond to the second coordinate system and which are labeled with the location corresponding to the first coordinate system.

A player tracking method according to the present disclosure may include receiving a sensor signal from a positioning sensor located on a sport participant, acquiring a positioning sensor-based location on the basis of the sensor signal, verifying the positioning sensor-based location on the basis of a change in the positioning sensor-based location compared to the previous positioning sensor-based location, determining a location of the sport participant on the basis of the positioning sensor-based location when the positioning sensor-based location is valid, acquiring a sport image captured by a camera located near a playfield when the positioning sensor-based location is invalid, wherein the sport image includes a sport participant on the playfield, predicting the validity of an image-based location acquired by projecting a pixel of the sport participant in the sport image onto a reference plane having the same height as the playfield, wherein the predicting includes at least one of detecting an occlusion related to the sport participant, detecting a vertical movement related to the sport participant, and computing a change in the image-based location compared to the previous image-based location, acquiring the image-based location on the basis of a pixel location of the sport participant in the sport image and determining the location of the sport participant on the basis of the image-based location when the image-based location is predicted to be valid, and determining the location of the sport participant on the basis of the positioning sensor-based location when the image-based location is predicted to be invalid.

The verifying of the sensor-based location may include determining that the sensor-based location is invalid when the change in the positioning sensor-based location compared to the previous positioning sensor-based location is greater than a predetermined threshold value and determining that the sensor-based location is valid when the change in the positioning sensor-based location compared to the previous positioning sensor-based location is smaller than a predetermined threshold value.

The verifying of the positioning sensor-based location may include further considering sensor signal reliability-related information included in the sensor signal.

The sensor signal reliability-related information included in the sensor signal may include at least one of a degree of polarization (DoP) and a signal-to-noise ratio (SNR).

The vertical movement related to the sport participant may be detected based on a movement of the sport participant in a direction perpendicular to the reference plane acquired from an inertial sensor worn by the sport participant.

A player tracking method according to the present disclosure may include receiving a sensor signal from a positioning sensor located on a sport participant, acquiring a positioning sensor-based location of the sport participant on the basis of the sensor signal, acquiring a sport image captured by a camera located near a playfield, wherein the sport image includes a sport participant on the playfield, acquiring an image-based location of the sport participant on the basis of a pixel location of the sport participant in the sport image, computing a disparity index between the positioning sensor-based location and the image-based location, wherein the disparity index is acquired from a difference between the positioning sensor-based location and the image-based location, determining a location of the sport participant on the basis of a first location, which is one of the positioning sensor-based location and the image-based location, when the disparity index is smaller than a predetermined first threshold value, acquiring a first reliability index related to one of the positioning sensor-based location and the image-based location when the disparity index is greater than a predetermined second threshold value, acquiring a second reliability index related to the other one of the positioning sensor-based location and the image-based location, determining the location of the sport participant on the basis of the first location when the first reliability index is greater than the second reliability index, and determining the location of the sport participant on the basis of a second location, which is the other one of the positioning sensor-based location and the image-based location when the first reliability index is smaller than the second reliability index.

A player tracking method according to the present disclosure may include receiving a sensor signal from a positioning sensor located on a sport participant, acquiring a positioning sensor-based location of the sport participant on the basis of the sensor signal, acquiring first reliability information related to the reliability of the positioning sensor-based location, acquiring a sport image captured by a camera located near a playfield, wherein the sport image includes a sport participant on the playfield, acquiring an image-based location of the sport participant on the basis of a pixel location of the sport participant in the sport image, acquiring second reliability information related to the reliability of the image-based location, wherein the reliability of the image-based location is related to at least one of an occlusion related to the sport participant, a vertical movement related to the sport participant, and a change in the image-based location compared to the previous image-based location, computing a weight value on the basis of the first reliability information and the second reliability information, wherein the weight value includes a sensor-based weight value and an image-based weight value, and computing a location of the sport participant, wherein the location of the sport participant is acquired from the positioning sensor-based location considering the sensor-based weight value and the image-based location considering the image-based weight value.

A player tracking method according to the present disclosure may include receiving a sensor signal from a positioning sensor located on a sport participant, acquiring a positioning sensor-based location of the sport participant on the basis of the sensor signal, acquiring first reliability information related to the reliability of the positioning sensor-based location, acquiring a sport image captured by a camera located near a playfield, wherein the sport image includes a sport participant on the playfield, acquiring an image-based location of the sport participant on the basis of a pixel location of the sport participant in the sport image, acquiring second reliability information related to the reliability of the image-based location, wherein the reliability of the image-based location is related to at least one of an occlusion related to the sport participant, a vertical movement related to the sport participant, and a change in the image-based location compared to the previous image-based location, computing an weight value on the basis of the first reliability information and the second reliability information, wherein the weight value includes a sensor-based weight value and an image-based weight value, and computing a location of the sport participant, wherein the location of the sport participant is acquired from the positioning sensor-based location considering the sensor-based weight value and the image-based location considering the image-based weight value.

The reliability of the positioning sensor-based location may be related to at least one of the computed change in the positioning sensor-based location compared to the previous positioning sensor-based location and the sensor signal reliability-related information included in the sensor signal.

The vertical movement related to the sport participant may be detected based on a movement of the sport participant which is in a direction perpendicular to the reference plane with the same height as the playfield and which is acquired from an inertial sensor worn by the sport participant.

The reliability of the positioning sensor-based location and the reliability of the image-based location may be related to a disparity index between the positioning sensor-based location and the image-based location, and the disparity index may be acquired from a difference between the positioning sensor-based location and the image-based location.

A player tracking method according to the present disclosure may include receiving a sensor signal from a positioning sensor located on a sport participant, acquiring a positioning sensor-based location of the sport participant on the basis of the sensor signal, preparing a reliability map corresponding to a playfield, wherein the reliability map includes a plurality of regions having reliability information including first reliability information related to the reliability of the positioning sensor-based location, acquiring a sport image captured by a camera located near the playfield, wherein the sport image includes a sport participant on the playfield, acquiring an image-based location of the sport participant on the basis of a pixel location of the sport participant in the sport image, determining a specific region occupied by the sport participant on the basis of the positioning sensor-based location; determining a first weight value and a second weight value according to the first reliability information of the specific region; and determining a location of the sport participant on the basis of a weighted average of the positioning sensor-based location and the image-based location computed in consideration of the first weight value and the second weight value.

The first reliability information related to the reliability of the positioning sensor-based location may be related to at least one of the computed change in the positioning sensor-based location compared to the previous positioning sensor-based location and the sensor signal reliability-related information included in the sensor signal.

The reliability map may include a plurality of regions having reliability information including second reliability information related to the reliability of the image-based location.

The second reliability information related to the reliability of the image-based location may be related to at least one of a detected occlusion related to the sport participant, a detected vertical movement related to the sport participant, and a computed change in the image-based location compared to the previous image-based location.

The first weight value and the second weight value may be determined according to the second reliability information of the specific region.

A player tracking method according to the present disclosure may include receiving a plurality of sport images from a plurality of cameras installed at different locations near a playfield, wherein each of the plurality of sport images includes the playfield and at least some sport participants, detecting a target participant in the plurality of sport images, selecting at least one candidate image from among the plurality of sport images according to a result of the detection of the target participant, detecting an occlusion related to the target participant in the at least one candidate image, selecting at least one valid image from the at least one candidate image according to a result of the detection of the occlusion, and determining a location of the target participant on the basis of a pixel location corresponding to the target participant in the at least one valid image.

When the at least one valid image includes a first valid image and a second valid image, the determining of the location of the target participant may include acquiring a first location of the target participant on the basis of a pixel location corresponding to the target participant in the first valid image, acquiring a second location of the target participant on the basis of a pixel location corresponding to the target participant in the second valid image, and computing a location of the target participant on the basis of both of the first location and the second location.

The determining of the location of the target participant may include selecting a single image from the at least one valid image on the basis of a first condition related to a relative location between the target participant and a camera that captures the at least one valid image and a second condition related to a lens distortion parameter of the camera that captures the at least one valid image and computing a location of the target participant on the basis of the single image.

A player tracking method according to the present disclosure may include receiving a plurality of sport images from a plurality of cameras installed at different locations near a playfield, wherein each of the plurality of sport images includes the playfield and at least some sport participants, detecting a target participant in the plurality of sport images, selecting at least one candidate image from among the plurality of sport images according to a result of the detection of the target participant, detecting an occlusion related to the target participant in the at least one candidate image, selecting at least one target image from the at least one candidate image according to a result of the detection of the occlusion, determining whether the sport participant hides or is hidden by another sport participant in the at least one candidate image and selecting the target image from the at least one candidate image according to the determination when the occlusion is detected in all of the one or more candidate images, and determining a location of the target participant on the basis of a pixel location corresponding to the target participant in the at least one target image.

The at least one target image may be selected from among the at least one candidate image in which the sport participant hides the other sport participant in the at least one candidate image.

When the at least one target image includes a first target image and a second target image, the determining of the location of the target participant may include acquiring a first location of the target participant on the basis of a pixel location corresponding to the target participant in the first target image, acquiring a second location of the target participant on the basis of a pixel location corresponding to the target participant in the second target image, and computing a location of the target participant on the basis of both of the first location and the second location.

The determining of the location of the target participant may include selecting a single image from the at least one target image on the basis of a first condition related to a relative location between the target participant and a camera that captures the at least one target image and a second condition related to a lens distortion parameter of the camera that captures the at least one target image and computing a location of the target participant on the basis of the single image.

A player tracking method according to the present disclosure may include acquiring camera arrangement information including locations and orientations of a plurality of cameras located near a playfield, receiving sensor signals from a plurality of positioning sensors located on a plurality of sport participants, acquiring locations of the plurality of sport participants on the basis of the sensor signals, generating a virtual playfield including a plurality of fixed points corresponding to the plurality of cameras and a plurality of moving points corresponding to the plurality of sport participants, wherein locations of the plurality of fixed points on the virtual playfield are determined based on the camera arrangement information and locations of the plurality of moving points on the virtual playfield are determined based on the locations of the plurality of sport participants, computing a relationship between the plurality of sport participants and the plurality of cameras on the basis of a relative location between the plurality of fixed points and the plurality of moving points, predicting an occlusion of the plurality of sport participants by the plurality of cameras on the basis of relative locations between the plurality of moving points and angles between a plurality of virtual lines extending from the plurality of fixed points to the plurality of moving points, and generating a matching table between the sport participant and the plurality of cameras on the basis of the occlusion prediction and the relationship.

The following description will refer to FIG. 1. FIG. 1 is a diagram showing an exemplary conventional positioning method. Specifically, FIG. 1 shows a specific situation of a positioning method that computes a point where a player is located for an image captured through a camera.

According to a video-based positioning method, only when a player to be tracked is recognized in a video can the player's location be accurately computed.

For example, a player located in a first region 10 of FIG. 1 may be recognized, and thus the player's location can be computed for tracking.

However, a player located in a second region 12 of FIG. 1 may be difficult to recognize because an occlusion event occurs. Specifically, since a plurality of players are concentrated in the second region 12, an occlusion in which a player to be tracked is covered by another player in a video may occur. Therefore, the location of the player to be tracked may not be accurately acquired because the player is hidden by another player.

In other words, the video-based positioning method may not be able to cope with the occlusion situation in which a player to be tracked is hidden by another player in a video.

Figure 2:
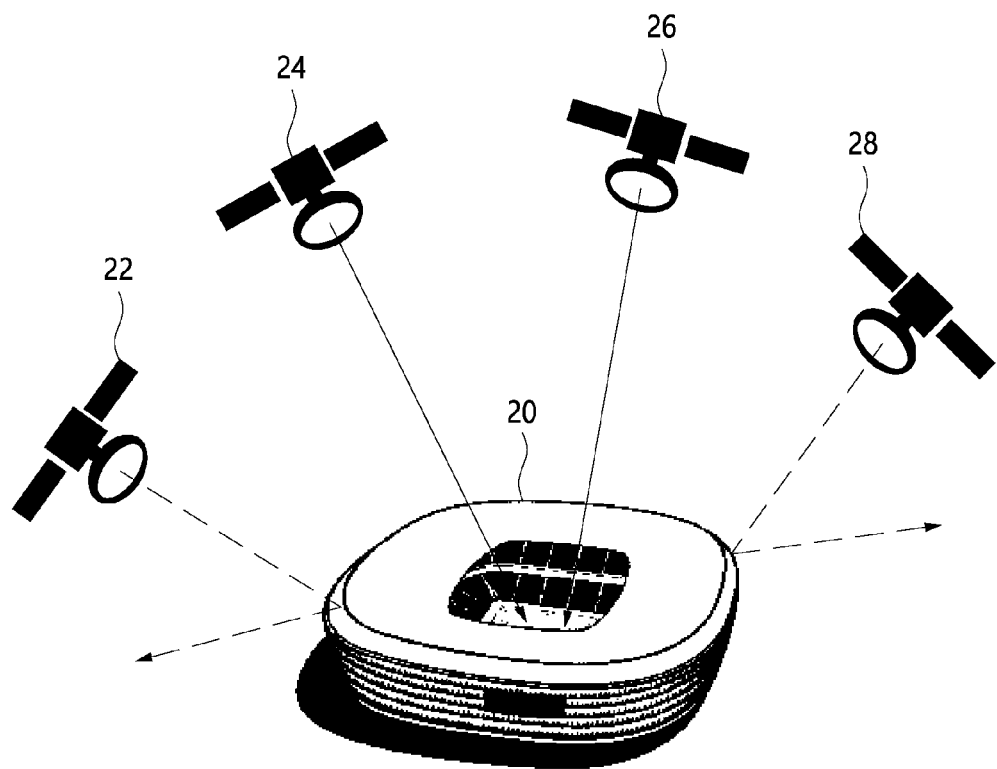
FIG. 2 is a diagram illustrating another exemplary conventional positioning method.

The following description will refer to FIG. 2. FIG. 2 is a diagram illustrating another exemplary conventional positioning method. Specifically, FIG. 2 is a diagram showing a positioning method that computes a point where a player is located using positioning instruments such as a GPS module.

Specifically, a GPS module-based positioning method computes a location of a player to be tracked depending on a signal transmitted from a satellite. However, signals transmitted from satellites may be greatly affected by structures around the player to be tracked.

For example, GPS signals transmitted from some satellites 24 and 26 of FIG. 2 may be transmitted to the inside of a stadium without being affected by the structures around the player to be tracked. However, GPS signals transmitted from some satellites 22 and 28 of FIG. 2 may not be able to reach the inside of the stadium due to the influence of the structures around the player to be tracked. At this time, when the GPS signals transmitted from some satellites 22 and 28 are affected by the surrounding structures, there may be an error in the player's location computed from the GPS signals.

Also, since the degree to which a GPS signal is affected by surrounding structures is different for each region of a playfield in the stadium, the GPS module-based positioning method has a problem in that reliability is different for each region of the playfield in the stadium.

Herein, a player tracking device, a player tracking system, and a player tracking method for overcoming the limitations of the positioning method using videos or the positioning method using positioning instruments such as a GPS module or a local positioning system (LPS) module will be described.

The player tracking device, the player tracking system, and the player tracking method of the present disclosure will be described below. Here, player tracking may be performed using positioning sensor data obtained from a positioning sensor mounted on a player or image data acquired through at least one camera. The present disclosure discloses a technique of fusing the above-described data or a technique of using multiple pieces of image data in order to improve the accuracy of the player's location calculated from such basic data.

The player tracking method, the player tracking device, and the player tracking system according to an embodiment of the present disclosure will be described below.

Player tracking according to this embodiment may be performed using both image data and positioning sensor data. Player tracking using image data may compute a player's location on the basis of pixel data related to the player's location in image data, and player tracking using positioning sensor data may compute a player's location on the basis of data such as latitude and longitude related to the player's location included in the positioning sensor data. In this case, when the player tracking using the image data is incorrect, the player tracking may be supplemented by the positioning sensor data. When the player tracking using the positioning sensor data is incorrect, the player tracking may be supplemented by the image data.

Figure 3:
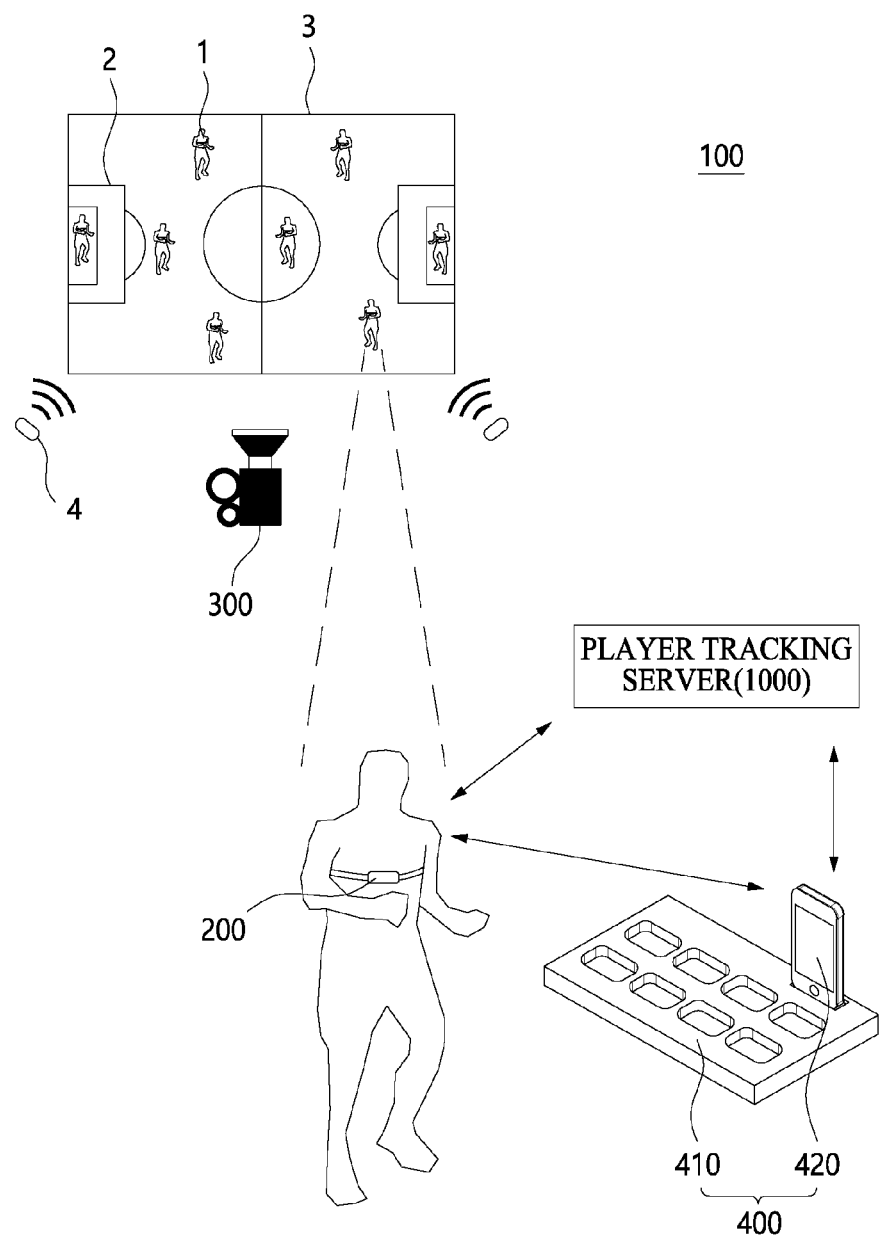
FIG. 3 is a schematic diagram illustrating a player tracking system according to an embodiment of the present disclosure.

FIG. 3 is a schematic diagram illustrating the player tracking device, the player tracking system, and the player tracking method according to an embodiment of the present disclosure.

Referring to FIG. 3, the player tracking device, the player tracking system, and the player tracking method according to this embodiment may include tracking a player's location using both image data and positioning sensor data.

A player tracking system 100 according to an embodiment of the present disclosure will be described below with reference to FIG. 3.

Referring to FIG. 3, the player tracking system 100 may include a positioning sensor device 200, an image capture device 300, an intermediate server 400, and a player tracking device 1000.

The positioning sensor device 200 of the player tracking system 100 may be a positioning instrument such as a GPS module and an LPS module.

As an example, the positioning sensor device 200 may be a GPS module 210, and the GPS module may receive radio waves transmitted from a satellite in association with the Global Navigation System (GNSS) and transmit data on the location of the positioning sensor device 200 to the player tracking device 1000.

As another example, the positioning sensor device 200 may be an LPS module 220, and the LPS module may receive radio waves transmitted from a beacon 4 in association with an LPS and transmit data regarding the location of the positioning sensor device 200. The beacon 4 may be placed in the vicinity of the playfield and in various locations.

The image capture device 300 of the player tracking system 100 may be a camera having any suitable form and function. The image capture device 300 may transmit image data acquired by capturing a sport participant 1, a playfield line 2, and a playfield 3 to the player tracking device 1000.

The player tracking device 1000 of the player tracking system 100 may acquire image data and positioning sensor data. Also, the player tracking device 1000 may acquire an image-based location from the image data and may acquire a positioning sensor-based location from the positioning sensor data. Also, the player tracking device 1000 may determine the validity of the image-based location and the positioning sensor-based location and may determine a location of a sport participant with high accuracy.

The player tracking device 1000 may be implemented as a server device of any suitable type. Hereinafter, the player tracking device 1000 is referred to as the player tracking server 1000. However, this is just for convenience of description, and the player tracking device 1000 is not necessarily implemented in the form of a server.

Meanwhile, the player tracking system 100 may further include an intermediate server 400 or a repeater. In other words, the player tracking server 1000 of the player tracking system 100 may be provided in a single form or may be provided in a separate form rather than in the single form.

In this case, data transmitted from the positioning sensor device 200 and the image capture device 300 may be transmitted directly to the player tracking server 1000 and may also be transmitted indirectly to the player tracking server 1000 via the intermediate server 400. When data is transmitted via the intermediate server 400, the data may be transferred to a portable electronic device 420 through a docking station 410. Also, the data may be transferred from the portable electronic device 420 to the player tracking server 1000 using any appropriate communication method.

The player tracking server 1000 according to an embodiment of the present disclosure will be described below.

According to an embodiment of the present disclosure, the player tracking server 1000 may acquire image data from the image capture device 300 in order to determine a location of a sport participant. Also, the player tracking server 1000 may acquire positioning sensor data from a positioning sensor device in order to determine a location of a sport participant. Also, the player tracking server 1000 may compute an image-based location from the acquired image data. Also, the player tracking server 1000 may compute a positioning sensor-based location from the acquired positioning sensor data. Also, the player tracking server 1000 may determine the location of the sport participant on the basis of the computed image-based location and positioning sensor-based location.

Figure 4:
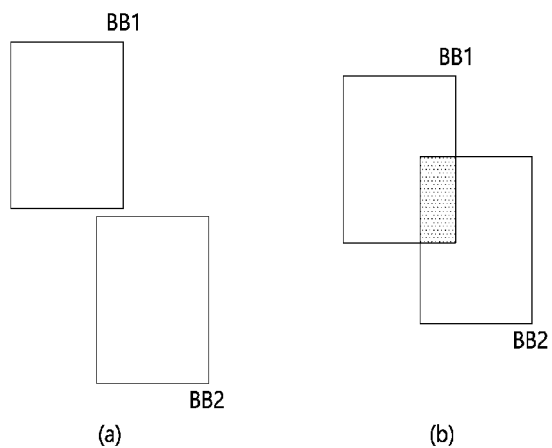
FIG. 4 is a block diagram of a player tracking server 1000 according to the present disclosure.

The following description will refer to FIG. 4. FIG. 4 is a block diagram of the player tracking server 1000 according to an embodiment of the present disclosure.

Referring to FIG. 4, the player tracking server 1000 may include a communication module 1100, a memory 1200, and a controller 1300.

Components of the player tracking server 1000 according to an embodiment of the present disclosure will be described below.

The communication module 1100 may communicate with an external apparatus. The player tracking server 1000 may transmit or receive data to or from an external server including the image capture device 300, the positioning sensor device 200, or the intermediate server 400 through the communication module 1100.

For example, the player tracking server 1000 may receive image data acquired from the image capture device 300 or positioning sensor data acquired from the positioning sensor device 200 through the communication module 1100. As another example, the player tracking server 1000 may access the Internet through the communication module 1100 to upload the image data or the positioning sensor data.

The communication module 1100 is largely divided into a wired-type module and a wireless-type module. Since the wired-type module and the wireless-type module each have advantages and disadvantages, in some cases, the player tracking server 1000 may be provided with both of the wired-type module and the wireless-type module.

Here, the wired-type module may use, for example, local area network (LAN) or universal serial bus (USB) communication or other schemes.

Also, here, the wireless-type module may mainly use a wireless personal area network (WPAN)-based communication scheme such as Bluetooth or Zigbee. However, since a wireless communication protocol is not limited thereto, the wireless-type communication module may use a wireless local area network (WLAN)-based communication scheme such as Wi-Fi or other known communication schemes.

The memory 1200 may store various kinds of information. Various kinds of data may be temporarily or semi-permanently stored in the memory 1200. Examples of the memory 1200 may include a hard disk drive (HDD), a solid-state drive (SSD), a flash memory, a read-only memory (ROM), a random access memory (RAM), etc.

The memory 1200 may be built into, or detachable from, the player tracking server 1000. Various kinds of data needed for the operation of the player tracking server 1000, in addition to an operating system (OS) for driving the player tracking server 1000 or a program for operating the components of the player tracking server 1000, may be stored in the memory 1200. For example, image data acquired in the form of an intensity map and an RGB map from the image capture device 300 and positioning sensor data acquired from the positioning sensor device 200 may be stored in the memory 1200.

The controller 1300 may control the overall operation of the player tracking server 1000. For example, the controller 1300 may load a program for the operating of the player tracking server 1000 from the memory 1200 and execute the program.

The controller 1300 may be implemented as a central processing unit (CPU) or the like with hardware, software, or a combination thereof. The controller 1300 may be provided in the form of an electronic circuit for processing an electrical signal to perform a control function when implemented with hardware and may be provided in the form of a program or code for driving a hardware circuit when implemented with software.

Some operations performed by an example of the player tracking system 100 in association with the player tracking method will be described in detail below.

The player tracking system 100 according to an embodiment of the present disclosure may acquire image data and positioning sensor data.

The player tracking server 1000 may acquire image data and positioning sensor data. Specifically, the player tracking server 1000 may acquire image data from the image capture device 300 through the communication module 1100. Also, the player tracking server 1000 may acquire information related to the image capture device 300 from the image capture device 300 through the communication module 1100. Also, the player tracking server 1000 may acquire positioning sensor data from the positioning sensor device 200 through the communication module 1100.

The image data may include pixel information related to a plurality of sport participants, playfield lines, playfield points, a ball, and the like of a sport game and sport game progress information (elapsed time, image data capture time, and the like).

The information related to the image capture device 300 may include arrangement information related to the orientation and location of a camera. Alternatively, among the information related to the image capture device 300, the arrangement information related to the location of the camera may be acquired by the player tracking server 1000 with any appropriate method.

The positioning sensor data may include location-related data of a positioning sensor device and reliability-related data of a sensor signal.

The player tracking system 100 according to an embodiment of the present disclosure may resample the image data or remove noise.

Specifically, the player tracking server 1000 may be controlled to perform an operation of resampling the image data. Specifically, the player tracking server 1000 may perform an operation of resampling the image data at a specific frame rate. Through the resampling operation of the player tracking server 1000, the player tracking server 1000 may adjust time synchronization with positioning sensor data, which will be described below. The specific frame rate may be any suitable frame rate (e.g., 10 frames).

Also, the player tracking server 1000 may be controlled to perform an operation of removing noise from the image data. Specifically, image data captured by the image capture device may have distortion. For example, the image data may have distortion caused by lens distortion or have distortion caused by the orientation (angle) of a camera or a distance from a camera. Therefore, the player tracking server 1000 may perform an operation of correcting the above-described distortions of the image data.

The player tracking system 100 according to an embodiment of the present disclosure may perform an operation of correlating the image data with the positioning sensor data. Specifically, the player tracking system 100 may adjust time synchronization with the image data and the positioning sensor data.

Specifically, the controller 1300 of the player tracking server 1000 may be provided to correlate the image data with the positioning sensor data using time variables. In other words, the controller 1300 of the player tracking server 1000 may be implemented to adjust time synchronization between the image data and the positioning sensor data.

As an example, the time synchronization between the image data and the positioning sensor data may be adjusted based on a specific time point of the sport game.

In this case, the specific time point of the sport game may be a characteristic time point of the sport game. For example, the specific time point of the sport game may be a start time point of the game.

Also, when there is a break time in the sport game, the specific time point of the sport game may be a restart time point of the sport game. As an example, in the case of a soccer game, there is a half time between the first half and the second half, and in this case, the time synchronization between the image data and the positioning sensor data may be adjusted based on the start time of the first half and the start time of the second half. At the start time point of the first half and the start time point of the second half, some or more sport participants may start to move, and the velocity of the sport participants may change accordingly. Therefore, the time synchronization between the image data and the positioning sensor data may be adjusted in consideration of the change in locations or velocitys of the sport participants at the start time of the first half and the start time of the second half.

For example, the time synchronization between the image data and the positioning sensor data may be adjusted based on a time point at which the velocity data of at least one sport participant acquired or calculated from the image data matches the velocity data of at least one sport participant acquired or calculated from the positioning sensor data.

In this case, the number of sport participants subject to a comparison between the velocity data from the image data and the velocity data from the positioning sensor data may be any appropriate number. In other words, the adjustment of the time synchronization through the above-described comparison of the velocity data may be performed for all or some of the sport participants.

As an example, the time synchronization between the image data and the positioning sensor data may be adjusted in consideration of a time point at which the velocity change acquired from the positioning sensor data is detected. As a specific example, most of the sport participants start to move a predetermined time after the start point of the first half or the second half, and thus the velocitys of the sport participants may change. The positioning sensor device may acquire data related to the change in locations of the sport participants and may detect a time point at which the velocity change acquired from the data related to the location change is started. According to an example, the time synchronization between the image data and the positioning sensor data may be adjusted based on a time point before a specific time point (e.g., more than 0 seconds to less than 2 seconds) based on the time point at which the velocity change is detected.

In this case, in association with the start time point of the velocity change, when changes in velocity of a predetermined threshold number or more of sport participants are detected, a time point at which the changes are detected may be determined as a start time point of the velocity changes.

Also, any suitable calculation method such as the Wasserstein distance calculation method may be used to adjust the time synchronization.

Also, for accuracy, the time synchronization between the image data and the positioning sensor data needs to be adjusted not only at the start time point of the game but also during the game.

According to an embodiment of the present disclosure, the time synchronization between the image data and the positioning sensor data may be adjusted based on time points corresponding to a positional relationship between a plurality of sport participants acquired from the image data at an arbitrary time point during the game and a positional relationship between a plurality of sport participants acquired from the positioning sensor data.

As an example, the positioning sensor data may include an identifier of each of the sport participants, and location data of at least one sport participant identified using the identifier may be acquired from the positioning sensor data.

Also, the at least one identified sport participant of the positioning sensor data may be distinguishable or identifiable in the image data, and the location data of the at least one identified sport participant may be acquired from the image data.

In this case, a connective relationship between sport participants may be acquired based on the location data of the at least one sport participant acquired from the positioning sensor data, and also a connective relationship between sport participants may be acquired based on the location data of the at least one sport participant acquired from the image data. In this case, the time synchronization between the image data and the positioning sensor data may be adjusted based on a time point at which the connective relationship between the sport participants acquired from the positioning sensor data and the connective relationship between the sport participants acquired from the image data match each other exactly or within an error range. For example, the connective relationship between the sport participants may be expressed as a line or plane connecting the pieces of location data of the sport participants acquired from the image data or the positioning sensor data.

When the connective relationships between the sport participants are expressed as lines, the time synchronization between the image data and the positioning sensor data may be adjusted in consideration of whether the lengths or directions of the lines match each other.

When the connective relationships between the sport participants are expressed as planes, the time synchronization between the image data and the positioning sensor data may be adjusted in consideration of whether the shapes of figures consisting of the outlines of the planes match each other.

The player tracking system 100 according to an embodiment of the present disclosure may perform appropriate data processing such as noise removal, amplification, and filtering on positioning sensor data acquired from the positioning sensor device 200. Specifically, the player tracking server 1000 may be provided to process the above-described data processing.

The player tracking system 100 according to an embodiment of the present disclosure may change the format of image data. Specifically, the player tracking server 1000 may convert the format of image data received from the image capture device 300 from an RGB map to an intensity map. In this case, data related to the RGB map may be stored in the memory 1200 of the player tracking server 1000. Data related to the RGB map of the image data stored in the memory 1200 of the player tracking server 1000 may be used by the player tracking server 1000, which will be described below, to detect an occlusion event between players or determine the severity of an occlusion event. By changing the format of image data, image data may be basically tracked in the form of an intensity map, but data included in an RGB map may be used only when necessary. Thus, it is possible to reduce the amount of computation of the player tracking server 1000. Also, since the amount of computation is reduced, the computation velocity of player tracking may increase.

The player tracking system 100 according to an embodiment of the present disclosure may recognize and detect a playfield 3 included in the image data. Specifically, the player tracking server 1000 may perform an operation of recognizing and detecting a playfield included in the image data in consideration of a reference point of the playfield.

For example, the player tracking server 1000 may recognize and detect a playfield included in the image data in consideration of reference points such as a corner flag, a half line, a goal line, a touch line, and a penalty mark of the playfield. However, the above-described reference points are just examples, and a playfield included in image data may be recognized and detected in consideration of any appropriate region, line, point, or the like which is included in the playfield and which is capable of allowing the playfield to be recognized and detected.

The player tracking system 100 according to an embodiment of the present disclosure may perform an image stitching operation.

Specifically, the player tracking server 1000 of the player tracking system 100 may be provided to perform image stitching from at least one of image data to single image data.

As an example, image data may be acquired from at least one or more image capture devices disposed at different locations in the vicinity of the playfield. In this case, the player tracking server 1000 may generate a high-resolution image and a panoramic image by stitching at least one or more pieces of image data acquired from at least one or more image capture devices at the same time point into one piece of image data. In this case, when one or more pieces of image data are stitched into one piece of image data, the image data stitching operation may be performed based on a reference point included in an overlapping portion between the pieces of image data. The "reference point" included in the overlapping portion between the pieces of image data may be a point such as a penalty mark or a corner flag included in the image data. The "reference point" included in the overlapping portion between the pieces of image data may be a line such as a penalty line, a goal line, a touch line, or a center line included in the image data. The "reference point" included in the overlapping portion between the pieces of image data may be a region such as a center circle included in the image data. However, this is just an example, and any suitable reference point may be used to perform a stitching operation between pieces of image data.

The player tracking system 100 according to an embodiment of the present disclosure may acquire an image-based location from the image data.

Specifically, the player tracking server 1000 may analyze the image data to compute a location of a sport participant included in the image data.

As an example, the player tracking server 1000 may convert image data from a perspective view form to a top view form in order to compute the location of the sport participant. In this case, the player tracking server 1000 may consider an installation position of the image capture device that captures the image data or a relative location between sport participants acquired by the image capture device in order to convert coordinates from the perspective view form to the top view form. Also, the player tracking server 1000 may convert image data in a perspective view form to image data in a top view form with respect to a plane that is substantially the same as the playfield.

Specifically, the player tracking server 1000 may analyze the image data to compute a location of a sport participant included in the image data in the top view form. For example, the player tracking server 1000 may compute the location of the sport participant on the basis of a location of a pixel corresponding to the sport participant of the top-view image data. Preferably, the player tracking server 1000 may compute the location of the sport participant on the basis of a location of a pixel corresponding to a foot of the sport participant.

As described above, although the description was focused on the player tracking server 1000 computing a player's location on the basis of image data in the top view form, this is just an example. For example, the player tracking server 1000 may compute a player's location by acquiring a location of a pixel corresponding to a sport participant (e.g., foot) in image data in a form other than the top view form (e.g., in the perspective view form) and then projecting the pixel onto a plane that is substantially the same as the playfield in consideration of the height and the installation angle of the image capture device.

As another example, in tracking the sport participant by analyzing the image data to compute the location of the sport participant, various artificial neural networks such as CSRT, fast RCNN, and Depp sort may be used. However, the above-described artificial neural network is just an example, and any suitable algorithm or artificial neural network may be used to track sport participants.

For example, a sport participant included in image data may be segmented through the above-described artificial neural network, and the sport participant may be detected. When the sport participant is detected, a bounding box may be generated, and the player tracking server 1000 may compute the location of the sport participant on the basis of the bounding box. Preferably, the player tracking server 1000 may compute the location of the sport participant on the basis of the bottom line of the bounding box.

As another example, a "foot" of the sport participant included in the image data may be detected through the above-described artificial neural network, and the player tracking server 1000 may compute the location of the sport participant on the basis of a location of a pixel corresponding to the "foot" of the sport participant.

The player tracking system 100 according to an embodiment of the present disclosure may acquire a positioning sensor-based location from positioning sensor data. Specifically, the player tracking server 1000 may compute a player's location in consideration of data related to the player's location included in the positioning sensor data. For example, the player tracking server 1000 may compute or acquire a positioning sensor-based location on the basis of positioning sensor data through triangulation.

Here, the positioning sensor data may include data related to the player's location. Alternatively, the positioning sensor-based location may be acquired from data related to velocity or acceleration included in the positioning sensor data.

Also, the player tracking server 1000 may be provided to compute the velocity or acceleration of the sport participant from location-related data of the image data and location-related data of the positioning sensor data using a mathematical method such as calculus.

The player tracking system 100 according to an embodiment of the present disclosure may determine the validity of the acquired image-based location.

Specifically, the player tracking server 1000 may evaluate the validity of the image-based location of the player computed from the image data. More specifically, the player tracking server 1000 may be provided to consider at least one of the presence of a detected occlusion event, the severity of an occlusion event, a vertical movement of a player, and an internal disparity of a player's location computed from image data in order to evaluate the validity of the image-based location.

The following description will refer to FIGS. 5 to 8. FIGS. 5 to 8 are exemplary views illustrating a method of the player tracking server 1000 determining or detecting whether an occlusion event occurs between a plurality of players in image data according to an embodiment of the present disclosure.

As an example, the player tracking server 1000 may evaluate the validity of the player's location computed from the image data in consideration of whether an occlusion event is detected between a plurality of players in the image data. Here, the occlusion event may refer to an event in which the plurality of players at least partially overlap.

For example, the player tracking server 1000 may detect an occlusion event on the basis of image data in the form of an intensity map or an RGB map. For example, the player tracking server 1000 may recognize the sport participants included in the image data on the basis of any suitable artificial intelligence network as described above, and as a result of the recognition, a bounding box may be generated for each sport participant. In this case, the player tracking server 1000 may determine whether an occlusion has occurred in consideration of the degree to which the bounding boxes of the plurality of players overlap.

As an example, a threshold value related to the overlapping degree of the bounding boxes may be preset, and the player tracking server 1000 may determine that the occlusion event has occurred when the overlapping degree of the bounding boxes of the players exceeds the threshold value. On the contrary, the player tracking server 1000 may determine that no occlusion event has occurred when the bounding boxes of the players do not overlap or when the overlapping degree of the bounding boxes is less than the threshold value.

Figure 5:
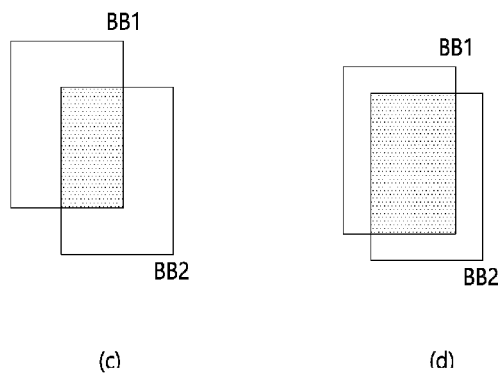
FIGS. 5 to 8 are exemplary diagrams illustrating a method of the player tracking server determining or detecting whether an occlusion event occurs between a plurality of players in image data according to an embodiment of the present disclosure.

In detail, the following description will refer to FIG. 5. FIG. 5 is a diagram showing that an occlusion is detected or determined according to the size or proportion of an overlapping region between a first bounding box BB1 corresponding to a first sport participant recognized from image data and a second bounding box BB2 corresponding to a second sport participant recognized from image data.

Referring to FIG. 5A, there may be a situation where the first bounding box BB1 and the second bounding box BB2 overlap. In this case, the player tracking server 1000 may determine that no occlusion event has occurred.

Referring to FIGS. 5B, 5C, and 5D, there may be a situation where the first bounding box BB1 and the second bounding box BB2 partially do not overlap. In this case, the player tracking server 1000 may determine whether an occlusion event has occurred on the basis of a first preset threshold value for the size or proportion of a region where the first bounding box BB1 and the second bounding box BB2 overlap.

For example, FIG. 5B may be a diagram showing that the size or proportion of the region where the first bounding box BB1 and the second bounding box BB2 overlap is smaller than the first preset threshold value. In this case, the player tracking server 1000 may determine that no occlusion event has occurred between the first sport participant and the second sport participant.

As another example, FIG. 5C may be a diagram showing that the size or proportion of the region where the first bounding box BB1 and the second bounding box BB2 overlap exceeds the first preset threshold value. In this case, the player tracking server 1000 may determine that an occlusion event has occurred between the first sport participant and the second sport participant.

As described above, it has been described that the player tracking server 1000 may determine whether an occlusion event has occurred, but the player tracking server 1000 may determine the severity of the occlusion event between the first sport participant and the second sport participant in additional consideration of a second preset threshold value.

For example, FIG. 5C may be a diagram showing that the size or proportion of the region where the first bounding box BB1 and the second bounding box BB2 overlap is smaller than the second preset threshold value. In other words, in the case of FIG. 5C, the player tracking server 1000 may determine that an occlusion event has occurred between the first sport participant and the second sport participant but the severity of the occlusion is not high.

On the contrary, FIG. 5D may be a diagram showing that the size or proportion of the region where the first bounding box BB1 and the second bounding box BB2 overlap is greater than the first threshold value and the second threshold value.

In this case, the player tracking server 1000 may determine that an occlusion event has occurred between the first sport participant and the second sport participant and the severity of the occlusion is high.

As another example, the player tracking server 1000 may detect an occlusion event on the basis of image data in the form of an RGB map (or an intensity map). Specifically, the player tracking server 1000 may detect an occlusion event using pixel data included in an RGB map and determine whether the occlusion event has occurred.

For example, when the sum of the numbers of pixels corresponding to a plurality of players included in the current image data is decreased to below a certain percentage of the sum of the numbers of pixels corresponding to a plurality of players included in image data when an occlusion event did not occur, the player tracking server 1000 may be implemented to determine that an occlusion event has occurred. To this end, any suitable threshold percentage may be preset for the certain percentage.

Figure 6:
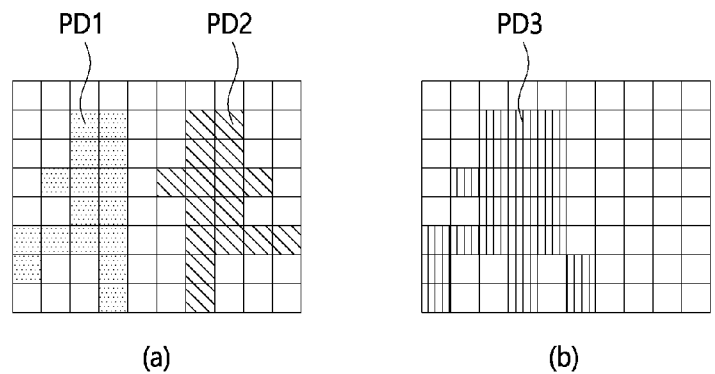

In detail, referring to FIG. 6, the player tracking server 1000 may acquire pixel data related to the first sport participant and the second sport participant from image data. In this case, the player tracking server 1000 may detect or determine whether an occlusion event has occurred between the first sport participant and the second sport participant in consideration of pixel data related to the first sport participant and pixel data related to the second sport participant.

In detail, FIG. 6A is a diagram showing a plurality of pieces of pixel data PD1 corresponding to the first sport participant and a plurality of pieces of pixel data PD2 corresponding to the second sport participant. In this case, the plurality of pieces of pixel data PD1 corresponding to the first sport participant and the plurality of pieces of pixel data PD2 corresponding to the second sport participant may not overlap.

FIG. 6B is a diagram showing a plurality of pieces of pixel data PD3 obtained by the plurality of pieces of pixel data PD1 corresponding to the first sport participant and the plurality of pieces of pixel data PD2 corresponding to the second sport participant partially overlapping.

According to a preferred embodiment, FIGS. 6A and 6B may show a plurality of pieces of pixel data related to the first sport participant and the second sport participant acquired from image data corresponding to two adjacent time points. In this case, the player tracking server 1000 may detect or determine whether an occlusion event has occurred in consideration of the ratio of the sum of the plurality of pieces of pixel data PD3 of FIG. 6B to the sum of the plurality of pieces of pixel data PD1 corresponding to the first sport participant and the plurality of pieces of pixel data PD2 corresponding to the second sport participant of FIG. 6A.

For example, a reference threshold ratio value indicating whether an occlusion event has occurred may be preset for the ratio of the sum of the plurality of pieces of pixel data PD3 of FIG. 6B to the sum of the plurality of pieces of pixel data PD1 corresponding to the first sport participant and the plurality of pieces of pixel data PD2 corresponding to the second sport participant. In this case, the player tracking server 1000 may determine that an occlusion event has occurred between the first sport participant and the second sport participant when the ratio of the sum of the plurality of pieces of pixel data PD3 of FIG. 6B to the sum of the plurality of pieces of pixel data PD1 corresponding to the first sport participant and the plurality of pieces of pixel data PD2 corresponding to the second sport participant is smaller than the reference threshold ratio value.

However, the above description is just an example, and any suitable method using pixel data may be used to determine whether an occlusion event has occurred. Also, by presetting an additional threshold ratio value, it is obvious that the player tracking server 1000 can determine not only the occurrence of the occlusion event but also the severity of the occlusion event.

As another example, the player tracking server 1000 may detect an occlusion event on the basis of data regarding a player's location included in positioning sensor data. Specifically, the player tracking server 1000 may acquire data which is related to locations of a plurality of players and which is included in positioning sensor data corresponding to the plurality of players. In this case, the player tracking server 1000 may determine whether an occlusion event has occurred in consideration of the number of players located within a predetermined radius from a specific player. Any suitable threshold value may be preset for the number of players located within the predetermined radius, and the player tracking server 1000 may determine that an occlusion event has occurred when the number of players located within the predetermined radius from the specific player is greater than the threshold value. On the other hand, when the number of players located within the predetermined radius from the specific player is smaller than the threshold value, the player tracking server 1000 may determine that no occlusion event has occurred.

Figure 7:
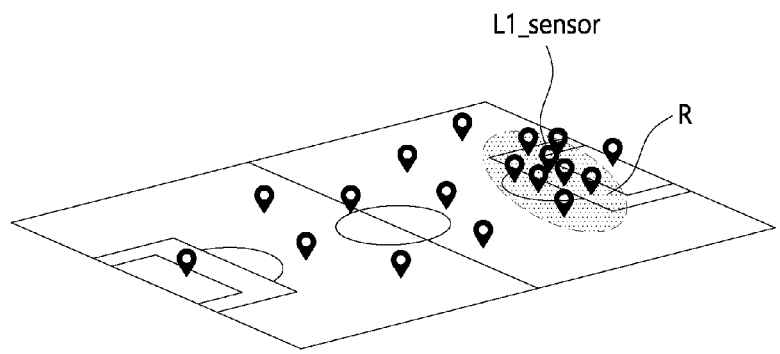

The following description will refer to FIG. 7. FIG. 7 is a diagram showing locations of a plurality of sport participants.

The locations of the plurality of sport participants may be locations acquired from image data or positioning sensor data. Preferably, the locations of the plurality of sport participants may be locations acquired from positioning sensor data. Also, preferably, the locations of the plurality of sport participants may be locations acquired by performing coordinate conversion on location-related data included in the positioning sensor data. In this case, the player tracking server 1000 may acquire the number of sport participants located in a region R within a predetermined radius from a specific location L1_sensor corresponding to a specific sport participant among locations corresponding to the plurality of sport participants. Also, the player tracking server 1000 may determine whether an occlusion event has occurred in consideration of the number of sport participants located in the region R within the predetermined radius from the specific location L1_sensor. For example, a threshold value may be preset for the number of sport participants located in the region R within the predetermined radius, and the player tracking server 1000 may determine that an occlusion event has occurred when the number of sport participants located in the region R within the predetermined radius from the specific location L1_sensor is greater than the threshold value. On the other hand, when the number of sport participants located in the region R within the predetermined radius from the specific location L1_sensor is smaller than the threshold value, the player tracking server 1000 may determine that no occlusion event has occurred.

As another example, the player tracking server 1000 may acquire data related to the arrangement and orientation of the image capture device. Also, the player tracking server 1000 may receive positioning sensor data including data related to each player's location from a positioning sensor device 200 worn by the corresponding player. In this case, the player tracking server 1000 may detect whether an occlusion has occurred in consideration of positioning sensor data including the data related to players' locations and the data related to the arrangement and orientation of the image capture device. For example, the player tracking server 1000 may detect or determine whether an occlusion has occurred on the basis of the players' locations computed from the positioning sensor data and data related to the line-of-sight and angle of the image capture device.

Figure 8:
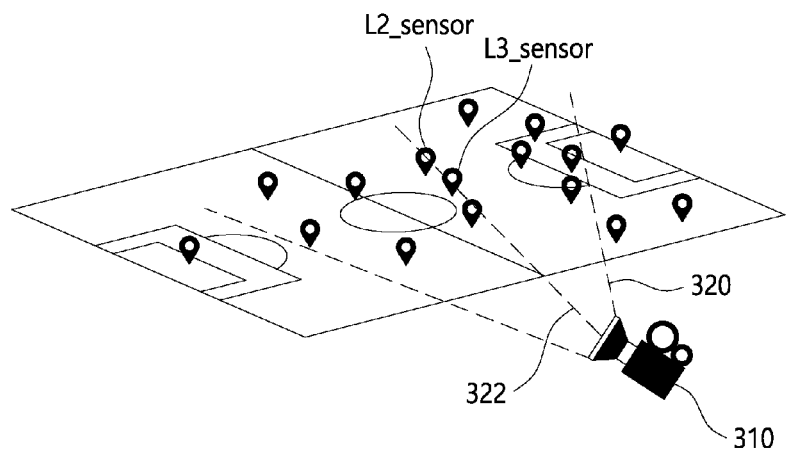

The following description will refer to FIG. 8. FIG. 8 is a diagram showing locations of a plurality of sport participants, a virtual point 310 corresponding to the image capture device 300, and virtual lines 320 and 322 for an orientation including the line-of-sight of the image capture device 300.

The locations of the plurality of sport participants may be locations acquired from image data or positioning sensor data. According to a preferred example, locations L2_sensor and L3_sensor of the plurality of sport participants may be locations acquired from the positioning sensor data. Also, preferably, the locations of the plurality of sport participants may be locations acquired by performing coordinate conversion on location-related data included in the positioning sensor data.

The virtual point 310 corresponding to the image capture device may be a location acquired from arrangement information including location information of the image capture device 300 located near the playfield. According to a preferred example, the virtual point 310 corresponding to the image capture device may be a location acquired by performing coordinate conversion on location-related data of the image capture device 300.

Information regarding the orientation of the image capture device related to the virtual line 320 and information regarding the line-of-sight of the image capture device related to the virtual line 322 may be acquired from the image capture device 300. According to a preferred example, the virtual line 322 corresponding to the line-of-sight of the image capture device may be a virtual line generated by performing coordinate conversion on the basis of a common coordinate system with the virtual point 310 or the locations L2_sensor and L3_sensor of the plurality of sport participants.

In this case, the player tracking server 1000 may detect or determine whether an occlusion has occurred between a plurality of sport participants in consideration of the virtual line 322 corresponding to the line-of-sight and the locations L2_sensor and L3_sensor of the plurality of sport participants. For example, the location L2_sensor of a first sport participant may be acquired from positioning sensor data acquired from positioning sensor devices 210 and 220 of the first sport participant, and the location L3_sensor of a second sport participant may be acquired from positioning sensor data acquired from positioning sensor devices 210 and 220 of the second sport participant. In this case, when the location L2_sensor of the first sport participant and the location L3_sensor of the second sport participant are substantially collinear with respect to the line of sight, the player tracking server 1000 may determine that an occlusion event has occurred between the first sport participant and the second sport participant.

As another example, the player tracking server 1000 may be implemented to determine whether an occlusion event has occurred in consideration of whether players related to the occlusion event are on the same team. Specifically, for the image data and especially image data in the form of an RGB map, teams of players may be distinguished on the basis of the similarity of pixels related to uniforms. Also, since identifiers of individual players are included in the positioning sensor data, teams of players may be distinguished based on the identifiers.

In this case, when the players related to the occlusion event are on the same team, the player tracking server 1000 may perform an operation of determining that an occlusion event has occurred. On the other hand, when the players related to the occlusion event are not on the same team, the player tracking server 1000 may determine that no occlusion event has occurred.

However, this is just an example, the player tracking server 1000 may determine that an occlusion event has occurred even though the players related to the occlusion event are not on the same team and may additionally evaluate validity related to a player's location computed from the image data during an operation of determining the severity of the occlusion event.

As another example, the player tracking server 1000 may be provided to detect or determine whether an occlusion event has occurred in consideration of a situation during a sport game. Specifically, during a sporting game, there may be a situation in which a plurality of players are concentrated, especially a corner kick situation. In this case, the player tracking server 1000 may recognize such a dense situation to estimate that an occlusion event has occurred.

The above-described occlusion event detection methods are just examples, and it is obvious that any suitable method for detecting an occlusion event between a plurality of players may be provided to the player tracking server 1000 in consideration of a player's location computed from image data and positioning sensor data and in an image in the form of an intensity map or an RGB map.

As described above, the player tracking server 1000 according to an embodiment of the present disclosure may detect whether an occlusion event has occurred between a plurality of players in the image data, and when the player tracking server 1000 determines that an occlusion event has occurred, a player's location computed from the image data may be determined to be invalid.

The player tracking server 1000 according to an embodiment of the present disclosure may be provided to evaluate the validity of the player's location computed from the image data in further consideration of the severity of the occlusion event between the plurality of players in the image data. Here, the severity of the occlusion event may be used in the sense of encompassing a concept of digitizing or quantifying the severity of the occlusion event in which the plurality of players at least partially overlap.

As an example, referring to FIG. 8 again, the player tracking server 1000 according to an embodiment of the present disclosure may determine the severity of the occlusion event in consideration of the number of sport participants located in the region R within the predetermined radius from the specific location L1_sensor and thus may evaluate the validity of the player's location computed from the image data.

For example, a plurality of threshold values (a first threshold value and a second threshold value) may be preset for the number of sport participants located in the region R within the predetermined radius, and the player tracking server 1000 may determine that the occlusion event has occurred and that the severity of the occlusion event is low (mild) when the number of sport participants located in the region R within the predetermined radius from the specific location L1_sensor is greater than the first threshold value and smaller than the second threshold value.

On the other hand, when the number of sport participants located in the region R within the predetermined radius from the specific location L1_sensor is greater than the second threshold value, the player tracking server 1000 may determine that an occlusion event has occurred and that the severity of the occlusion event is high (severe).

Apart from the severity of the occlusion event, when the number of sport participants located in the region R within the predetermined radius from the specific location L1_sensor is smaller than the first threshold value, the player tracking server 1000 may determine that no occlusion event has occurred.

As another example, the player tracking server 1000 according to an embodiment of the present disclosure may be provided to evaluate the validity of the player's location computed from the image data in further consideration of a team identifier even though it is determined that the occlusion event has occurred. For example, even though an occlusion event of a plurality of sport participants included in the image data has occurred, the player tracking server 1000 may evaluate the validity of the player's location computed from the image data by additionally determining the severity of the occlusion event according to a team identifier of the players related to the occlusion event.

Generally, when the sport participants are on the same team, the uniforms of the sport participants are the same. Thus, when an occlusion event occurs between the sport participants belonging to the same team, it is highly likely that the locations of the sport participants computed from the image data are invalid.

On the other hand, when the sport participants are on different teams, the uniforms of the sport participants are different. Thus, even when an occlusion event has occurred between the sport participants belonging to different teams, the locations of the sport participants may be validly acquired using pixel data of an RGB map associated with the color of the uniforms.

Therefore, the player tracking server 1000 according to an embodiment of the present disclosure may evaluate the validity of the player's location computed from the image data in further consideration of a team identifier even though it is determined that the occlusion event has occurred.

Pixel data related to the color of the uniforms acquired from the image data is illustrated as the team identifier, but this is just an example, and the team identifier, as well as the player identifier, may be further included in the positioning sensor data.

Figure 9:
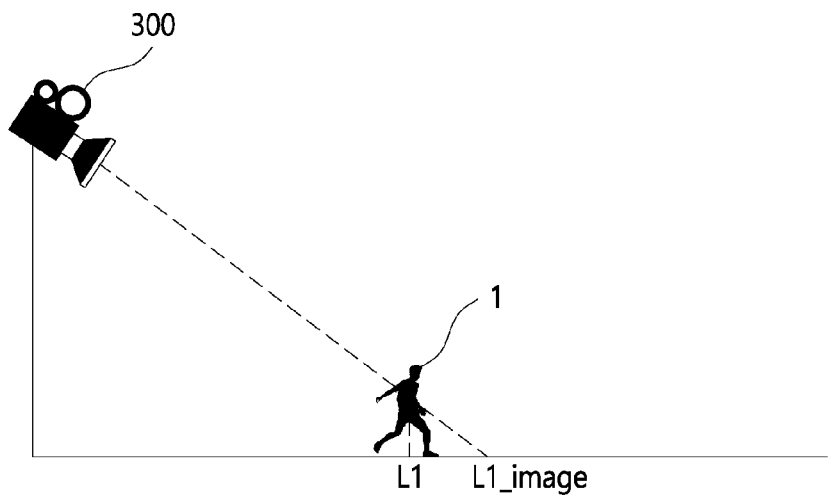
FIG. 9 is an exemplary diagram of a method of determining the validity of a player's location computed from image data according to the present disclosure.
Figure 9:
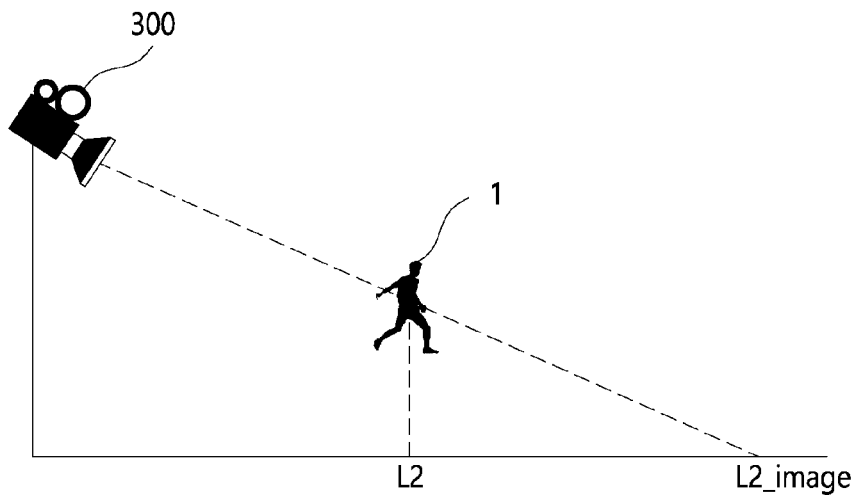

The following description will refer to FIG. 9. FIGS. 9A and 9B are exemplary diagrams of a method of determining the validity of the player's location computed from the image data according to the present disclosure.

As an example, the player tracking server 1000 may be provided to evaluate the validity of the player's location computed from the image data in consideration of the player's vertical movement included in the image data. Here, the vertical movement may have a meaning encompassing all movements in a direction perpendicular to a coordinate system plane related to the player's location computed from the image data. Specifically, data related to the vertical movement may be further acquired from an inertial sensor worn by players, and when the vertical movement is present, there is a possibility that an error may occur in the player's location computed from the image data. Therefore, the player tracking server 1000 may evaluate the validity of the player's location computed from the image data in consideration of the player's vertical movement included in the image data.

Referring to FIG. 9A, when there is substantially no vertical movement of a sport participant 1 included in image data, the difference between a location L1_image of the sport participant 1 computed from the image data and an actual location L1 of the sport participant 1 may be relatively small. In other words, when there is substantially no vertical movement of the sport participant 1 included in the image data, the location L1_image of the sport participant 1 computed from the image data may approximate the actual location L1.

On the other hand, referring to FIG. 9B, when there is a vertical movement of the sport participant 1 included in the image data, the difference between a location L2_image of the sport participant 1 computed from the image data and an actual location L2 of the sport participant 1 may be relatively large. In other words, when a vertical movement of the sport participant 1 is included in the image data, the location L2_image of the sport participant 1 computed from the image data is likely to have a significant error with respect to the actual location L2.

Therefore, the player tracking server 1000 may evaluate the validity of the player's location computed from the image data in consideration of the player's vertical movement included in the image data. For example, when a player's vertical movement included in the image data is detected, that is, when a change in z-direction data is detected by an inertial sensor worn by the sport participant 1, the player tracking server 1000 may determine that the location of the sport participant 1 computed from the image data is invalid.

As another example, when a player's vertical movement included in the image data is not detected, that is, when a change in z-direction data is not detected by an inertial sensor worn by the sport participant 1, the player tracking server 1000 may determine that the location of the sport participant 1 computed from the image data is valid.

As described above, it has been described that it is possible to evaluate the validity of a sport participant computed from the image data depending on whether the vertical movement of the sport participant is detected. This is just an example, and even when a vertical movement is detected, the validity of the location of the sport participant computed from the image data may be determined in further consideration of the direction or magnitude of acceleration in the z-direction. Also, information regarding the height, location, or capture angle of the image capture device 300 may be additionally provided and considered in determining whether the location of the sport participant computed from the image data is verified.

Figure 10:
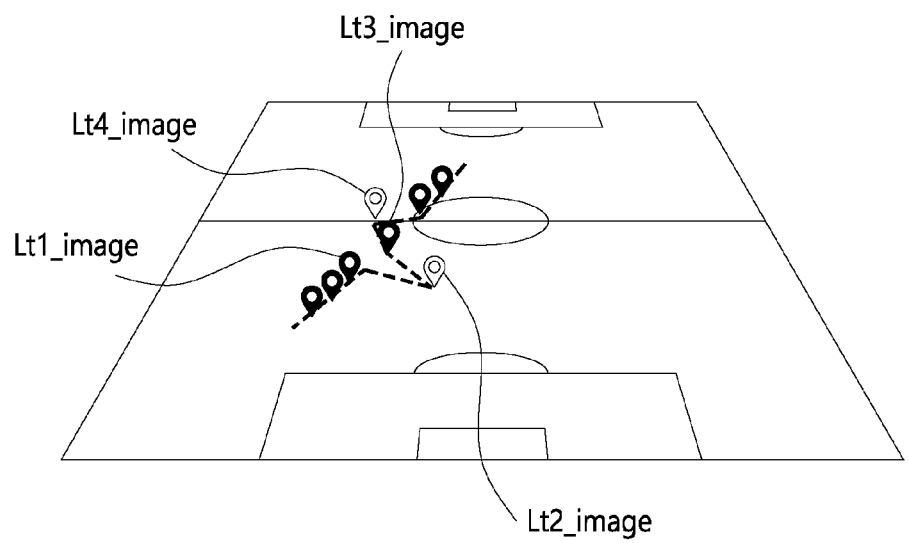
FIG. 10 is an exemplary diagram illustrating a method of determining the validity of a player's location computed from image data according to the present disclosure.
Figure 10:
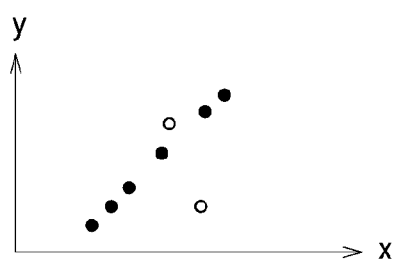

The following description will refer to FIG. 10. FIG. 10 is an exemplary diagram of a method of determining the validity of a player's location computed from image data according to the present disclosure.

As an example, the player tracking server 1000 may evaluate the validity of the player's location computed from the image data in consideration of an internal disparity of the player's location computed from the image data. Specifically, the player tracking server 1000 may continuously compute the player's location from the image data. In this case, when a change in the computed location of the player is greater than a predetermined threshold value, the player tracking server 1000 may determine that data regarding the greatly changed location of the player is invalid. In other words, when the change between the player's location computed from image data corresponding to a first time point and the player's location computed from image data corresponding to a second time point is greater than the predetermined threshold value, the player tracking server 1000 may determine that the player's location computed from the image data corresponding to the second time point is invalid.

Referring to FIG. 10, the player tracking server 1000 may be provided to compute or acquire locations of a specific sport participant from image data over time. In this case, when the difference between a location Lt1_image of the sport participant computed from the first time point and a location Lt2_image of the sport participant computed from the second time point is greater than the predetermined threshold value, the player tracking server 1000 may determine that the location Lt2_image of the sport participant computed from the second time point is invalid. On the other hand, when the difference between a location Lt3_image of the sport participant computed from a third time point and a location Lt4_image of the sport participant computed from a fourth time point is smaller than the predetermined threshold value, the player tracking server 1000 may determine that the location Lt4_image of the sport participant computed from the fourth time point is valid.

As described above, it has been described that the validity of the location of the sport participant computed from the image data over time is determined based on the preset threshold value, but this is just an example. Any suitable method may be used to determine the validity of the location of the sport participant computed from the image data. For example, the player tracking server 1000 may compute a trend line or the like by quantifying the tendency of the locations of the sport participant over time and may determine the validity of the location of the sport participant computed from the image data on the basis of the magnitude of deviation of the trend line or the like.

Also, the player tracking system 100 according to an embodiment of the present disclosure may determine the validity of an acquired positioning sensor-based location. Specifically, the player tracking server 1000 may evaluate the validity of the player's location computed from the positioning sensor data. More specifically, the player tracking server 1000 may consider at least one of reliability-related information of the positioning sensor data and the internal disparity of the player's location computed from the positioning sensor data in order to evaluate the validity of the player's location computed from the positioning sensor data.

Figure 11:
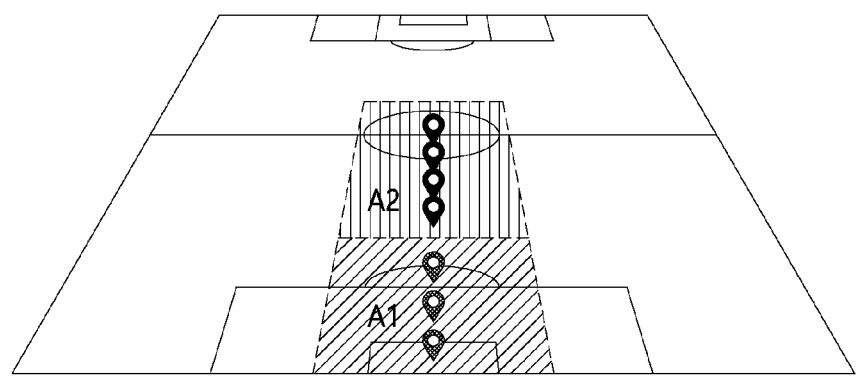
FIG. 11 is an exemplary diagram of a method of determining the validity of a player's location computed from positioning sensor data according to the present disclosure.

The following description will refer to FIG. 11. FIG. 11 is an exemplary diagram of a method of determining the validity of a player's location calculated from positioning sensor data according to the present disclosure.

As an example, the player tracking server 1000 may evaluate the validity of the player's location computed from the positioning sensor data in consideration of reliability-related information of a sensor signal included in the positioning sensor data.

For example, the reliability-related information (e.g., DoP, SNR) of a signal may be included in a signal transmitted from the Global Navigation Satellite System (GNSS) to a positioning sensor device.

In this case, the player tracking server 1000 may acquire the reliability-related information through the communication module 1100, and the player tracking server 1000 may evaluate the validity of the player's location computed from the positioning sensor data in consideration of the acquired reliability-related information of the sensor signal.

For example, a threshold value may be preset for the reliability-related information, and when the reliability-related information included in the positioning sensor data is greater than the preset threshold value, the player tracking server 1000 may determine that the player's location computed from the positioning sensor data is valid. On the other hand, when the reliability-related information included in the positioning sensor data is smaller than the preset threshold value, the player tracking server 1000 may determine that the player's location computed from the positioning sensor data is invalid.

Referring to FIG. 11, the reliability-related information of the sensor signal may be different for each region of the playfield. For example, when a sport participant is located in a first region A1 of the playfield, the reliability of the sensor signal may be relatively low. Therefore, location data included in positioning sensor data acquired from a positioning sensor device of the sport participant located in the first region A1 may have relatively low reliability. On the other hand, when a sport participant is located in a second region A2 of the playfield, the reliability of the sensor signal may be relatively high. Therefore, location data included in positioning sensor data acquired from a positioning sensor device of the sport participant located in the second region A2 may have relatively high reliability.

In this case, when the reliability of the sensor signal in the first region A1 is higher than the predetermined threshold value, the player tracking server 1000 may determine that the location of the sport participant computed from the positioning sensor data acquired from the positioning sensor device of the sport participant located in the first region A1 is valid. On the other hand, when the reliability of the sensor signal in the second region A2 is lower than the predetermined threshold value, the player tracking server 1000 may determine that the location of the sport participant computed from the positioning sensor data acquired from the positioning sensor device of the sport participant located in the second region A2 is invalid.

Also, the player tracking server 1000 may determine that the location of the sport participant computed based on data with high reliability is valid by quantifying and comparing the reliability of the sensor signal and the reliability of image data or may compute the location of the sport participant through weight values corresponding to the reliability of the sensor signal and the reliability of the image data. This will be described below with reference to FIG. 22.

In FIG. 11, it has been described that the first region and the second region are limited to specific regions in the playfield, but this is just an example for describing that the reliability of the sensor signal is different for each region.

Figure 12:
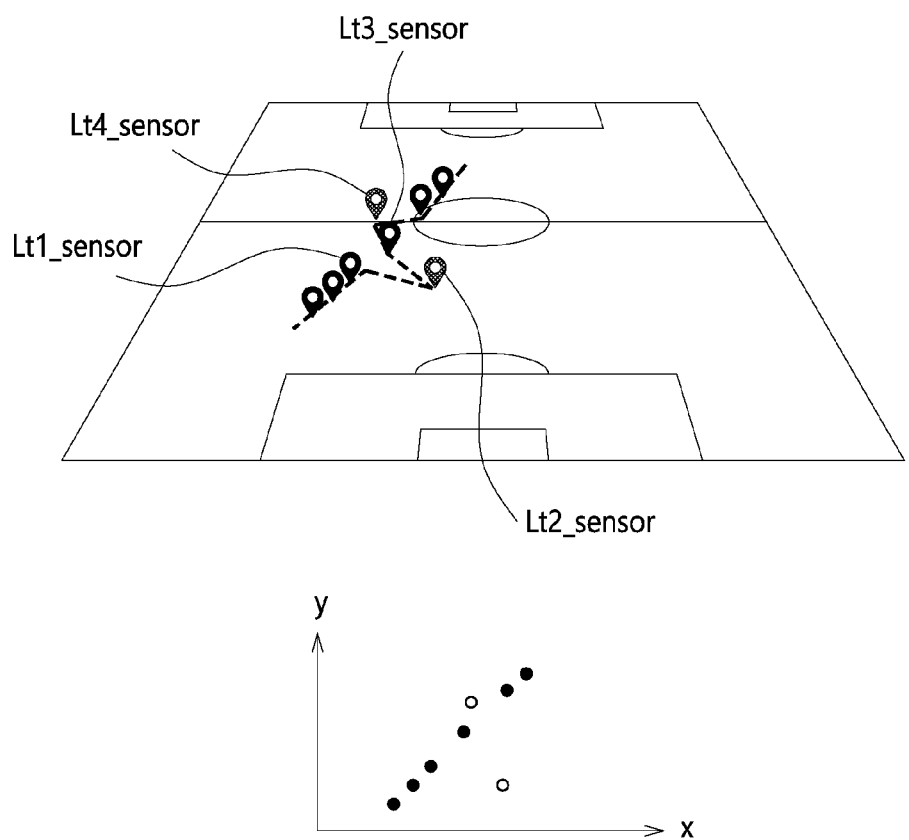
FIG. 12 is an exemplary diagram illustrating a method of determining the validity of a player's location computed from positioning sensor data according to the present disclosure.

The following description will refer to FIG. 12. FIG. 12 is an exemplary diagram illustrating a method of determining the validity of a player's location computed from positioning sensor data according to the present disclosure.

As an example, the player tracking server 1000 may evaluate the validity of the player's location computed from the positioning sensor data in consideration of an internal disparity of the player's location computed from the positioning sensor data. Specifically, the player tracking server 1000 may continuously compute or acquire the player's location from the positioning sensor data. In this case, when a change in the computed or acquired location of the player is greater than a predetermined threshold value, the player tracking server 1000 may determine that data regarding the greatly changed location of the player is invalid. In other words, when the change between the player's location computed from positioning sensor data corresponding to a first time point and the player's location computed from positioning sensor data corresponding to a second time point is greater than the predetermined threshold value, the player tracking server 1000 may determine that the player's location computed from the positioning sensor data corresponding to the second time point is invalid.

Referring to FIG. 12, the player tracking server 1000 may compute or acquire locations of a specific sport participant from positioning sensor data over time. In this case, when the difference between a location Lt1_sensor of the sport participant computed from the first time point and a location Lt2_sensor of the sport participant computed from the second time point is greater than the predetermined threshold value, the player tracking server 1000 may determine that the location Lt2_sensor of the sport participant computed from the second time point is invalid. On the other hand, when the difference between a location Lt3_sensor of the sport participant computed from a third time point and a location Lt4_sensor of the sport participant computed from a fourth time point is smaller than the predetermined threshold value, the player tracking server 1000 may determine that the location Lt4_sensor of the sport participant computed from the fourth time point is valid.

As described above, it has been described that the validity of the location of the sport participant computed from the positioning sensor data over time is determined based on the preset threshold value, but this is just an example. Any suitable method may be used to determine the validity of the location of the sport participant computed from the positioning sensor data. For example, the player tracking server 1000 may compute a trend line or the like by quantifying the tendency of the locations of the sport participant over time and may determine the validity of the location of the sport participant computed from the positioning sensor data on the basis of the magnitude of deviation of the trend line or the like.

The player tracking system 100 according to an embodiment of the present disclosure may determine the validity of at least one of an image-based location and a positioning sensor-based location on the basis of the difference between the image-based location and the positioning sensor-based location. Specifically, the player tracking server 1000 may be provided to determine the validity of at least one of the image-based location and the positioning sensor-based location. More specifically, the player tracking server 1000 may be provided to determine the validity of at least one of the image-based location and the positioning sensor-based location on the basis of an external disparity between the image-based location and the positioning sensor-based location.

As an example, the player tracking server 1000 may continuously compute or acquire a player's location from each of positioning sensor data and image data. In this case, the player tracking server 1000 may evaluate the validity of at least one of the player's location computed from the image data and the player's location computed from the positioning sensor data on the basis of a disparity index considering the difference (hereinafter referred to as an external disparity) between a first location of the player computed from the image data and a second location of the player computed from the positioning sensor data at the same time point.

For example, a disparity index between the first location and the second location computed at a first time point may be a first disparity index, and a disparity index between the first location and the second location computed at a second time point temporally adjacent to the first time point may be a second disparity index.

In this case, when the absolute value of the first disparity index ΔD1 is less than a predetermined first threshold value, the player tracking server 1000 may determine that at least one of the first location of the player computed from the image data at the first time point and the second location of the player computed from the positioning sensor data at the first time point is valid.

On the other hand, when the absolute value of the second disparity index ΔD2 exceeds a predetermined second threshold value, the player tracking server 1000 may evaluate that at least one of the first location of the player computed from the image data at the second time point and the second location of the player computed from the positioning sensor data at the second time point is invalid.

Here, the first threshold value and the second threshold value may be the same or may be preset to any suitable values different from each other.

As another example, the player tracking server 1000 may evaluate the validity of at least one of the player's location computed from the image data and the player's location computed from the positioning sensor data in consideration of the difference |ΔD1|−|ΔD2| or |ΔD1−ΔD2| between the first disparity index ΔD1 and the second disparity index ΔD2.

Specifically, when the difference |ΔD1|−|ΔD3| or ΔD1−ΔD2| between the first disparity index ΔD1 and the second disparity index ΔD2 is less than a third predetermined threshold value (preferably, when it is determined that the first location and the second location which are related to the first disparity index are valid), that is, when the difference between the first location of the player computed from the image data at the second time point and the second location of the player computed from the positioning sensor data at the second time point can be regarded as being within an error range, the player tracking server 1000 may determine that the first location and the first location at the second time point are valid.

On the other hand, when the difference |ΔD1|−|ΔD2| or |ΔD1−ΔD2| between the first disparity index ΔD1 and the second disparity index ΔD2 exceeds a fourth predetermined threshold value (preferably, when it is determined that the first location and the second location which are related to the first disparity index are valid), that is, when a time point at which the difference between the first location of the player computed from the image data at the second time point and the second location of the player computed from the positioning sensor data at the second time point changes significantly is detected, the player tracking server 1000 may determine that at least one of the first location and the second location at the second time point is invalid.

Here, the third threshold value and the fourth threshold value may be the same or may be preset to any suitable values different from each other.

The player tracking system 100 according to an embodiment of the present disclosure may be provided to generate reliability indices related to an image-based location and a positioning sensor-based location. Specifically, the player tracking server 1000 may be provided to generate the reliability index related to the image-based location and the reliability index related to the positioning sensor-based location on the basis of a validity determination result for the image-based location and the positioning sensor-based location.

Specifically, the player tracking server 1000 may generate a first reliability index of the player's location computed from positioning sensor data on the basis of the result of evaluating the validity of the positioning sensor data. For example, the first reliability index may be quantified from reliability-related information of a signal included in the positioning sensor data.

Also, the player tracking server 1000 may generate a second reliability index of the player's location computed from image data on the basis of the result of evaluating the validity of the image data. In this case, the second reliability index may be quantified as an index corresponding to the first reliability index so that the second reliability index can be quantitatively compared to the first reliability index.

In this case, the first reliability index and second reliability index may be used as one factor that should be considered in finally determining the location of the sport participant, which will be described below.

The player tracking system 100 according to an embodiment of the present disclosure may be provided to convert coordinates between the image-based location and the positioning sensor-based location. Specifically, the player tracking server 1000 may perform coordinate conversion between an image-based location and a positioning sensor-based location. Specifically, the player tracking server 1000 may be provided to perform coordinate conversion between an image-based location and a positioning sensor-based location. Thus, the image-based location may have the same coordinates as the positioning sensor-based location.

Specifically, the location of the player computed from the image data may be computed for a first coordinate system, and the location of the player computed from the positioning sensor data may be computed for a second coordinate system. In this case, the location of the player should be determined in consideration of both of the location of the player computed from the image data and the location of the player computed from the positioning sensor data or the location of the player if it is necessary to track the player, or the location of the player should be determined for a common coordinate system when switching is performed between the location of the player computed from the image data and the location of the player computed from the positioning sensor data. Thus, a conversion operation should be performed between the first coordinate system and the second coordinate system.

As an example, the second coordinate system may be converted to the first coordinate system.

As another example, the first coordinate system may be converted to the second coordinate system.

As still another example, the computed location of the player may be converted from the first coordinate system or the second coordinate system to an absolute coordinate system different from the first coordinate system and the second coordinate system.

However, the above-described conversion between the coordinate systems is just an example, and a player's location computed from image data and a player's location computed from positioning sensor data may be variously converted to a common coordinate system according to any suitable method.

In this case, the player tracking server 1000 may be provided to use various coordinate conversion algorithms.

As an example, the player tracking server 1000 may be implemented using an artificial neural network that is trained by any suitable method such as machine learning or deep learning.

Figure 13:
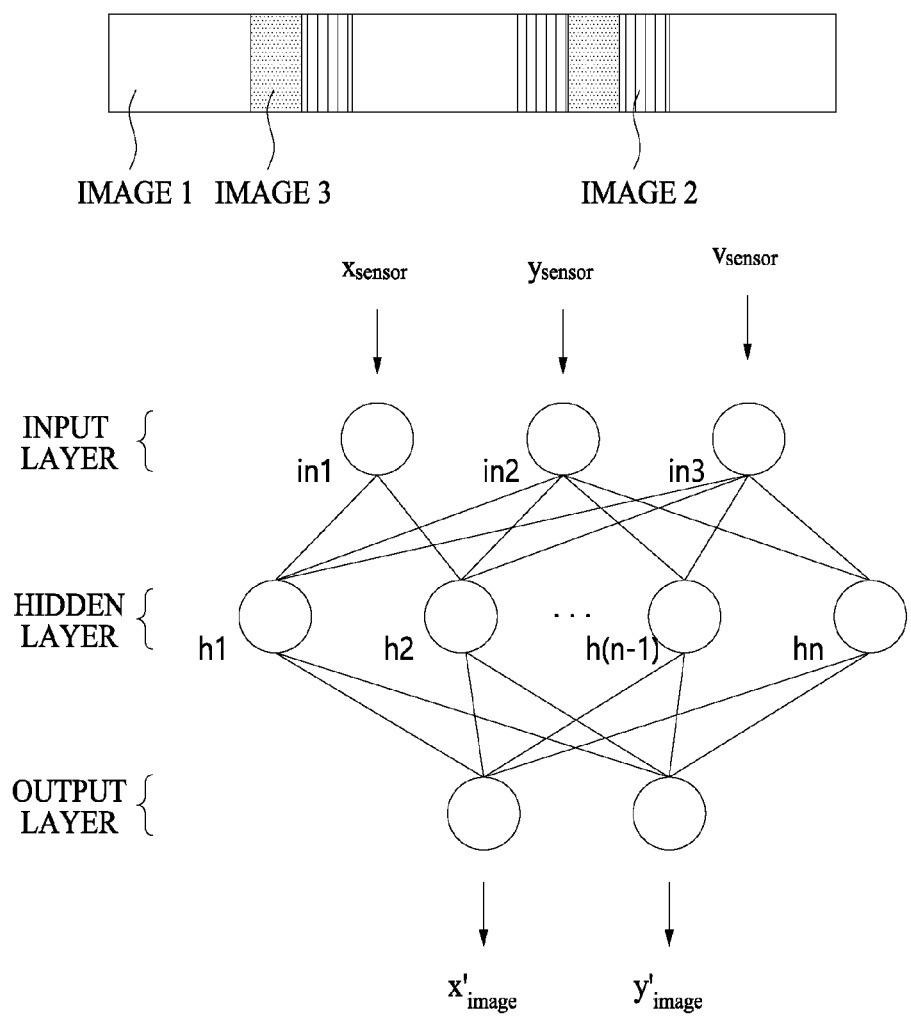
FIG. 13 is a diagram illustrating that an artificial neural network is trained to convert a location in a first coordinate system related to positioning sensor data into a location in a second coordinate system related to image data.
Figure 14:
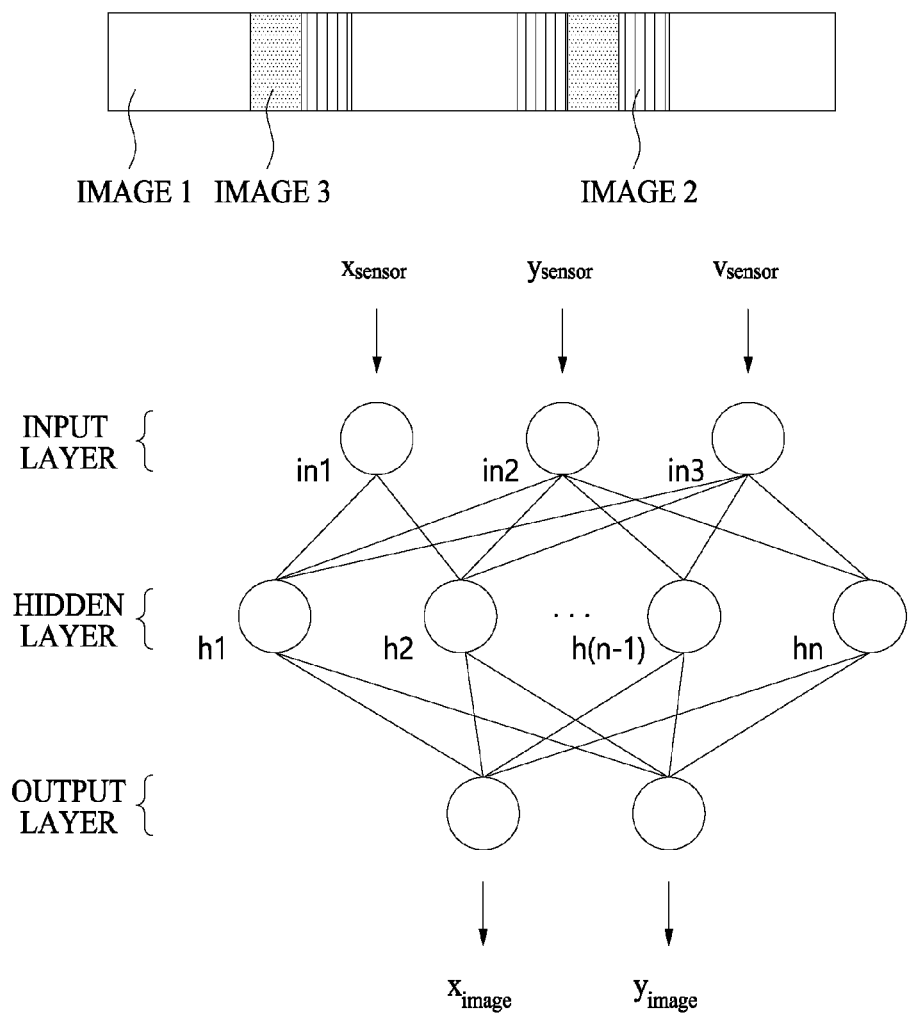
FIG. 14 is a diagram illustrating that a location in the first coordinate system related to positioning sensor data is converted to a location in the second coordinate system related to image data using the trained artificial neural network.

The following description will refer to FIGS. 13 and 14.

FIG. 13 is a diagram illustrating that an artificial neural network is trained to convert a location in a first coordinate system related to positioning sensor data to a location in a second coordinate system related to image data.

The following description will refer to FIG. 14. FIG. 14 is a diagram illustrating that a location in the first coordinate system related to positioning sensor data is converted to a location in the second coordinate system related to image data using the trained artificial neural network.

Referring to FIG. 14, the player tracking server 1000 according to an embodiment of the present disclosure may perform coordinate conversion from a location in a first coordinate system related to positioning sensor data to a location in a second coordinate system related to image data using an artificial neural network.

For example, when it is determined that an image-based location acquired from image data is invalid, there is a need to determine a location of a sport participant from a positioning sensor-based location acquired from positioning sensor data. However, since the positioning sensor-based location and the image-based location may have different coordinate systems, the player tracking server 1000 may convert an acquired positioning sensor-based location of the first coordinate system to a location of the second coordinate system related to image data. Here, the image-based location being invalid may refer to at least one of a case in which an occlusion is detected between sport participants and it is determined that an occlusion event is severe, a case in which a vertical movement of a sport participant is detected, and a case in which an internal disparity between image-based locations is present.

As an example, an artificial intelligence network to be trained to convert a location in the first coordinate system related to positioning sensor data to a location in the second coordinate system related to image data may include an input layer, a hidden layer including a plurality of nodes, and an output layer.

In order to train the artificial neural network, an image-based location (x_image, y_image) determined to be valid and a positioning sensor-based location (x_sensor, y_sensor) corresponding to the image-based location determined to be valid may be input to the input layer. Also, in order to perform accurate training, a positioning sensor-based speed |v|_sensor may be additionally input to the input layer in addition to the positioning sensor-based location (x_sensor, y_sensor) corresponding to the image-based location determined to be valid. In this case, the positioning sensor-based speed |v|_sensor may be computed from the positioning sensor-based location (x_sensor, y_sensor). Alternatively, the positioning sensor-based speed |v|_sensor may be computed from data acquired from an accelerometer of an inertial sensor worn by a sport sensor.

For example, referring to FIG. 13, the image data may include image data (image 1) in which no occlusion is detected, image data (image 2) in which an occlusion is detected but is determined not to be severe, and image data (image 3) in which an occlusion is detected and is determined to be severe.

In this case, as described above, an image-based location acquired by the image data (image 1) in which no occlusion is detected may be valid. That is, the image data (image 1) may be utilized to train the artificial neural network. Therefore, a first image-based location (x_image1, y_image1) acquired by the image data (image 1) in which no occlusion is detected and a first positioning sensor-based location (x_sensor1, y_sensor1) and a first positioning sensor-based speed |v|_sensor1 corresponding to the first image-based location may be used as input values for a training set.

In this case, as described above, an image-based location acquired by the image data (image 3) in which an occlusion is detected and is determined to be severe may be invalid. That is, when the image data (image 3) is utilized, to train the artificial neural network, the accuracy of the training may be reduced. Therefore, data related to the image data (image 3 in which an occlusion is detected and is determined to be severe may not be used as a training set.

Also, the image data (image 2) in which an occlusion is detected but is determined not to be severe may be appropriately selected to be used or not to be used as a training set in consideration of the above-described criterion.

Referring to FIG. 13 again, the positioning sensor-based location (x_sensor, y_sensor) and the positioning sensor-based speed |v|_sensor correspond to the image-based location that is input to the input layer and that is determined to be valid may be converted to a location (x'_image, y'_image) in coordinates of the image-based location through the hidden layer as an output value of the output layer.

In this case, the output value (x'_image, y'_image) may be compared to the image-based location (x_image, y_image) input to the input layer. Thus, by adjusting a weight value of a node included in the hidden layer on the basis of a difference between the output value and the image-based location, the artificial neural network may be trained.

Referring to FIG. 14, a location in the first coordinate system related to positioning sensor data may be converted to a location in the second coordinate system related to image data using the trained artificial neural network of FIG. 13. Preferably, the trained artificial neural network according to an embodiment of the present disclosure may be used to convert a location in the first coordinate system related to positioning sensor data to a location in the second coordinate system related to image data when it is determined that an image-based location is invalid.

For example, the image data may include image data (image 1) in which no occlusion is detected, image data (image 2) in which an occlusion is detected but is determined not to be severe, and image data (image 3) in which an occlusion is detected and is determined to be severe.

In this case, among the pieces of image data, an image-based location (x_image3, y_image3) acquired by the image data (image 3) in which an occlusion is detected and is determined to be invalid. In this case, when a positioning sensor-based location (x_sensor3, y_sensor3) and a positioning sensor-based speed |v|_sensor3 corresponding to the image-based location (x_image3, y_image3) acquired by the image data (image 3) in which an occlusion is detected and is determined to be severe are input to the input layer of the trained artificial neural network, the positioning sensor-based location (x_sensor3, y_sensor3) may be converted to a coordinate system related to the image-based location. Thus, even when the image-based location is invalid, the location of the sport participant may be continuously acquired based on the positioning sensor-based location.

In this case, among the pieces of image data, with regard to the image data (image 2) in which an occlusion is detected but is determined not to be severe, a reliability index of the image-based location may be compared to a reliability index of the positioning sensor-based location, which will be described below. When the positioning sensor-based location has higher reliability than the image-based location, the positioning sensor-based location may be provided to convert a coordinate value using the trained artificial neural network.

As described above, it has mainly been described that the positioning sensor-based location of the first coordinate system is converted to a location of the second coordinate system related to the image-based location. However, the artificial neural network may be trained to convert the positioning sensor-based location to a location in any suitable common coordinate system.

Also, it has mainly been described that the coordinates of the positioning sensor-based location are converted when the image-based location is invalid, but this is just an example. When it is determined that the positioning sensor-based location is invalid, it is obvious that it is possible to train or deploy an artificial neural network that converts the image-based location to the positioning sensor-based location in a similar method.

As described above, here, the player tracking server 1000 may use various coordinate conversion algorithms for coordinate conversion.

As an example, the coordinate conversion algorithm may be provided as a machine learning model. A representative example of the machine learning model may be an artificial neural network. Specifically, a representative example of the artificial neural network is a deep-learning-based artificial neural network including an input layer that receives data, an output layer that outputs a result, and a hidden layer that is between the input layer and the output layer to process data. Detailed examples of the artificial neural network are a convolutional neural network, a recurrent neural network, a deep neural network, and the like. Here, the artificial neural network should be interpreted in a comprehensive sense including the above-described artificial neural networks, other various types of artificial neural networks, and all combinations of the artificial neural networks, and does not necessarily have to be based on deep learning.

In addition, the machine learning model does not necessarily have to be in the form of an artificial neural network model. In addition, the machine learning model may include the k-nearest neighbors (KNN) algorithm, Random Forest, support vector machine (SVM), principal component analysis (PCA), and the like and may include ensembles of the aforementioned techniques or other various combinations thereof. Meanwhile, it should be noted that the artificial neural network can be replaced with another machine learning model unless otherwise stated in the embodiments mentioned focusing on the artificial neural network.

Furthermore, the coordinate conversion algorithm herein is not necessarily limited to the machine learning model. That is, the coordinate conversion algorithm may include various decision algorithms other than the machine learning model.

Therefore, it should be noted that the coordinate conversion algorithm herein should be understood in a comprehensive sense including all types of algorithms that perform coordinate conversion using data in a first coordinate system.

The player tracking system 100 according to an embodiment of the present disclosure may be provided to perform interpolation upon coordinate conversion between the image-based location and the positioning sensor-based location. Specifically, the player tracking server 1000 may additionally perform an operation of interpolating a converted coordinate value in order to correct an error that may occur during a coordinate conversion between the player's location computed from image data and the player's location computed from positioning sensor data. For example, while tracking the player using the player's location computed from the image data, the player tracking server 1000 may track the player using the player's location computed from positioning sensor data as necessary when it is determined that the player's location computed from the image data is invalid. In this case, when the player's location computed from the positioning sensor data is converted according to a first coordinate system of the player's location computed from the image data, there may be an error in the converted location value.

Therefore, the player tracking server 1000 according to an embodiment of the present disclosure may perform an operation of interpolating a value obtained by performing coordinate conversion on the player's location computed from the positioning sensor data according to the first coordinate system using the player's location which has been tracked before and which is computed from the image data.

The player tracking system 100 according to an embodiment of the present disclosure may determine the player's location in consideration of an image-based location and a positioning sensor-based location.

Specifically, the player tracking server 1000 may be provided to finally determine the player's location on the basis of an image-based location and a positioning sensor-based location.

As an example, when the image-based location is valid, the player tracking server 1000 may be provided to determine the player's location on the basis of the player's location computed from the image data.

On the other hand, when the image-based location is invalid, the player tracking server 1000 may determine the player's location on the basis of the location computed from the positioning sensor data.

For example, when it is determined or detected that there is no occlusion event between a plurality of players included in the image data and thus it is determined that the player's location computed from the image data is valid, the player tracking server 1000 may determine the player's location on the basis of the player's location computed from the image data. On the other hand, when it is determined or detected that there is an occlusion event between a plurality of players included in the image data and thus it is determined that the player's location computed from the image data is invalid, the player tracking server 1000 may determine the player's location on the basis of the location computed from the positioning sensor data.

As another example, when no vertical movement is detected with regard to a player included in the image data and thus it is determined that the player's location computed from the image data is valid, the player tracking server 1000 may determine the player's location on the basis of the player's location computed from the image data. On the other hand, when a vertical movement is detected with regard to a player included in the image data and thus it is determined that the player's location computed from the image data is invalid, the player tracking server 1000 may determine the player's location on the basis of the location computed from the positioning sensor data.

As another example, when an internal disparity between the player's locations computed from the image data does not exceed a predetermined threshold value and thus it is determined the player's location computed from the image data is valid, the player tracking server 1000 may determine the player's location on the basis of the player's location computed from the image data. On the other hand, when an internal disparity between the player's locations computed from the image data exceeds the predetermined threshold value and thus it is determined the player's location computed from the image data is invalid, the player tracking server 1000 may determine the player's location on the basis of the location computed from the positioning sensor data.

In an embodiment, when the player's location computed from the positioning sensor data is valid, the player tracking server 1000 may determine the player's location on the basis of the player's location computed from the positioning sensor data. On the other hand, when the player's location computed from the positioning sensor data is invalid, the player tracking server 1000 may determine the player's location on the basis of the location computed from the image data.

As an example, the player tracking server 1000 may determine the player's location on the basis of the determination that the player's location computed from the positioning sensor data is valid based on the reliability-related information of the signal included in the positioning sensor data.

For example, when it is determined that the player's location computed from the positioning sensor data is valid because the reliability of the signal included in the positioning sensor data is greater than a preset threshold value, the player tracking server 1000 may determine the player's location on the basis of the player's location computed from the positioning sensor data.

On the other hand, when it is determined that the player's location computed from the positioning sensor data is invalid because the reliability of the signal included in the positioning sensor data is smaller than the preset threshold value, the player tracking server 1000 may determine the player's location on the basis of the player's location computed from the image data.

As another example, when an internal disparity between the player's locations computed from the positioning sensor data does not exceed a predetermined threshold value and thus it is determined the player's location computed from the positioning sensor data is valid, the player tracking server 1000 may determine the player's location on the basis of the player's location computed from the positioning sensor data.

On the other hand, when an internal disparity between the player's locations computed from the positioning sensor data exceeds the predetermined threshold value and thus it is determined the player's location computed from the positioning sensor data is invalid, the player tracking server 1000 may determine the player's location on the basis of the location computed from the image data.

In an embodiment, the player tracking server 1000 may finally determine the player's location on the basis of the disparity indices of or the difference between the player's location computed from the image data and the player's location computed from the positioning sensor data.

Specifically, as described above, on the basis of the first disparity index ΔD1 between the first location of the player computed from the image data at the first time point and the second location of the player computed from the positioning sensor data at the first time point and the second disparity index ΔD2 between the first location of the player computed from the image data at the second time point and the second location of the player computed from the positioning sensor data at the second time point, it may be determined that at least one of the first location and the second location is invalid. In this case, the player tracking server 1000 may finally determine the player's location on the basis of the determination of the validity based on the disparity indices.

For example, when a computed disparity index is smaller than a predetermined first threshold value, that is, when it can be determined that both of the player's location computed from the positioning sensor data and the player's location computed from the image data are valid, the player tracking server 1000 may determine the player's location on the basis of one of the player's location computed from the positioning sensor data and the player's location computed from the image data.

On the other hand, when a computed disparity index is greater than a predetermined second threshold value, that is, when it can be determined that at least one of the player's location computed from the positioning sensor data and the player's location computed from the image data is invalid, the player tracking server 1000 may determine the player's location on the basis of the one of the player's location computed from the positioning sensor data and the player's location computed from the image data that has a higher reliability index.

Figure 15:
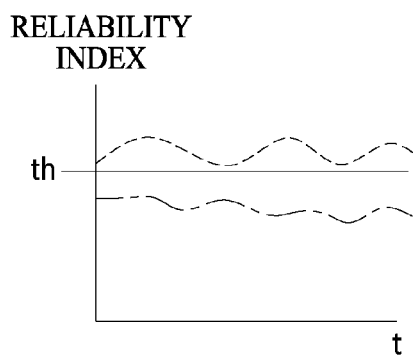
FIG. 15 is a diagram illustrating an exemplary method of a player tracking server determining a player's location according to an embodiment of the present disclosure.
Figure 15:
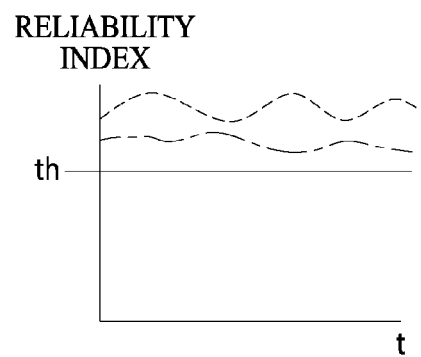
Figure 15:
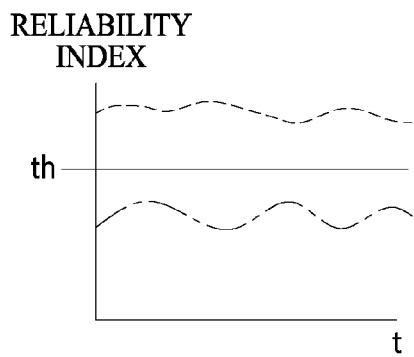
Figure 15:
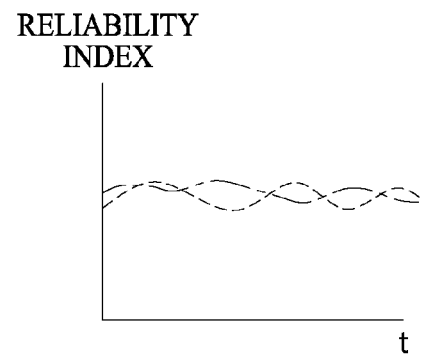

The following description will refer to FIG. 15. FIG. 15 is a diagram illustrating an exemplary method of determining a player's location on the basis of a reliability index according to an embodiment of the present disclosure.

In an embodiment, the player tracking server 1000 may determine the player's location on the basis of a comparison between the first reliability index related to the player's location computed from the image data and the second reliability index related to the player's location computed from the positioning sensor data.

As an example, when the first reliability index is higher than the second reliability index (FIG. 15A or FIG. 15B), the player tracking server 1000 may determine the player's location on the basis of the player's location computed from the image data.

For example, as shown in FIG. 15A, when the first reliability index is higher than a predetermined reliability threshold value and the second reliability index is lower than the predetermined reliability threshold value, the player tracking server 1000 may determine the location of the sport participant on the basis of the location of the sport participant computed from image data.

For example, as shown in FIG. 15B, when the first reliability index is higher than the second reliability index and the first reliability index and the second reliability index are higher than the predetermined reliability threshold value, the player tracking server 1000 may determine the location of the sport participant on the basis of the location of the sport participant computed from the image data, similar to FIG. 15A.

As another example, when the second reliability index is higher than the first reliability index (FIG. 15C), the player tracking server 1000 may determine the player's location on the basis of the player's location computed from the positioning sensor data.

As another example, as shown in FIG. 15C, when the second reliability index is higher than the predetermined reliability threshold value and the first reliability index is lower than the predetermined reliability threshold value, the player tracking server 1000 may determine the location of the sport participant on the basis of the location of the sport participant computed from positioning sensor data.

As another example, the player tracking server 1000 may determine the player's location by assigning weight values in consideration of the first reliability index related to the first location of the player computed from the image data and the second reliability index related to the second location of the player computed from the positioning sensor data. Specifically, the player tracking server 1000 may determine the player's location by assigning weight values considering the first reliability index and the second reliability index to the first location and the second location, respectively.

For example, as shown in FIG. 15B, when both of the first reliability index and the second reliability index are higher than the predetermined reliability threshold value, the player tracking server 1000 may determine the location of the sport participant by assigning weight values corresponding to the reliability indices to the first location of the sport participant computed from the image data and the second location of the sport participant computed from the positioning sensor data.

As another example, as shown in FIG. 15D, when the first reliability index is similar to or substantially the same as the second reliability index, the player tracking server 1000 may determine the location of the sport participant by assigning weight values corresponding to the reliability indices to the location of the sport participant computed from the image data and the location of the sport participant computed from the positioning sensor data.

As described above, it has been described that the location of the sport participant may be determined by assigning weight values corresponding to reliability indices in the case of FIGS. 15B and 15D, but this is just an example. It is obvious that the location of the sport participant may be determined by appropriately assigning the weight values corresponding to the reliability indices in the case of FIG. 15A or FIG. 15C or in any case.

The location of the sport participant determined by the player tracking server 1000 according to an embodiment of the present disclosure may be transferred to the memory 1200 through the communication module 1100 and stored in the memory 1200. Alternatively, the location of the sport participant determined by the player tracking server 1000 may be transmitted to an external server through the communication module 1100 or uploaded to the Internet.

The configuration and operation of the player tracking server 1000 according to an embodiment of the present disclosure have been described above. A player tracking method according to this embodiment will be described below. In the following description, the player tracking method according to an embodiment of the present disclosure is performed by the above-described player tracking system 100. However, this is just for convenience of description, and thus the player tracking method according to an embodiment of the present disclosure is not limited to the above-described player tracking system 100. That is, the player tracking method, which will be described below, does not necessarily have to be performed only by the player tracking system 100 but may be performed by another system or device having a function similar to that of the above-described player tracking system 100.

In addition, the configuration and operation of the player tracking server 1000 according to an embodiment of the present disclosure may be appropriately applied to other embodiments of the player tracking system 100, which will be described below.

Figure 16:
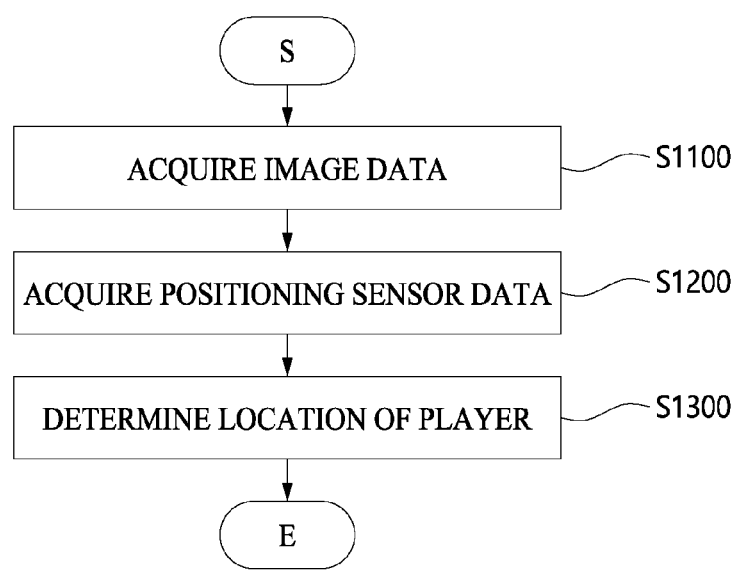
FIG. 16 is a flowchart illustrating a player tracking method according to an embodiment of the present disclosure.

The following description will refer to FIG. 16. FIG. 16 is a flowchart illustrating a player tracking method implemented by the player tracking system 100 according to an embodiment of the present disclosure.

The player tracking method according to an embodiment of the present disclosure may include acquiring image data (S1100), acquiring positioning sensor data (S1200), and determining a player's location (S1300).

In the operation of acquiring the image data (S1100), image data acquired from an image capture device 300 located near a playfield may be acquired.

In the operation of acquiring the positioning sensor data (S1200), positioning sensor data transmitted from a positioning sensor device 200 worn by a sport participant 1 may be acquired.

In this case, the image data and the positioning sensor data acquired by the player tracking server 1000 may be data adjusted to be in time synchronization with each other.

Also, the image data acquired by the player tracking server 1000 may be re-sampled data.

Also, the image data acquired by the player tracking server 1000 may be data from which noise is removed.

Also, the positioning sensor data acquired by the player tracking server 1000 may be positioning sensor data that has undergone a processing process, such as noise removal, amplification, and filtering.

Also, the image data acquired by the player tracking server 1000 may include location-related data of the sport participant and data related to a pixel corresponding to the sport participant.

Also, the player tracking server 1000 may additionally acquire identification data related to the type of image capture device that captures the image data and arrangement information related to the location, orientation, and the like of the image capture device. However, the above description is just an example, and the player tracking server 1000 may be implemented to include any suitable data.

Also, the positioning sensor data acquired by the player tracking server 1000 may include location-related data of the sport participant, reliability-related information of a sensor signal, and identifier-related data of the sport participant. However, the above description is just an example, and the player tracking server 1000 may be implemented to include any suitable data.

In the operation of determining the player's location (1300), the player's location may be determined based on at least one of the image data and the positioning sensor data.

As an example, the player tracking server 1000 may verify the validity of the image-based location computed from the image data and may determine that the player's location is the image-based location when the image-based location is valid. On the other hand, when the image-based location computed from the image data is invalid, the player tracking server 1000 may determine that the player's location is the player's location computed from the positioning sensor data. This will be described in detail with reference to FIGS. 17 to 19.

As an example, the player tracking server 1000 may verify the validity of the positioning sensor-based location computed from the positioning sensor data and may determine that the player's location is the positioning sensor-based location when the positioning sensor-based location is valid. On the other hand, when the positioning sensor-based location computed from the positioning sensor data is invalid, the player tracking server 1000 may determine that the player's location is the image-based location computed from the image data. Alternatively, when the positioning sensor-based location computed from the positioning sensor data is invalid, the player tracking server 1000 may additionally evaluate the validity of the image-based location and may determine the player's location on the basis of a result of evaluating the validity of the image-based location. This will be described in detail with reference to FIGS. 20 and 21.

As another example, the player tracking server 1000 may determine the player's location by quantifying and comparing the reliability of the positioning sensor-based location acquired from the positioning sensor data and the reliability of the image-based location acquired from the image data. Specifically, the player tracking server 1000 may determine the player's location on the basis of the one of the positioning sensor-based location and the image-based location that has higher reliability or may determine the player's location by assigning weight values corresponding to the reliability to the positioning sensor-based location and the image-based location. This will be described in detail below with reference to FIG. 22.

As another example, the player tracking server 1000 may determine the player's location on the basis of a reliability map of a positioning sensor-based location for each region of the playfield and a reliability map of an image-based location for each region of the playfield. More specifically, the reliability of the computed positioning sensor-based location of the player may differ for each region of the playfield. Also, the reliability of the computed image-based location of the player may differ for each region of the playfield. Therefore, the player tracking server 1000 may select one of the positioning sensor-based location and the image-based location on the basis of the reliability map and determine the selected location as the player's location or may determine the player's location by assigning weight values corresponding to the reliability to the positioning sensor-based location and the image-based location. This will be described in detail below with reference to FIGS. 23 to 25.

When a location of a sport participant is determined from image data acquired from an image capture device, it is possible to accurately measure the location of the sport participant, and the influence of structures near a playfield is relatively small. Furthermore, it is relatively easy to recognize or analyze the sport participant's motion, and it is possible to provide convenient use indoors. Also, conveniently, the sport participant does not need to wear a positioning sensor device. However, an occlusion event may occur between sport participants, and the amount of computation is relatively large because the size of image data is large.

On the other hand, when a location of a sport participant is determined from positioning sensor data acquired from a positioning sensor device, an occlusion event that may occur in determining the location of the sport participant from image data does not occur, and the size of the positioning sensor data is relatively smaller than that of the image data. Thus, the processing efficiency of the positioning sensor data may be relatively higher than that of the image data.

Therefore, in the player tracking method according to an embodiment of the present disclosure, a location of a sport participant may be determined from image data. However, the location of the sport participant may be determined from the positioning sensor data only when the location of the sport participant computed from the image data is invalid.

Figure 17:
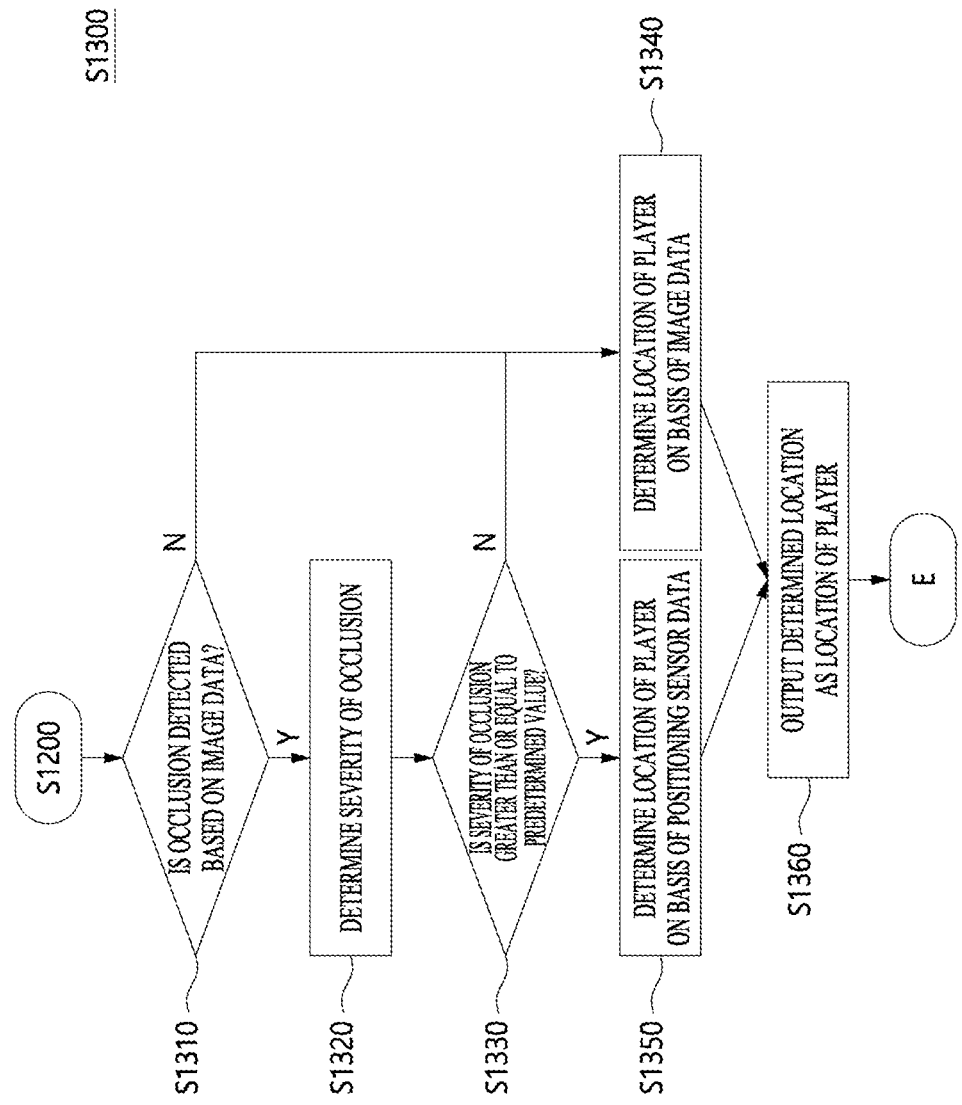
FIG. 17 is a flowchart illustrating the player tracking method according to an embodiment of the present disclosure and is a diagram illustrating operation S1300 of FIG. 16 in detail.

The following description will refer to FIG. 17. FIG. 17 is a flowchart illustrating the player tracking method according to an embodiment of the present disclosure and is a diagram illustrating operation S1300 of FIG. 16 in detail.

Referring to FIG. 17, operation S1300 according to an embodiment of the present disclosure may include detecting an occlusion on the basis of image data (S1310), determining the severity of the occlusion (S1320), determining whether the severity of the occlusion is greater than or equal to a predetermined threshold value (S1330), determining a player's location on the basis of positioning sensor data or image data (S1340 or S1350), and outputting the determined location as the player's location (S1360).

In operation S1310, an occlusion event may be detected between sport participants included in the image data. Specifically, the above-described player tracking server 1000 may detect an occlusion event between sport participants included in the image data. Alternatively, the player tracking server 1000 may determine whether an occlusion event between sport participants included in the image data has occurred.

In this case, when an occlusion event is not detected between the sport participants or it is determined that no occlusion event has occurred between the sport participants in operation S1310, the player tracking server 1000 may determine the location of the sport participant on the basis of a location computed from the image data.

On the other hand, when an occlusion event is detected between the sport participants or it is determined that an occlusion event has occurred between the sport participants in operation S1310, the operation of determining the severity of the occlusion event (S1320) may be performed. In operation S1320, the player tracking server 1000 may additionally determine the severity of the detected occlusion event.

As an example, the player tracking server 1000 may determine the severity of the occlusion event in consideration of the degree to which bounding boxes corresponding to the sport participants acquired from the image data overlap as described above.

As another example, the player tracking server 1000 may determine the severity of the occlusion event in consideration of a change in the total number of pixels corresponding to the sport participants acquired from the image data as described above.

As another example, the player tracking server 1000 may determine the severity of the occlusion event on the basis of the number of sport participants located within a predetermined region from a specific sport participant in consideration of the locations of the sport participants acquired from the positioning sensor data as described above.

As another example, the player tracking server 1000 may determine the severity of the occlusion event in consideration of team information of the sport participants related to the occlusion event as described above. The team information of the sport participants may be acquired from pixel information corresponding to the uniforms of the sport participants in the image data and especially in an RGB map. Alternatively, the team information of the sport participants may be acquired from an identifier included in the positioning sensor data.

As another example, the player tracking server 1000 may determine the severity of the occlusion event in consideration of a "situation" of a game in which the occlusion event is detected as described above.

In this case, the severity of the occlusion event may be quantified by any suitable method. Alternatively, an occlusion event may be classified by any suitable criterion according to the degree of severity.

In operation S1330, it may be determined whether a result of determining the severity of the occlusion event derived in operation S1320 is greater than or equal to a predetermined value. Specifically, the player tracking server 1000 may determine whether the severity value of the occlusion event quantified in operation S1320 is greater than or equal to the predetermined value.

As an example, when the quantified severity value of the occlusion event is greater than or equal to the predetermined value, it may be determined or predicted that the location of the sport participant computed based on the image data is invalid. Therefore, in operation S1350, when the quantified severity value of the occlusion event is greater than or equal to the predetermined value, the player tracking server 1000 may determine the location of the sport participant on the basis of a positioning sensor-based location computed based on the positioning sensor data rather than the image data.

As another example, when the quantified severity value of the occlusion event is less than the predetermined value, it may be determined or predicted that the location of the sport participant computed based on the image data is valid. Therefore, in operation S1340, when the quantified severity value of the occlusion event is less than the predetermined value, the player tracking server 1000 may determine the location of the sport participant on the basis of an image-based location computed based on the image data.

Alternatively, the player tracking server 1000 may determine whether to determine the player's location on the basis of the image data or on the basis of the positioning sensor data according to the result of classifying the severity of the occlusion event in operation S1320.

As an example, the player tracking server 1000 may designate the occlusion event as a mild occlusion event or a severe occlusion event depending on the severity of the occlusion event. In this case, the player tracking server 1000 may determine the location of the sport participant on the basis of the image data according to the result of designating the occlusion event as the mild occlusion event. On the other hand, the player tracking server 1000 may determine the location of the sport participant on the basis of the positioning sensor data according to the result of designating the occlusion event as the severe occlusion event.

In operation S1360, the location of the sport participant may be output or updated on the basis of the determined location of the sport participant. The output location of the sport participant may be a coordinate value corresponding to any suitable coordinate system.

Figure 18:
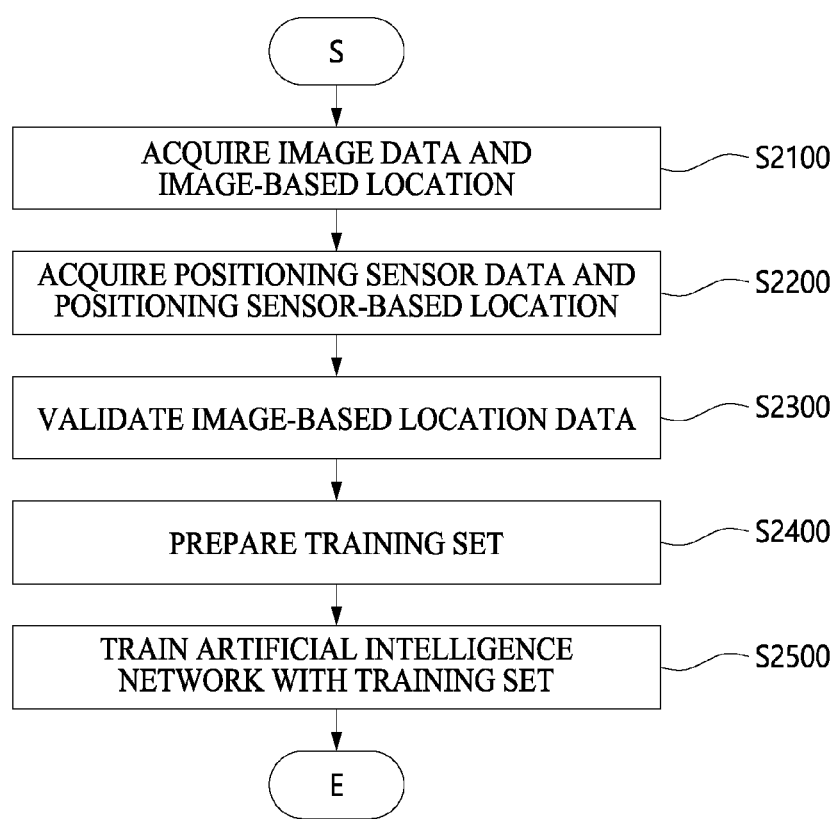
FIG. 18 is a flowchart illustrating a training process for an artificial neural network related to a coordinate conversion algorithm according to an embodiment of the present disclosure.

The following description will refer to FIG. 18. FIG. 18 is a flowchart illustrating a training process for an artificial neural network related to a coordinate conversion algorithm according to an embodiment of the present disclosure.

A training method using an artificial neural network of a coordinate conversion unit according to an embodiment of the present disclosure may include acquiring image data and an image-based location (S2100), acquiring sensor data and a positioning sensor-based location (S2200), verifying the image-based location (S2300), preparing a training set (S2400), and training the artificial neural network using the training set (S2500). The training method using the artificial neural network may be implemented by the player tracking server 1000 according to an embodiment of the present disclosure or in any separate training module.

In operation S2100, image data transmitted from the image capture device 300 may be acquired. Also, an image-based location may be acquired from the image data. The image-based location may be acquired from a coordinate value of a pixel corresponding to a location of a sport participant included in the image data.

In operation S2200, positioning sensor data transmitted from the positioning sensor device 210 or 220 may be acquired. Also, a positioning sensor-based location may be acquired from the positioning sensor data. The positioning sensor-based location may be acquired from location-related data included in the positioning sensor data or may be acquired from velocity- or acceleration-related data included in the positioning sensor data. Specifically, in operation S2200, a positioning sensor-based location and a positioning sensor-based speed corresponding to the image-based location may be acquired.

In operation S2300, whether the image-based location acquired in operation S2100 is usable as a training set may be verified based on the result of determining the validity of the image-based location.

As an example, the player tracking server 1000 may determine the validity of the image-based location on the basis of whether the occlusion event is detected. In other words, in operation S2300, whether the image-based location is usable as a training set may be verified based on the result of detecting the occlusion event in the image data.

For example, when an occlusion event is detected in the image data, it may be determined that the acquired image-based location is not appropriate as a training set.

For example, when no occlusion event is detected in the image data (or when an occlusion event is detected and is determined not to be severe), it may be determined that the acquired image-based location is usable as a training set.

In operation S2400, the training set and the artificial neural network may be prepared according to the verification result of operation S2300.

The artificial neural network may include an input layer, an output layer, and a hidden layer including a plurality of nodes.

The training set may include the image-based location verified in operation S2300 and a positioning sensor-based location and a positioning sensor-based speed corresponding to the image-based location. In this case, the image-based location may be a location related to a first coordinate system. Also, the positioning sensor-based location may be a location related to a second coordinate system different from the first coordinate system.

In operation S2500, the artificial neural network may be trained using the training set prepared in operation S2400.

For example, the positioning sensor-based location and the positioning sensor-based speed of the training set may be input to the input layer. In this case, the input positioning sensor-based location and positioning sensor-based speed may be converted from the second coordinate system to the first coordinate system through the artificial neural network and then may be output through the output layer. In this case, weight values of the nodes included in the hidden layer may be adjusted based on a difference between the image-based location of the training set and the output value output through the output layer.

By appropriately adjusting the weight values of the plurality of nodes, the artificial neural network may be trained such that errors between the image-based location of the training set and output values output through the output layer can be reduced.

Figure 19:
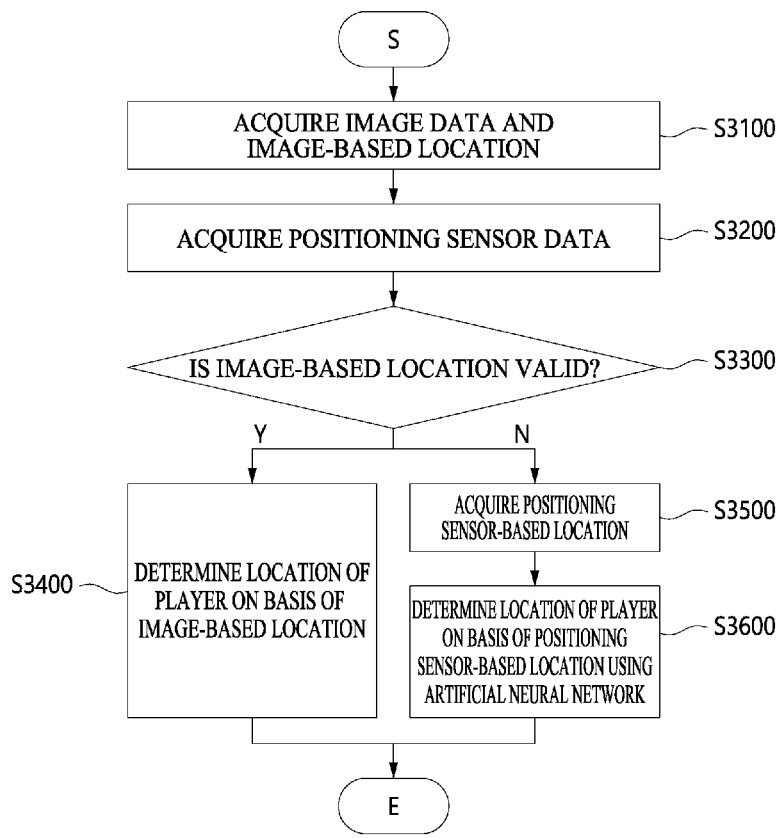
FIG. 19 is a flowchart illustrating a player tracking method through coordinate conversion using the trained artificial neural network.

FIG. 19 is a flowchart illustrating an example of the player tracking method through coordinate conversion using the trained artificial neural network of FIG. 18.

The player tracking method through coordinate conversion using the trained artificial neural network may include acquiring image data and an image-based location (S3100), acquiring positioning sensor data (S3200), determining the validity of the image-based location (S3300), and determining a location of a sport participant (S3400, S3500, or S3600).

In operation S3100, image data transmitted from the image capture device 300 may be acquired. Also, an image-based location may be acquired from the image data. The image-based location may be acquired from a coordinate value of a pixel corresponding to a location of a sport participant included in the image data.

In operation S3200, positioning sensor data transmitted from the positioning sensor device 200 may be acquired.

In operation S3300, the player tracking server 1000 may determine the validity of the image-based location.

As an example, according to any suitable method of determining the validity of the image-based location that has been described with reference to FIGS. 5 to 10, the validity of the image-based location acquired in operation S3100 may be determined or predicted.

For example, the validity of the image-based location may be determined by the player tracking server 1000 in consideration of at least one of the presence of a detected occlusion event, a result of determining the severity of the occlusion event, a vertical movement of a sport participant, and an internal disparity of the image-based location.

In operation S3400, when it is determined in operation S3300 that the image-based location is valid, the player tracking server 1000 may determine the location of the sport participant on the basis of the image-based location.

On the other hand, when it is determined in operation S3300 that the image-based location is invalid, the player tracking server 1000 may determine the location of the sport participant on the basis of the positioning sensor data.

In operation S3500, a positioning sensor-based location may be acquired from the positioning sensor data acquired in operation S3200. The positioning sensor-based location may be acquired from location-related data included in the positioning sensor data or may be acquired from velocity- or acceleration-related data included in the positioning sensor data. Specifically, in operation S3500, a positioning sensor-based location and positioning sensor-based speeds corresponding to the image-based location may be acquired.

Referring to FIG. 19, it is shown that the positioning sensor-based location is acquired only when it is determined in operation S3300 that the image-based location is invalid, but this is just an example. It is obvious that the positioning sensor-based location or the positioning sensor-based speed may be computed from the positioning sensor data in operation S3200 as well as in operation S3500.

In operation S3600, the positioning sensor-based location and the positioning sensor-based speed acquired in operation S3500 may be input as an input value of the input layer of the trained artificial neural network.

The positioning sensor-based location and the positioning sensor-based speed may be values acquired in the second coordinate system. Also, the positioning sensor-based location and the positioning sensor-based speed may be values of a location and a speed corresponding to the image-based location determined to be invalid.

In operation S3600, as the positioning sensor-based location and the positioning sensor-based speed of the second coordinate system input to the input layer may pass through the artificial neural network, coordinates may be converted with respect to the image-based location of the first coordinate system.

The player tracking server 1000 may determine the location of the sport participant on the basis of the value output in operation S3600.

With the above-described player tracking method according to an embodiment according to the present disclosure, by tracking a player on the basis of image data first, it is possible to facilitate recognition of a behavior or situation of a sport participant, and it is also possible to implement location measurement with relatively high accuracy, which are merits of the image data. However, in the case of image data, it may be difficult to distinguish objects due to occlusion events, etc., and data processing efficiency may be slightly lower because the data size is relatively large. However, such disadvantages of image data can be compensated for with positioning sensor data.

When the location of the sport participant is determined from positioning sensor data acquired from a positioning sensor device, it is easy to distinguish between sport participants, and even at night, it is possible to easily compute the locations of sport participants. Furthermore, the amount of computation is small because the data size is relatively small. Also, conveniently, image capture devices do not have to be installed in advance near a playfield or the like. However, sport participants need to wear positioning sensor devices, and the influence of structures near a playfield may be great. Also, it may be relatively complicated to recognize events or behaviors of sport participants compared to image data.

On the other hand, when a sport participant's movement is tracked based on image data acquired from an image capture device, structures near a playfield do not have any influence, and it is easy to recognize events or behaviors of sport participants.

Therefore, in another example of the player tracking method according to an embodiment of the present disclosure, a location of a sport participant may be determined from positioning sensor data. However, the location of the sport participant may be determined in further consideration of the location of the sport participant computed from image data only when the location of the sport participant computed from the positioning sensor data is invalid.

The player tracking method according to another embodiment of the present disclosure may be implemented by the player tracking system 100 shown in FIG. 3. Also, the player tracking method according to an embodiment of the present disclosure may be implemented by the player tracking server 1000 shown in FIG. 4.

Figure 20:
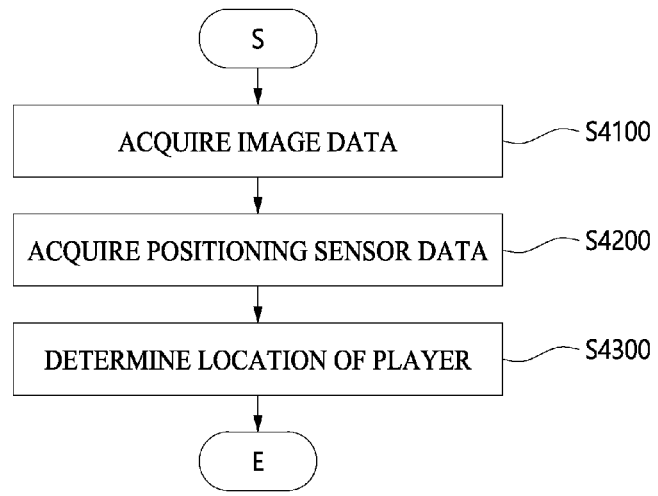
FIG. 20 is a flowchart illustrating a player tracking method according to an embodiment of the present disclosure.

The following description will refer to FIG. 20. FIG. 20 is a flowchart illustrating a player tracking method according to an embodiment of the present disclosure. Referring to FIG. 20, the player tracking method according to an embodiment of the present disclosure may include acquiring image data (S4100), acquiring positioning sensor data (S4200), and determining a player's location (S4300).

The details of operations S1100, S1200, and S1300 described with reference to FIG. 16 may be equally applied to operations S4100, S4200, and S4300. Therefore, the following description will focus on the details of FIG. 21 different from or added to those of FIGS. 16 to 19.

Figure 21:
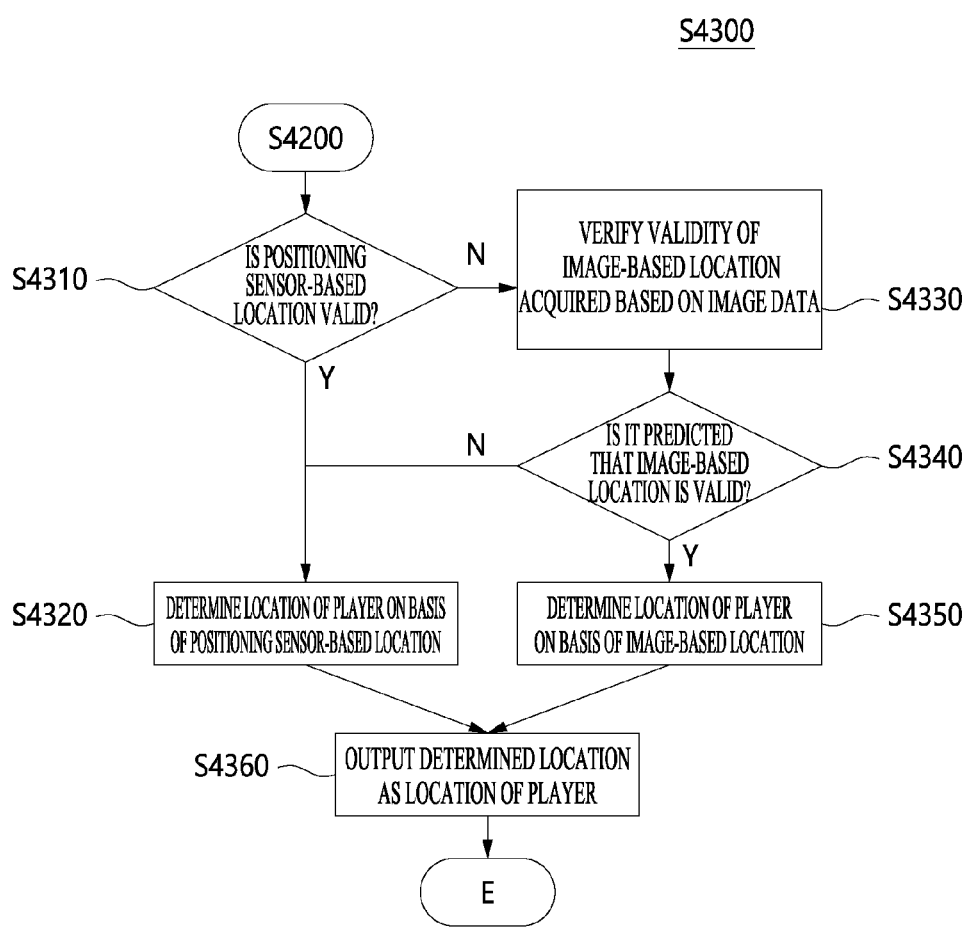
FIG. 21 is a flowchart illustrating the player tracking method according to an embodiment of the present disclosure and is a diagram illustrating operation S4300 of FIG. 20 in detail.

The following description will refer to FIG. 21. FIG. 21 is a flowchart illustrating the player tracking method according to an embodiment of the present disclosure and is a diagram illustrating operation S4300 of FIG. 20 in detail.

Referring to FIG. 21, operation S4300 according to an embodiment of the present disclosure may include determining whether the positioning sensor-based location is valid (S4310), verifying and predicting the validity of the image-based location (S4330 and S4340), determining the player's location on the basis of at least one of the positioning sensor-based location or the image-based location (S4320 or S4350), and outputting the determined location as the player's location (S4360).

In operation S4310, whether the positioning sensor-based location acquired from the positioning sensor data is valid may be determined.

As an example, the above-described player tracking server 1000 may evaluate the validity of the positioning sensor-based location in consideration of reliability-related data of the positioning sensor-based location included in the positioning sensor data. Specifically, reliability-related information (e.g., DoP, SNR) regarding the positioning sensor-based location may be included in the positioning sensor data. In this case, the player tracking server 1000 may evaluate the validity of the positioning sensor-based location in consideration of the reliability-related information acquired from the positioning sensor data and a preset reliability-related threshold value. For example, when the reliability-related information included in the positioning sensor data is greater than the preset threshold value, the player tracking server 1000 may determine that the player's positioning sensor-based location computed from the positioning sensor data is valid. On the other hand, when the reliability-related information included in the positioning sensor data is smaller than the preset threshold value, the player tracking server 1000 may determine that the player's positioning sensor-based location computed from the positioning sensor data is invalid.

As another example, the player tracking server 1000 may evaluate the validity of the positioning sensor-based location in consideration of an internal disparity of the positioning sensor-based location acquired from the positioning sensor data. Specifically, when a change between a positioning sensor-based location corresponding to a first time point and a positioning sensor-based location corresponding to a second time point is greater than a predetermined threshold value, the player tracking server 1000 may determine that the positioning sensor-based location computed from the positioning sensor data corresponding to the second time point is invalid.

As another example, the player tracking server 1000 may evaluate the validity of the positioning sensor-based location in consideration of a difference or disparity between the positioning sensor-based location acquired from the positioning sensor data and the image-based location acquired from the image data. This will be described in detail below with reference to FIG. 22.

In operation S4320, when it is determined by the player tracking server 1000 that the positioning sensor-based location is valid in operation S4310, the location of the sport participant may be determined based on the positioning sensor-based location.

On the other hand, when it is determined by the player tracking server 1000 that the positioning sensor-based location is invalid in operation S4310, the operations of verifying the validity of the image-based location (S4330 and S4340) may be additionally included.

The operation of verifying the validity of the image-based location may include verifying the validity of the image-based location (S4330) and determining whether the image-based location is predicted to be valid (S4340).

In operation S4330, the validity of the image-based location acquired from the image data may be verified in consideration of at least one of the presence of an occlusion event having occurred in the image data, the severity of the occlusion event, the internal disparity of the image-based location acquired from the image data, and a vertical movement of the sport participant.

According to an embodiment, as described above, the player tracking server 1000 may use various methods to detect an occlusion event or determine whether an occlusion event has occurred and may verify or predict the validity of the image-based location on the basis of the occlusion event.

As an example, the player tracking server 1000 may detect an occlusion event or determine whether an occlusion event has occurred in consideration of the degree to which bounding boxes corresponding to sport participants acquired from the image data overlap.

As another example, the player tracking server 1000 may detect an occlusion event or determine whether an occlusion event has occurred in consideration of data on pixels related to the sport participant acquired from the image data.

As another example, the player tracking server 1000 may detect an occlusion event or determine whether an occlusion event has occurred in consideration of locations of the sport participants acquired from the positioning sensor data. Specifically, the player tracking server 1000 may determine that an occlusion event has occurred when a predetermined number or more of sport participants are located in a predetermined region from a positioning sensor-based location corresponding to a specific sport participant.

As another example, the player tracking server 1000 may detect an occlusion event or determine whether an occlusion event has occurred in consideration of locations of the sport participants acquired from the positioning sensor data and data regarding a line-of-sight and an orientation of the image capture device.

In the player tracking method according to an embodiment of the present disclosure, when an occlusion event is detected or when it is determined that an occlusion has occurred, it may be predicted in operation S4340 that the image-based location is invalid.

However, even though an occlusion event is detected or it is determined that an occlusion has occurred, when the severity of the occlusion is not severe, it may be predicted in the operation S4340 that the image-based location is valid. To this end, when an occlusion event has occurred, the validity of the image-based location may be verified or predicted in additional consideration of the severity of the occlusion event.

According to an embodiment, as described above, the player tracking server 1000 may determine the severity of the occlusion event using various methods and may verify or predict the validity of the image-based location.

In the player tracking method according to an embodiment of the present disclosure, when a severe occlusion event is detected or when it is determined that a detected occlusion is severe, it may be predicted in operation S4340 that the image-based location is invalid. On the other hand, when a mild occlusion event is detected or when it is determined that a detected occlusion is mild, it may be predicted in operation S4340 that the image-based location is valid.

According to an embodiment, the player tracking server 1000 may verify or predict the validity of the image-based location in consideration of the image-based location acquired from the image data and a vertical movement of the sport participant at the same time point.

Referring to FIG. 9A again, when there is substantially no vertical movement of a sport participant 1 included in image data, the difference between a location L1_image of the sport participant 1 computed from the image data and an actual location L0 of the sport participant 1 may be relatively small. Therefore, the player tracking server 1000 may predict or determine that the location L1_image of the sport participant 1 acquired from the image data is valid.

On the other hand, referring to FIG. 9B again, when there is substantially a vertical movement of the sport participant 1 included in the image data, the difference between a location L2_image of the sport participant 1 computed from the image data and an actual location L0 of the sport participant 1 may be relatively large. In other words, when there is substantially a vertical movement of the sport participant 1 included in the image data, the location L2_image of the sport participant 1 computed from the image data is likely to have a significant error with respect to the actual location L0. Therefore, the player tracking server 1000 may predict or determine that the location L2_image of the sport participant 1 acquired from the image data is invalid.

In the player tracking method according to an embodiment of the present disclosure, when a vertical movement of the sport participant is detected, it may be predicted in operation S4340 that an image-based location acquired at a time point when the vertical movement is detected is invalid. On the other hand, when no vertical movement of the sport participant is detected, it may be predicted in S4340 that an image-based location is valid.

According to an embodiment, the player tracking server 1000 may verify or predict the validity of the image-based location in consideration of an internal disparity of the image-based location acquired from the image data.

Referring to FIG. 10 again, when the difference between a location Lt1_image of the sport participant computed from a first time point and a location Lt2_image of the sport participant computed from a second time point is greater than a predetermined threshold value, the player tracking server 1000 may determine that the location Lt2_image of the sport participant computed from the second time point is invalid. On the other hand, when the difference between a location Lt3_image of the sport participant computed from a third time point and a location Lt4_image of the sport participant computed from a fourth time point is smaller than the predetermined threshold value, the player tracking server 1000 may determine that the location Lt4_image of the sport participant computed from the fourth time point is valid.

In the player tracking method according to an embodiment of the present disclosure, when the internal disparity of the image-based location is measured to be greater than a predetermined threshold value, it may be predicted in operation S4340 that the image-based location is invalid. On the other hand, when the internal disparity of the image-based location is measured to be smaller than the predetermined threshold value, it may be predicted in operation S4340 that the image-based location is valid.

As described above, when it is predicted in operation S4340 that the image-based location is valid, the player tracking server 1000 may determine the player's location on the basis of the image-based location (S4350).

On the other hand, when it is predicted in operation S4340 that the image-based location is invalid, the player tracking server 1000 may determine the player's location on the basis of the positioning sensor-based location rather than the image-based location (S4320).

FIG. 21 shows that the player tracking server 1000 may determine the player's location on the basis of the positioning sensor-based location rather than the image-based location (S4320) when it is predicted in operation S4340 that the image-based location is invalid, but the present disclosure is not limited thereto. Accordingly, even when it is predicted in operation S4340 that the image-based location is invalid, it is obvious that any suitable method such as the method of determining the player's location may be applied by the player tracking server 1000 in consideration of both of the image-based location and the positioning sensor-based location (e.g., by assigning weight values corresponding to reliability).

In operation S4360, by outputting the determined location of the sport participant, the location of the sport participant may be output or updated. The output location of the sport participant may be a coordinate value corresponding to any suitable coordinate system.

With the above-described player tracking method according to an embodiment according to the present disclosure, by tracking a player on the basis of positioning sensor data first, it is possible to increase data processing efficiency, and it is also possible to facilitate the distinction between sport participants, which are merits of the positioning sensor data. However, in the case of the positioning sensor data, the accuracy of location calculation may change depending on a surrounding structure, and it may be somewhat insufficient for recognizing a behavior or situation of a sport participant. Advantageously, these disadvantages of the positioning sensor data can be compensated for by the image data.

When the location of the sport participant is determined from positioning sensor data acquired from a positioning sensor device, it is easy to distinguish between sport participants, and even at night, it is possible to easily compute the locations of sport participants. Furthermore, the amount of computation is small because the data size is relatively small. Also, conveniently, image capture devices do not have to be installed in advance near a playfield or the like.

When a location of a sport participant is determined from image data acquired from an image capture device, it is possible to accurately measure the location of the sport participant, and the influence of structures near a playfield is relatively small. Furthermore, it is relatively easy to recognize or analyze the sport participant's motion, and it is possible to provide convenient use indoors. Also, conveniently, the sport participant does not need to wear a positioning sensor device.

Therefore, with the player tracking method according to an embodiment of the present disclosure, by determining a location of a sport participant in consideration of both of positioning sensor data and image data, it is possible to utilize advantages of both of the positioning sensor data and the image data. Also, by determining a location of a sport participant by generating and comparing reliability indices of a positioning sensor-based location and an image-based location, it is possible to more accurately track the sport participant.

The player tracking method according to an embodiment of the present disclosure may be implemented by the player tracking system 100 shown in FIG. 3. Also, the player tracking method according to an embodiment of the present disclosure may be implemented by the player tracking server 1000 shown in FIG. 4.

The player tracking server 1000 according to an embodiment of the present disclosure may generate a reliability index related to the image-based location and a reliability index related to the positioning sensor-based location. The player tracking server 1000 may be provided to generate the reliability index related to the image-based location and the reliability index related to the positioning sensor-based location.

Specifically, the player tracking server 1000 may generate a reliability index for reliability related to a positioning sensor-based location acquired from positioning sensor data. Specifically, the player tracking server 1000 may generate the reliability index for the positioning sensor-based location on the basis of a result of evaluating the validity of the positioning sensor-based location.

As an example, information (e.g., DoP, SNR) related to the reliability of a sensor signal may be included in the positioning sensor data. In this case, the player tracking server 1000 may evaluate the validity of the positioning sensor-based location on the basis of the information (e.g., DoP, SNR) related to the reliability of the sensor signal, and the player tracking server 1000 may generate the reliability index for the positioning sensor-based location in consideration of the information (e.g., DoP, SNR) related to the reliability of the sensor signal on the basis of the evaluation.

As another example, the player tracking server 1000 may evaluate the validity of the positioning sensor-based location on the basis of the internal disparity of the positioning sensor-based location computed from the positioning sensor data. In this case, the player tracking server 1000 may generate the reliability index for the positioning sensor-based location on the basis of a result of evaluating the validity of the positioning sensor-based location based on the internal disparity of the positioning sensor-based location.

Also, the player tracking server 1000 may generate a reliability index for reliability related to an image-based location acquired from image data. Specifically, the player tracking server 1000 may generate the reliability index for the image-based location on the basis of a result of evaluating the validity of the image-based location.

As an example, the player tracking server 1000 may evaluate the validity of the image-based location acquired from the image data according to whether an occlusion event is detected. In this case, the player tracking server 1000 may generate the reliability index for the image-based location on the basis of a result of evaluating the validity of the image-based location according to whether an occlusion event is detected.

As another example, the player tracking server 1000 may evaluate the validity of the image-based location acquired from the image data in consideration of a vertical movement of the sport participant. In this case, the player tracking server 1000 may generate the reliability index for the image-based location on the basis of a result of evaluating the validity of the image-based location in consideration of the vertical movement of the sport participant.

As another example, the player tracking server 1000 may evaluate the validity of the image-based location on the basis of the internal disparity of the image-based location computed from the image data. In this case, the player tracking server 1000 may generate the reliability index for the image-based location on the basis of a result of evaluating the validity of the image-based location based on the internal disparity of the image-based location.

In this case, the player tracking server 1000 may determine the location of the sport participant by comparing the generated reliability index for the positioning sensor-based location and the generated reliability index for the image-based location.

Here, in order to compare the reliability index for the positioning sensor-based location and the reliability index for the image-based location, standardization is required between the reliability indices. Therefore, the player tracking server 1000 according to an embodiment of the present disclosure may perform the standardization between the reliability index related to the image-based location and the reliability index related to the positioning sensor-based location. The player tracking server 1000 may perform the standardization with respect to the reliability index related to the image-based location and the reliability index related to the positioning sensor-based location.

The standardization of the reliability indices by the player tracking server 1000 may be for correcting or standardizing the reliability indices using any suitable statistical method or standardization model to compare the reliability index related to the image-based location and the reliability index related to the positioning sensor-based location.

Figure 22:
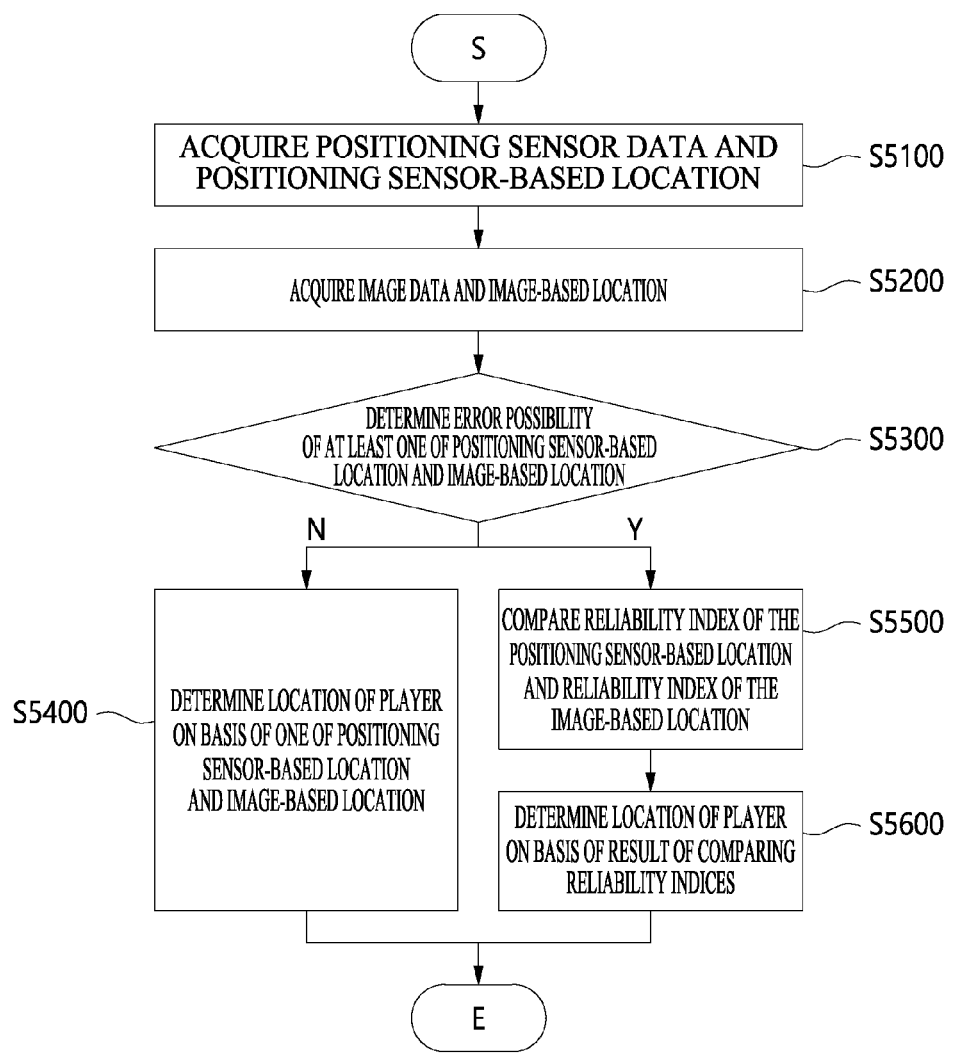
FIG. 22 is a flowchart illustrating a player tracking method according to an embodiment of the present disclosure.

The following description will refer to FIG. 22. FIG. 22 is a flowchart illustrating a player tracking method according to an embodiment of the present disclosure.

Referring to FIG. 22, the player tracking method according to an embodiment of the present disclosure may include acquiring positioning sensor data and a positioning sensor-based location (S5100), acquiring image data and an image-based location (S5200), determining an error possibility of at least one of the positioning sensor-based location and the image-based location (S5300), and determining a player's location (S5400, S5500, and S5600). In this case, the operation of determining a player's location may include comparing reliability indices of the positioning sensor-based location and the image-based location (S5500) and determining the player's location (S5600) and determining the player's location on the basis of one of the positioning sensor-based location and the image-based location (S5400), depending on a result of determining the error possibility in operation S5300.

In operation S5100, positioning sensor data transmitted from the positioning sensor device 210 or 220 may be acquired. Also, a positioning sensor-based location may be acquired from the positioning sensor data. The positioning sensor-based location may be acquired from location-related data included in the positioning sensor data or may be acquired from velocity- or acceleration-related data included in the positioning sensor data.

In operation S5200, image data transmitted from the image capture device 300 may be acquired. Also, an image-based location may be acquired from the image data. The image-based location may be acquired from a coordinate value of a pixel corresponding to a location of a sport participant included in the image data.

In operation S5300, it may be determined whether the positioning sensor-based location acquired in operation S5100 is valid and whether the image-based location acquired in operation S5200 is valid. Therefore, the embodiments of the player tracking server 1000 that determines the validity of the image-based location and the positioning sensor-based location, which have been described with reference to FIGS. 5 to 12, may be implemented in operation S5400.

According to an embodiment, in operation S5300, an error possibility of at least one of the positioning sensor-based location and the image sensor-based location may be determined.

As an example, the error possibility of at least one of the positioning sensor-based location and the image-based location may be determined in consideration of the difference between the positioning sensor-based location and the image-based location.

For example, the player tracking server 1000 may compute a disparity index between the image-based location of the sport participant acquired from the image data and the positioning sensor-based location of the sport participant acquired from the positioning sensor data according to a time variable. In this case, the player tracking server 1000 may determine the validity of at least one of the image-based location and the positioning sensor-based location on the basis of the disparity index.

Specifically, the player tracking server 1000 may compute a first disparity index corresponding to the difference between a first image-based location and a first positioning sensor-based location which are acquired at a first time point. Also, the player tracking server 1000 may compute a second disparity index corresponding to the difference between a second image-based location and a second positioning sensor-based location which are acquired at a second time point.

In this case, the player tracking server 1000 may evaluate the validity of at least one of the positioning sensor-based location (e.g., the first positioning sensor-based location and the second positioning sensor-based location) and the image-based location (e.g., the first image-based location and the second image-based location) in consideration of the size of the first disparity index and the size of the second disparity index. For example, when the first disparity index exceeds a predetermined first threshold value, the player tracking server 1000 may determine that an error is present in at least one of the first image-based location and the first positioning sensor-based location acquired at the first time point. On the other hand, when the second disparity index is less than a predetermined second threshold value, the player tracking server 1000 may determine that one or both of the second image-based location and the second positioning sensor-based location acquired at the second time point are valid. In this case, the first threshold value and the second threshold value may be the same value or may be predetermined to be different values.

Also, the player tracking server 1000 may evaluate the validity of at least one of the positioning sensor-based location (e.g., the first positioning sensor-based location and the second positioning sensor-based location) and the image-based location (e.g., the first image-based location and the second image-based location) in consideration of a change in the first disparity index and a change in the second disparity index.

For example, when the variations of the first disparity index and the second disparity index exceed a predetermined third threshold value (preferably, when it is determined that the first image-based location and the first positioning sensor-based location which are related to the first disparity index are valid), the player tracking server 1000 may determine that an error is present in at least one of the second image-based location and the second positioning sensor-based location acquired at the second time point. On the other hand, when the variations of the first disparity index and the second disparity index are less than a predetermined fourth threshold value (preferably, when it is determined that the first image-based location and the first positioning sensor-based location which are related to the first disparity index are valid), the player tracking server 1000 may determine that one or both of the second image-based location and the second positioning sensor-based location acquired at the second time point are valid. In this case, the third threshold value and the fourth threshold value may be the same value or may be predetermined to be different values.

The above-described determination of the error possibility of at least one of the image-based location and the positioning sensor-based location in consideration of the difference between the image-based location and the positioning sensor-based location is just an example, and the validity of the image-based location or the positioning sensor-based location may be determined using any suitable method considering the difference between the image-based location and the positioning sensor-based location.

When it is determined in operation S5300 that there is no error possibility of at least one of the positioning sensor-based location and the image-based location, that is, when it is determined that both of the positioning sensor-based location and the image-based location are valid, the player tracking server 1000 may determine the location of the sport participant on the basis of one of the positioning sensor-based location and the image-based location in operation S5400.

Alternatively, since the positioning sensor-based location and the image-based location have a small error possibility, the player tracking server 1000 may determine the location of the sport participant in consideration of both of the positioning sensor-based location and the image-based location. For example, the player tracking server 1000 may determine the location of the sport participant using the average of the positioning sensor-based location and the image-based location. Alternatively, the player tracking server 1000 may determine the location of the sport participant in consideration of the reliability index of the positioning sensor-based location and the reliability index of the image-based location.

When it is determined in operation S5300 that there is an error possibility of at least one of the positioning sensor-based location and the image-based location, that is, when it is determined that at least one of the positioning sensor-based location and the image-based location is invalid, an operation of comparing the first reliability index for the positioning sensor-based location and the second reliability index of the image-based location may be performed by the player tracking server 1000 in operation S5500.

Specifically, the player tracking server 1000 may generate the first reliability index for the positioning sensor-based location in consideration of reliability-related information included in the positioning sensor data. Alternatively, the player tracking server 1000 may generate the first reliability index for the positioning sensor-based location on the basis of a result of determining the validity of the positioning sensor-based location based on the internal disparity of the positioning sensor-based location.

Also, the player tracking server 1000 may generate the second reliability index for the image-based location on the basis of a result of determining the validity of the image-based location based on at least one of an occlusion event related to the image-based location, a vertical movement of the sport participant, and an internal disparity of the sport participant.

Also, the player tracking server 1000 may standardize the first reliability index and the second reliability index.

In this case, in operations S5500 and S5600, the player tracking server 1000 may determine the location of the sport participant by comparing the first reliability index for the positioning sensor-based location and the second reliability index for the image-based location.

As an example, the player tracking server 1000 may determine the location of the sport participant on the basis of a location corresponding to the higher one of the first reliability index and the second reliability index.

For example, when the first reliability index is larger than the second reliability index, that is, when a positioning sensor-based location corresponding to the first reliability index has relativity high reliability, the player tracking server 1000 may determine the location of the sport participant on the basis of the positioning sensor-based location.

As another example, when the second reliability index is greater than the first reliability index, that is, when an image-based location corresponding to the second reliability index has relatively high reliability, the player tracking server 1000 may determine the location of the sport participant on the basis of the image-based location.

As another example, the player tracking server 1000 may determine the location of the sport participant by assigning appropriate weight values to the positioning sensor-based location and the image-based location in consideration of the first reliability index and the second reliability index.

For example, when the first reliability index is greater than the second reliability index, the player tracking server 1000 may determine the location of the sport participant by assigning a relatively high weight value to the positioning sensor-based location.

For example, when the second reliability index is greater than the first reliability index, the player tracking server 1000 may determine the location of the sport participant by assigning a relatively high weight value to the image-based location.

For example, when the first reliability index is similar or substantially identical to the second reliability index, the player tracking server 1000 may determine the location of the sport participant by assigning similar weight values (e.g., a 1:1 weighted average) to the positioning sensor-based location and the image-based location.

With the above-described player tracking method according to an embodiment of the present disclosure, by determining an error possibility of at least one of the positioning sensor-based location and the image-based location, it is possible to accurately measure the location of the sport participant.

Also, even when at least one of the positioning sensor-based location and the image-based location may have an error, the reliability of the positioning sensor-based location and the image-based location may be evaluated. Thus, even in this case, it is possible to accurately measure the location of the sport participant.

As described above, although the description was focused on determining the validity in consideration of the difference between the image-based location and the positioning sensor-based location in operation S5300, this is just an example. The operation, which is related to FIGS. 5 to 12, of determining the validity of the image-based location and the positioning sensor-based location may be equally applied.

In acquiring the location of the sport participant, the accuracy of the location of the sport participant may change depending on the region of the playfield where the sport participant is located. In other words, the reliability of the acquired location may change depending on the region of the playfield where the sport participant is located. This is because reliability related to a sensor signal or image data may change for each region of the playfield where the sport participant is located.

For example, the reliability of the location of the sport participant acquired from the positioning sensor data may be affected by the structure or shape of a stadium near the playfield where the sport participant is located. Therefore, since the degree to which the influence of the structure or shape of the stadium may be different for each region of the playfield, the reliability of the location of the sport participant acquired from the positioning sensor data may be different for each region of the playfield.

Also, the reliability of the location of the sport participant acquired from the image data may be affected by factors such as the location, angle, lens distortion, and the like of the image capture device. Therefore, the reliability of the location of the sport participant acquired from the image capture device may be different for each region of the playfield.

Therefore, the play tracking method according to another embodiment of the present disclosure may generate a reliability map for each region of the playfield and use reliability information corresponding to a playfield region where the sport participant is located. Therefore, with the play tracking method according to an embodiment of the present disclosure, it is possible to more accurately acquire the location of the sport participant.

The player tracking method according to an embodiment of the present disclosure may be implemented by the player tracking system 100 shown in FIG. 3. Also, the player tracking method according to an embodiment of the present disclosure may be implemented by the player tracking server 1000 shown in FIG. 4.

The player tracking server 1000 according to an embodiment of the present disclosure may generate a reliability index for each region of the playfield related to the image-based location and a reliability index for each region of the playfield related to the positioning sensor-based location. Also, the player tracking server 1000 may generate reliability maps on the basis of the reliability index for each region of the playfield related to the image-based location and the reliability index for each region of the playfield related to the positioning sensor-based location. Specifically, the player tracking server 1000 may be provided to generate reliability maps on the basis of the reliability index for each region of the playfield related to the image-based location and the reliability index for each region of the playfield related to the positioning sensor-based location.

For each region of the playfield, the player tracking server 1000 may generate a reliability index related to the location of the sport participant acquired from the image data. In this case, the player tracking server 1000 may generate the reliability index for the image-based location for each region of the playfield in consideration of the location of the sport participant on the playfield and a result of evaluating the validity of the image-based location.

The details described above with reference to FIGS. 5 to 10 may be similarly applied to the determination of the validity of the image-based location.

For each region of the playfield, the player tracking server 1000 may generate a reliability index related to the location of the sport participant acquired from the positioning sensor data. In this case, the player tracking server 1000 may generate the reliability index for the positioning sensor-based location for each region of the playfield in consideration of the location of the sport participant on the playfield and a result of evaluating the validity of the positioning sensor-based location.

The details described above with reference to FIGS. 11 and 12 may be similarly applied to the determination of the validity of the positioning sensor-based location.

Also, the player tracking server 1000 may be provided to standardize the reliability index related to the image-based location and the reliability index related to the positioning sensor-based location. The standardization of the reliability indices by the player tracking server 1000 may be for correcting or standardizing the reliability index related to the image-based location and the reliability index related to the positioning sensor-based location using any suitable statistical method or standardization model to compare the reliability indices.

Also, the player tracking server 1000 may generate a first reliability map on the basis of the generated and standardized reliability index for each region of the playfield related to the positioning sensor-based location. In this case, the first reliability map may include information on a reliability index related to a positioning sensor-based location acquired according to a region of the playfield.

Figure 23:
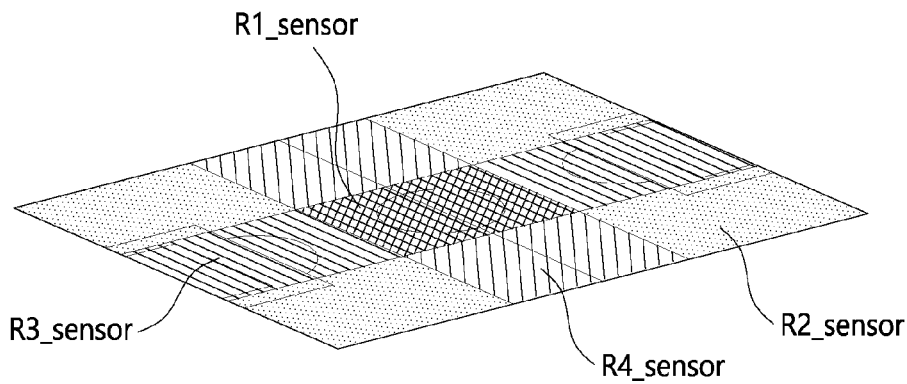
FIG. 23 is an example diagram of a first reliability map according to an embodiment of the present disclosure.

The following description will refer to FIG. 23. FIG. 23 is an example diagram of the first reliability map according to an embodiment of the present disclosure. Referring to FIG. 23, the first reliability map may include reliability information related to the positioning sensor-based location.

A plurality of regions including a first region R1_sensor, a second region R2_sensor, a third region R3_sensor, and a fourth region R4_sensor included in the first reliability map may be regions corresponding to a plurality of regions of the playfield.

Also, the reliability information related to the positioning sensor-based location may be different for each of the plurality of regions included in the first reliability map.

As an example, reliability information related to the first region R1_sensor of the first reliability map may have a relatively high value. For example, considering the structure of the stadium near the playfield, a sensor signal with high reliability may be received when a sport participant is located in the center of the playfield corresponding to the first region R1_sensor.

As another example, reliability information related to the second region R2_sensor of the first reliability map may have a relatively low value. For example, considering the structure of the stadium near the playfield, a sensor signal with relatively low reliability may be received when a sport participant is located at a corner of the playfield corresponding to the second region R2_sensor because the sensor signal may be affected by the structure of the stadium.

As another example, reliability information related to the third region R3_sensor or the fourth region R4_sensor of the first reliability map may have a value lower than reliability related to the first region R1_sensor and higher than reliability related to the second region R2_sensor.

However, the above-described reliability for each region of the first reliability map is just an example for convenience of description, and it is obvious that the reliability for each region may vary depending on the structure and shape of the stadium.

Also, the player tracking server 1000 may generate a second reliability map on the basis of the generated and standardized reliability index for each region of the playfield related to the image-based location.

In this case, the second reliability map may include information on a reliability index related to an image-based location acquired according to a region of the playfield.

Figure 24:
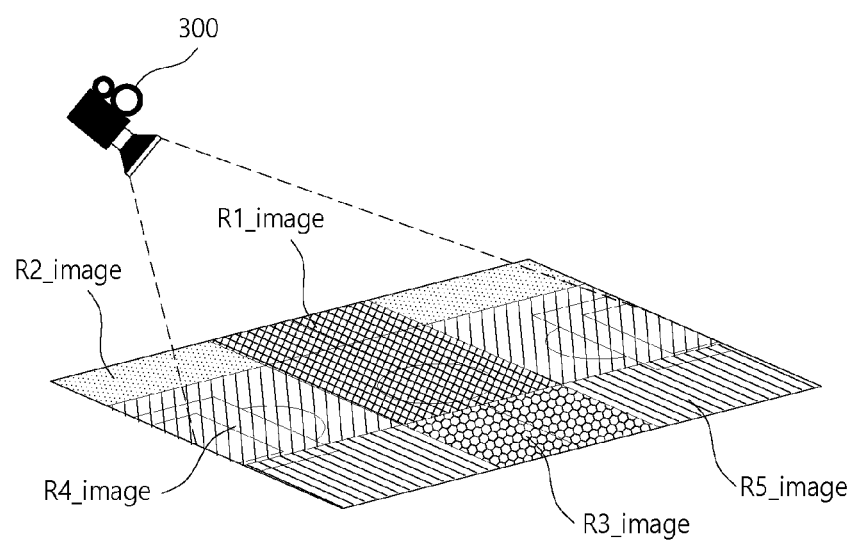
FIG. 24 is an example diagram of a second reliability map according to an embodiment of the present disclosure.

The following description will refer to FIG. 24. FIG. 24 is an example diagram of the second reliability map according to an embodiment of the present disclosure. Referring to FIG. 24, the second reliability map may include reliability information related to the image-based location.

A plurality of regions including a first region R1_image, a second region R2_image, a third region R3_image, a fourth region R4_image, and a fifth region R5_image included in the second reliability map may be regions corresponding to a plurality of regions of the playfield.

Also, the reliability information related to the image-based location may be different for each of the plurality of regions included in the second reliability map.

As an example, reliability information related to the first region R1_image of the second reliability map may have a relatively high value. For example, considering an orientation, which includes a location and an angle, of the image capture device 300, image data with relatively low distortion may be acquired when a sport participant is located in the region of the playfield corresponding to the first region R1_image. Therefore, when a sport participant is located in the region of the playfield corresponding to the first region R1_image, the image-based location acquired from the image data may have relatively high reliability.

As another example, reliability information related to the second region R2_image of the second reliability map may have a relatively low value. For example, considering an orientation, which includes a location and an angle, of the image capture device 300, image data with relatively large distortion may be acquired when a sport participant is located in the region of the playfield corresponding to the second region R2_image. Therefore, when a sport participant is located in the region of the playfield corresponding to the second region R2_image, the image-based location acquired from the image data may have relatively low reliability.

As another example, considering an orientation, which includes a location and an angle, of the image capture device 300, reliability information related to the third region R3_image, the fourth region R4_image, or the fifth region R5_image of the second reliability map may have a value lower than reliability related to the first region R1_image of the second reliability map and higher than reliability related to the second region R2_image.

However, the above-described reliability for each region of the second reliability map is just an example for convenience of description, and it is obvious that the reliability for each region may vary depending on an arrangement, a number, lens distortion, and the like related to the location and orientation of the image capture device 300.

Figure 25:
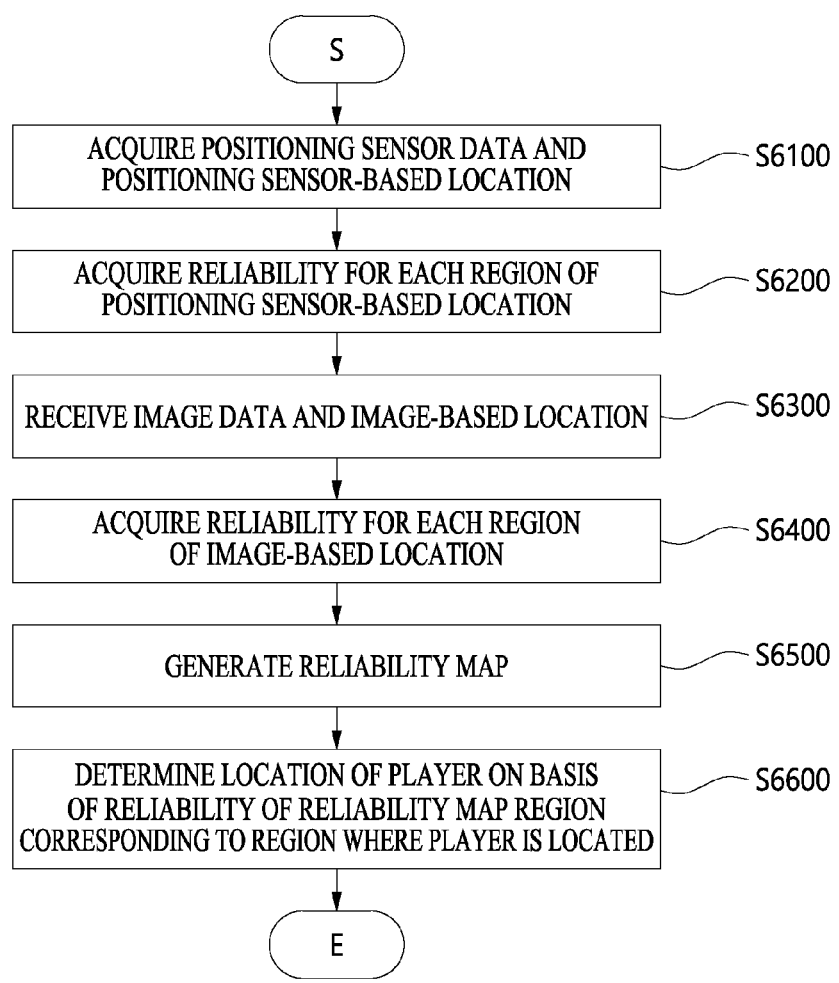
FIG. 25 is a flowchart illustrating a player tracking method according to an embodiment of the present disclosure.

The following description will refer to FIG. 25. FIG. 25 is a flowchart illustrating a player tracking method according to an embodiment of the present disclosure.

Referring to FIG. 25, the player tracking method according to an embodiment of the present disclosure may include acquiring positioning sensor data and a positioning sensor-based location (S6100), acquiring reliability for each region of the positioning sensor-based location (S6200), acquiring image data and an image-based location (S6300), acquiring reliability for each region of the image-based location (S6400), generating a reliability map (S6500), and determining a player's location on the basis of the reliability of a reliability map region (S6600).

In operation S6100, positioning sensor data transmitted from the positioning sensor device 210 or 220 may be acquired. Also, a positioning sensor-based location may be acquired from the positioning sensor data. The positioning sensor-based location may be acquired from location-related data included in the positioning sensor data or may be acquired from velocity- or acceleration-related data included in the positioning sensor data.

In operation S6200, reliability for each region of the positioning sensor-based location may be acquired.

In this case, the reliability for each region of the positioning sensor-based location may be generated by the player tracking server 1000. For example, as described above, the player tracking server 1000 may generate, for each region of the playfield, a reliability index related to the location of the sport participant acquired from the positioning sensor data. In this case, the player tracking server 1000 may generate the reliability index for the positioning sensor-based location for each region of the playfield in consideration of the location of the sport participant on the playfield and a result of evaluating the validity of the positioning sensor-based location.

Also, the reliability for each region of the positioning sensor-based location may be a reliability index standardized by the player tracking server 1000.

The player tracking server 1000 may generate a reliability map related to the positioning sensor-based location on the basis of the acquired reliability for each region of the positioning sensor-based location.

In operation S6300, image data transmitted from the image capture device 300 may be acquired. Also, an image-based location may be acquired from the image data. The image-based location may be acquired from a coordinate value of a pixel corresponding to a location of a sport participant included in the image data.

In operation S6400, reliability for each region of the image-based location may be acquired.

In this case, the reliability for each region of the image-based location may be generated by the player tracking server 1000. For example, as described above, the player tracking server 1000 may generate, for each region of the playfield, a reliability index related to the location of the sport participant acquired from the image data. In this case, the player tracking server 1000 may generate the reliability index for the image-based location for each region of the playfield in consideration of the location of the sport participant on the playfield and a result of evaluating the validity of the image-based location.

Also, the reliability for each region of the image-based location may be a standardized reliability index.

The player tracking server 1000 may generate a reliability map related to the image-based location on the basis of the acquired reliability for each region of the image-based location.

In operation S6500, the player tracking server 1000 may generate the first reliability map related to the positioning sensor-based location and the second reliability map related to the image-based location in consideration of the reliability for each region of the positioning sensor-based location and the reliability for each region of the image-based location.

It has been described that the player tracking server 1000 generates the first reliability map related to the positioning sensor-based location and the second reliability map related to the image-based location, but this is just an example. The player tracking server 1000 may generate a single reliability map in consideration of both of the reliability for each region of the positioning sensor-based location and the reliability for each region of the image-based location.

In operation S6600, the player tracking server 1000 may determine the location of the sport participant in consideration of the reliability information included in the first reliability map related to the positioning sensor-based location and the second reliability map related to the image-based location, which are generated in operation S6500.

To this end, locations of the sport participant corresponding to the region of the first reliability map and the region of the second reliability map should be additionally considered.

Therefore, additionally, the player tracking server 1000 may be implemented to further acquire information regarding a region of the playfield where the sport participant is located.

For example, the player tracking server 1000 may acquire data related to the location of the sport participant from the positioning sensor data, and the player tracking server 1000 may detect the region of the playfield where the sport participant is located on the basis of data related to the location of the sport participant included in the positioning sensor data.

As another example, the player tracking server 1000 may acquire data related to the location of the sport participant from the image data, and the player tracking server 1000 may detect the region of the playfield where the sport participant is located on the basis of data related to the location of the sport participant included in the image data.

The player tracking server 1000 may determine the location of the sport participant by sequentially considering the first reliability information of the first reliability map region and the second reliability information of the second reliability map region corresponding to the detected region where the sport participant is located.

As an example, the player tracking server 1000 may determine the location of the sport participant in consideration of a location acquired from data having the higher one of the first reliability information and the second reliability information.

For example, when a sport participant is located in a region where the first reliability information is higher than the second reliability information, the player tracking server 1000 may determine the location of the sport participant on the basis of the positioning sensor-based location.

As another example, when a sport participant is located in a region where the second reliability information is higher than the first reliability information, the player tracking server 1000 may determine the location of the sport participant on the basis of the image-based location.

As another example, the player tracking server 1000 may determine the location of the sport participant by assigning weight values according to the first reliability information and the second reliability information.

For example, when a sport participant is located in a region where the first reliability information is higher than the second reliability information, the player tracking server 1000 may determine the location of the sport participant by assigning a higher weight value to the positioning sensor-based location than to the image-based location.

As another example, when a sport participant is located in a region where the second reliability information is higher than the first reliability information, the player tracking server 1000 may determine the location of the sport participant by assigning a higher weight value to the image-based location than to the positioning sensor-based location.

The above-described reliability map may be generated or updated during a sport game in real time. However, this is just an example, and reliability maps related to the image-based location and the positioning sensor-related location may be pre-generated even before a sport game.

In the above, an embodiment in which an image-based location is acquired from at least one image capture device and the accuracy of the location of the sport participant is increased by additionally considering the positioning sensor-based location has been described.

A player tracking method, a player tracking device, and a player tracking system that increase the accuracy of a location of a sport participant on the basis of a plurality of pieces of image data acquired from a plurality of image capture devices will be described in detail below. Although the description was focused on the player tracking system 100 according to this embodiment increasing the accuracy of the location of the sport participant on the basis of a plurality of pieces of image data acquired from a plurality of image capture devices, it is obvious that the positioning sensor-based location can be additionally considered in combination.

Figure 26:
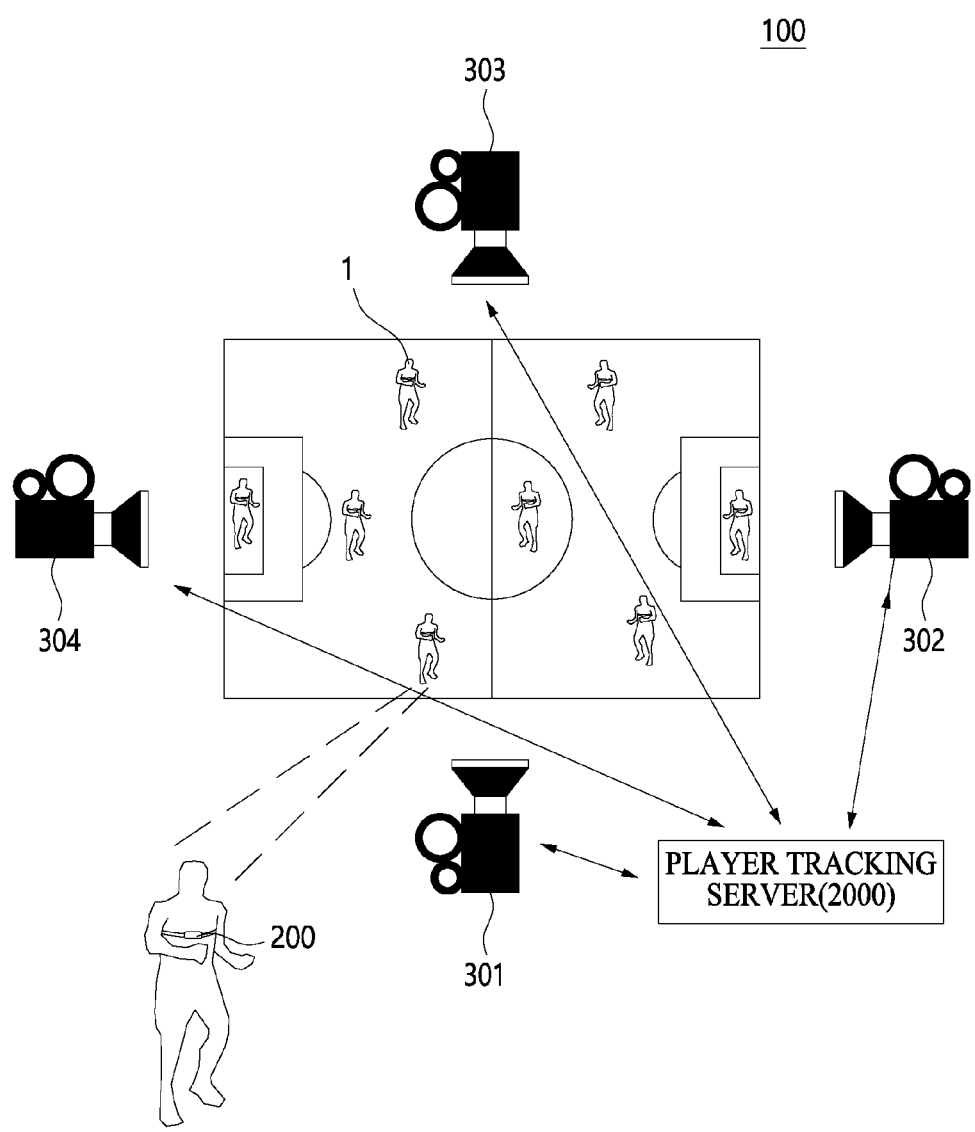
FIG. 26 is a schematic diagram showing a player tracking system utilizing a plurality of image capture devices according to an embodiment of the present disclosure.

FIG. 26 is a schematic diagram illustrating the player tracking device, the player tracking system, and the player tracking method according to an embodiment of the present disclosure.

Referring to FIG. 26, with the player tracking method, the player tracking device, and the player tracking system according to an embodiment of the present disclosure, a player's location may be tracked using image data acquired from a plurality of image capture devices.

A player tracking system 100 according to an embodiment of the present disclosure will be described below with reference to FIG. 26.

Referring to FIG. 26, the player tracking system 100 may include a plurality of image capture devices 301, 302, 303, and 304, a positioning sensor device 200, and a player tracking server 2000. Meanwhile, FIG. 26 does not show the intermediate server 400 or the playfield shown in FIG. 3, but this is for convenience of description, image data or positioning sensor data may be acquired through the intermediate server 400 of the player tracking system 100 of FIG. 3.

The plurality of image capture devices 301, 302, 303, and 304 of the player tracking system 100 may capture a playfield and a sport participant 1, and the player tracking device 2000 may continuously track the location of the sport participant 1 by determining the location of the sport participant 1 on the basis of image data acquired from the plurality of image capture devices 301, 302, 303, and 304.

Referring to FIG. 26, the plurality of image capture devices 301, 302, 303, and 304 may be located around the playfield. The plurality of image capture devices 301, 302, 303, and 305 may capture image data including the playfield and a plurality of sport participants 1 and transmit the image data to the player tracking device 2000 according to an embodiment of the present disclosure.

The plurality of image capture devices 301, 302, 303, and 304 may be arranged at different locations around the playfield as shown in FIG. 26. However, this is just an example, and the plurality of image capture devices 301, 302, 303, and 304 may be arranged at substantially the same place or adjacent locations near the playfield. Also, it is obvious that the plurality of image capture devices 301, 302, 303, and 304 may be arranged at any suitable location in various ways.

In this case, the player tracking device 2000 may additionally acquire, from a plurality of image capture devices, data related to lens distortion parameters of the plurality of image capture devices and arrangement information related to the locations and orientations of the plurality of image capture devices. Thus, image data that allows a target sport participant to be detected well or that allows a location of a target sport participant to be accurately acquired may be selected. This will be described in detail with reference to FIGS. 27 and 28.

In this case, the image data acquired from the plurality of image capture devices may be labeled with information regarding the image capture devices and transmitted to the player tracking device 2000. For example, any suitable labeling technique may be applied to include any suitable data indicating that the first image data acquired from the first image capture device 301 is captured from the first image capture device 301. Also, any suitable labeling technique may be applied to include any suitable data indicating that the second image data acquired from the second image capture device 302 is captured from the second image capture device 302. Thus, an image capture device capable of acquiring image data that allows a target sport participant to be detected well or that allows a location of a target sport participant to be accurately acquired may be determined to track the sport participant through an occlusion prediction. This will be described in detail with reference to FIGS. 29 and 30.

In this case, a plurality of sport participants 1 may wear a positioning sensor device 200, and the player tracking server 2000 may acquire positioning sensor data as described above with reference to FIG. 3. The positioning sensor data related to the plurality of sport participants 1 may be considered in detecting the presence of an occlusion, in generating a virtual playfield, or in detecting an occlusion. This will be described in detail with reference to FIGS. 27 to 31.

The player tracking device 2000 may be implemented as a server device of any suitable type. Hereinafter, the player tracking device 2000 is referred to as the player tracking server 2000. However, this is just for convenience of description, and the player tracking device 2000 is not necessarily implemented in the form of a server.

The player tracking server 2000 according to an embodiment of the present disclosure will be described below.

According to an embodiment of the present disclosure, the player tracking server 2000 may acquire a plurality of pieces of image data from a plurality of image capture devices 301, 302, 303, and 304 in order to determine the location of the sport participant. Also, the player tracking server 2000 may select an image including a target sport participant to be tracked from among the plurality of pieces of image data as a candidate image. Also, the player tracking server 2000 may select a valid image from a plurality of acquired candidate images in consideration of an occlusion event. Also, the player tracking server 2000 may determine the location of the target sport participant from the selected valid image.

The details described with reference to FIG. 4 may be equally applied to the player tracking server 2000 according to an embodiment of the present disclosure. That is, the player tracking server 2000 may include a communication module 1100, a memory 1200, and a controller 1300. In particular, the details described with reference to FIG. 4 may be equally applied to the communication module 1100, the memory 1200, and the controller 1300, and thus a detailed description thereof will be omitted. Therefore, the following description will focus on details added to the player tracking server 2000.

Some operations performed by an example of the player tracking system 100 in association with the player tracking method will be described in detail below.

The player tracking system 100 according to this embodiment may acquire a plurality of pieces of image data from a plurality of image capture devices. Specifically, the player tracking server 2000 may acquire a plurality of pieces of image data captured by a plurality of image capture devices.

The player tracking system 100 according to an embodiment of the present disclosure may select a candidate image from the plurality of pieces of image data. Specifically, the player tracking server 2000 may be implemented to detect a target sport participant to be tracked in each of the plurality of pieces of image data acquired from the plurality of image capture devices 301, 302, 303, and 304. Specifically, the plurality of pieces of image data may include data (e.g., pixels) corresponding to a plurality of sport participants. In this case, the player tracking server 2000 may be implemented to recognize the sport participants in consideration of the data corresponding to the plurality of sport participants and may detect a target sport participant in additional consideration of data related to identifiers corresponding to the recognized sport participants.

Also, the player tracking server 2000 may be implemented to select at least one candidate image from the plurality of pieces of image data according to a result of detecting the target sport participant. For example, the player tracking server 2000 may be implemented to select image data in which the target sport participant is detected from among the plurality of pieces of image data as a candidate image. The candidate image may include at least one candidate image.

The player tracking system 100 according to an embodiment of the present disclosure may be implemented to select a valid image that may be considered in determining the location of the target sport participant. Specifically, the player tracking server 2000 may be implemented to select a valid image that may be considered in determining the location of the target sport participant from among the at least one selected candidate image.

Here, the valid image may be used in the sense of encompassing an image that may be considered in determining the location of the target sport participant. For example, an image in which the target sport participant is detected may be a valid image. However, according to a preferred embodiment, in order to more accurately determine the location of the target sport participant, the valid image may be defined as an image in which no occlusion event is detected in relation to the target sport participant or an image in which an occlusion event is detected but the severity of the occlusion event is not severe.

As an example, the player tracking server 2000 may select at least one valid image from among the at least one candidate image in consideration of whether an occlusion event has occurred in the plurality of pieces of image data or a result of determining whether an occlusion event has occurred.

For example, the player tracking server 2000 may be implemented to select, as valid images, candidate images in which an occlusion event related to a target sport participant is not detected.

As another example, the player tracking server 2000 may be implemented to select, as valid images, mild candidate images in which an occlusion event related to a target sport participant is detected but the severity of the occlusion event is not severe.

As another example, the player tracking server 2000 may be implemented to select valid images from among candidate images in which an occlusion event related to a target sport participant is detected in consideration of whether the target sport participant hides or is hidden by another sport participant.

Specifically, even though an occlusion event related to a target sport participant is detected in a first candidate image, the determination of the location of the target sport participant from the first candidate image may have relatively high accuracy when the occlusion event is detected by means of the target sport participant hiding another sport participant.

On the other hand, even though an occlusion event related to a target sport participant is detected in a second candidate image, the determination of the location of the target sport participant from the second candidate image may be relatively difficult when the occlusion event is detected by means of the target sport participant being hidden by another sport participant. Also, the location of the target sport participant acquired from the second candidate image may have relatively low accuracy.

Therefore, the player tracking server 2000 may be implemented to select a valid image in consideration of whether the occlusion event is detected in the candidate image by means of the target sport participant hiding or being hidden by another sport participant. Preferably, the operation of the player tracking server 2000 may be advantageous when the occlusion event related to the target sport participant is detected in most or all of the candidate images.

As another example, the player tracking server 2000 may be implemented to select valid images in consideration of arrangement information related to the location and orientations of the plurality of image capture devices 301, 302, 303, and 304. Specifically, the plurality of image capture devices 301, 302, 303, and 304 may be placed in any suitable arrangement at different locations around the playfield. In this case, the player tracking server 2000 may be implemented to select, as a valid image, image data in which the target sport participant is largest or image data in which the target sport participant is located closest to the center from among the plurality of pieces of image data acquired from the plurality of image capture devices 301, 302, 303, and 304 in consideration of the arrangement information of the plurality of image capture devices 301, 302, 303, and 304.

As another example, the player tracking server 2000 may be implemented to select a valid image in consideration of a lens distortion parameter. Specifically, there is a high possibility that a relatively small amount of distortion occurs at the center of the image data when the lens distortion parameter is considered. Accordingly, when the location of the target sport participant is computed from image data where the target sport participant is located at the center of the image data, the accuracy of the location may be relatively high. On the other hand, there is a high possibility that a relatively large amount of distortion occurs at the edge of the image data when the lens distortion parameter is considered. Accordingly, when the location of the target sport participant is computed from image data where the target sport participant is located at the edge of the image data, the accuracy of the location may be relatively low. Accordingly, the player tracking server 2000 may be implemented to select, as a valid image, image data in which a region where the target participant is located has a relatively small amount of distortion in consideration of the lens distortion parameter.

Figure 27:
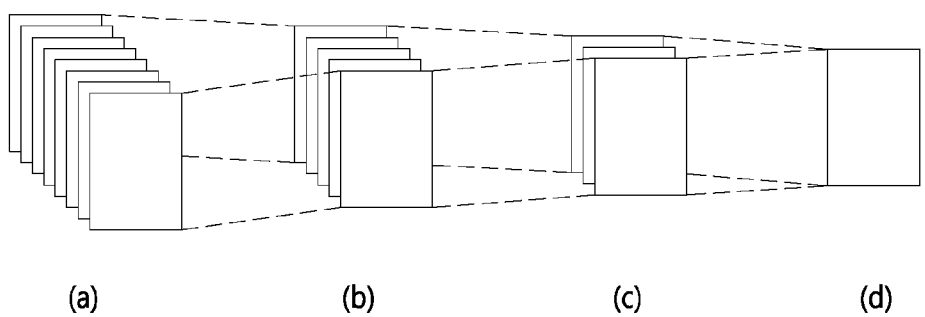
FIG. 27 is a diagram illustrating an exemplary process of selecting a valid image according to an embodiment of the present disclosure.

The following description will refer to FIG. 27. FIG. 27 is a diagram illustrating an exemplary process of the player tracking server 2000 selecting a valid image according to an embodiment of the present disclosure.

FIG. 27A shows a plurality of pieces of image data acquired from the plurality of image capture devices 301, 302, 303, and 304. In this case, the plurality of pieces of image data of FIG. 27A may be pieces of image data acquired at the same time point. The plurality of pieces of image data of FIG. 27A may include image data including a target sport participant whose location is to be determined and image data not including the target sport participant.

FIG. 27B shows at least one candidate image in which the target sport participant is detected. Specifically, the player tracking server 2000 may detect a target sport participant in each of the plurality of pieces of image data of FIG. 27A and may select image data in which the target sport participant is detected as a candidate image.

FIG. 27C shows at least one or more valid images. Specifically, the valid images may be images in which an occlusion event related to the target sport participant is not detected among the candidate images of FIG. 27B.

When the valid image includes a plurality of valid images as shown in FIG. 27C, the player tracking server 2000 may determine the location of the target sport participant in consideration of the location of the target sport participant acquired from each of the valid images. For example, the player tracking server 2000 may determine the location of the target sport participant by averaging the locations of the target sport participant acquired from the valid images.

As another example, when the valid image includes a plurality of valid images as shown in FIG. 27C, the player tracking server 2000 may determine the location of the target sport participant in further consideration of arrangement information, lens distortion parameters, or the like of the image capture devices.

FIG. 27D shows an example of at least a single image selected by the player tracking server 2000 in consideration of arrangement information, lens distortion parameters, or the like of the image capture devices.

The player tracking system 100 according to an embodiment of the present disclosure may determine the location of the target sport participant on the basis of a valid image. Specifically, the player tracking server 2000 according to an embodiment of the present disclosure may determine a location on the basis of pixel data (a pixel location) corresponding to a target sport participant of a selected valid image.

In an embodiment, when the selected valid image includes a plurality of valid images, the player tracking server 2000 may determine the location of the target sport participant in consideration of the locations of the target sport participant acquired from the plurality of valid images.

Specifically, the valid image may include a first valid image and a second valid image. In this case, the player tracking server 2000 may acquire a first location of the target sport participant on the basis of a pixel location corresponding to the target sport participant in the first valid image. Also, the player tracking server 2000 may acquire a second location of the target sport participant on the basis of a pixel location corresponding to the target sport participant in the second valid image.

Finally, the player tracking server 2000 may determine the location of the target sport participant on the basis of both of the first location and the second location.

As an example, the player tracking server 2000 may determine the location of the target sport participant by averaging the first location and the second location.

In another embodiment, when the selected valid image includes a plurality of valid images, the player tracking server 2000 may determine the location of the target sport participant in consideration of the location of the target sport participant and the location of the image capture device that captures the valid image. To this end, the player tracking server 2000 may be provided to select a single image from valid images in consideration of conditions related to the location of the target sport participant and the location of the image capture device that captures the valid image. In this case, the player tracking server 2000 may determine the location of the target sport participant on the basis of the single image.

For example, it is likely that the location of the target sport participant acquired from the valid image is relatively accurate when the location of the target sport participant and the location of the image capture device that captures the valid image are relatively close to each other. On the other hand, it is unlikely that the location of the target sport participant acquired from the valid image is relatively accurate when the location of the target sport participant and the location of the image capture device that captures the valid image are relatively far from each other.

Therefore, when the selected valid image includes a plurality of valid images, the player tracking server 2000 may determine the location of the target sport participant in additional consideration of the conditions related to the location of the target sport participant and the location of the image capture device that captures the valid image.

In another embodiment, when the selected valid image includes a plurality of valid images, the player tracking server 2000 may determine the location of the target sport participant in consideration of a lens distortion parameter of the image capture device that captures the valid image. To this end, the player tracking server 2000 may be provided to select a single image from valid images in consideration of conditions related to the lens distortion parameter of the image capture device that captures the valid image. In this case, the player tracking server 2000 may determine the location of the target sport participant on the basis of the single image.

For example, with regard to the lens distortion parameter of the image capture device that captures the valid image, when the target sport participant is located in a region of the valid image where lens distortion is relatively large (e.g., in an edge portion of the valid image), the location acquired from the target sport participant may have low accuracy.

On the other hand, with regard to the lens distortion parameter of the image capture device that captures the valid image, when the target sport participant is located in a region of the valid image where lens distortion is relatively small (e.g., in a center portion of the valid image), the location acquired from the target sport participant may have high accuracy.

Therefore, when the selected valid image includes a plurality of valid images, the player tracking server 2000 may determine the location of the target sport participant in additional consideration of conditions related to the lens distortion parameter of the image capture device that captures the valid image.

The player tracking server 2000 according to an embodiment of the present disclosure may determine the location of the target sport participant in consideration of whether the target sport participant hides another sport participant or is hidden by another sport participant. Preferably, the determination of the location of the target sport participant in consideration of whether the target sport participant hides or is hidden by another sport participant may be advantageously applied to a case in which there is no valid image, that is, a case in which the target sport participant is detected from a plurality of pieces of image data and an occlusion event related to the target sport participant has occurred in all candidate images. To this end, the player tracking server 2000 may be provided to select a target image from the candidate images in consideration of whether the target sport participant hides or is hidden by another sport participant. In this case, the player tracking server 2000 may determine the location of the target sport participant on the basis of the target image.

For example, when the target sport participant hides another sport participant, a pixel location corresponding to the target sport participant in the image data may be specified. Therefore, the player tracking server 2000 may select image data in which the target sport participant hides another sport participant as a target image. Also, the player tracking server 2000 may determine the location of the target sport participant on the basis of the selected target image.

On the other hand, when the target sport participant is hidden by another sport participant, it is highly likely that a pixel location corresponding to the target sport participant in the image data is not specified. Therefore, the player tracking server 2000 may be implemented such that the image data in which the target sport participant is hidden by another sport participant is not used to determine the location of the target sport participant.

However, the above description is just an example, and it is obvious that when an occlusion event related to the target sport participant occurs in all candidate images, the player's location may be determined using the positioning sensor-based location which has been described with reference to FIGS. 16 to 25.

The configuration and operation of the player tracking server 2000 according to an embodiment of the present disclosure have been described above. A player tracking method according to this embodiment will be described below. In the following description, the player tracking method according to this embodiment is performed by the above-described player tracking system 100. However, this is just for convenience of description, and thus the player tracking method according to this embodiment is not limited to the above-described player tracking system 100. That is, the player tracking method, which will be described below, does not necessarily have to be performed only by the player tracking system 100 but may be performed by another system or device having a function similar to that of the above-described player tracking system 100.

Figure 28:
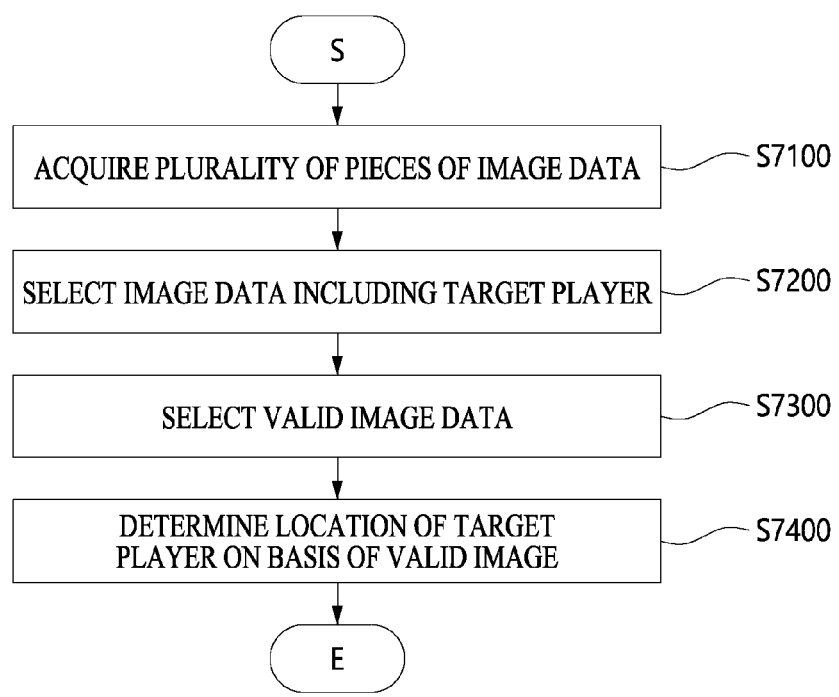
FIG. 28 is a flowchart illustrating a player tracking system using a plurality of image capture devices according to an embodiment of the present disclosure.

The following description will refer to FIG. 28. FIG. 28 is a flowchart of a player tracking method according to an embodiment of the present disclosure.

Referring to FIG. 28, the player tracking method according to an embodiment of the present disclosure may include acquiring a plurality of pieces of image data (S7100), selecting a piece of image data including a target sport participant (S7200), selecting a valid image (S7300), and determining a location of the target sport participant on the basis of the valid image (S7400).

The above-described operations will be described in detail below.

The player tracking server 2000 may acquire a plurality of pieces of image data (S7100). Specifically, the player tracking server 2000 may acquire a plurality of pieces of image data from the plurality of image capture devices 301, 302, 303, and 304 through the communication module 1100.

In operation S7100, the player tracking server 2000 may acquire a plurality of pieces of image data captured by the plurality of image capture devices 301, 302, 303, and 304. In this case, the player tracking server 2000 may also acquire arrangement information related to locations and orientations of the plurality of image capture devices 301, 302, 303, and 304, identifiers of the image capture devices, lens distortion parameters, and location-related data (positioning sensor data or pixel data of image data) of a sport participant.

The plurality of pieces of image data acquired in operation S7100 may include a plurality of sport participants. The plurality of pieces of image data may or may not include a target sport participant whose location is to be determined.

Therefore, the player tracking server 2000 may detect the target sport participant from the plurality of pieces of image data and select image data including the target sport participant (S7200). Specifically, the player tracking server 2000 may be provided to perform an operation of detecting the target sport participant included in the plurality of pieces of image data. In this case, the player tracking server 2000 may be implemented to select a candidate image according to a result of detecting the target sport participant.

For example, the player tracking server 2000 may select, as a candidate image, image data in which the target sport participant is detected.

In this case, the candidate image in which the target sport participant is detected may include at least one candidate image.

As an example, the target sport participant may be detected in all of the plurality of pieces of image data. In this case, all images in which the target sport participant is detected may be selected as candidate images.

However, the candidate images selected according to whether the target sport participant is detected may include images that are not suitable as a basis for determining the location of the target sport participant.

Therefore, the player tracking server 2000 may select a valid image from the candidate images (S7300). Here, the valid image may be used in the sense of encompassing any image suitable for determining the location of the target sport participant.

Specifically, the player tracking server 2000 may be provided to select a valid image from among the candidate images in consideration of whether an occlusion event related to the target sport participant is detected.

As an example, the player tracking server 2000 may detect the occlusion event or determine whether the occlusion event has occurred. Alternatively, the player tracking server 2000 may determine the severity of the occlusion event.

In particular, the player tracking server 2000 may detect an occlusion event related to the target sport participant or determine whether the occlusion event has occurred. Alternatively, the player tracking server 2000 may determine the severity of the occlusion event related to the target sport participant.

In this case, the player tracking server 2000 may select at least one valid image from the candidate images selected in operation S7200 on the basis of a result of detecting the occlusion event related to the target sport participant.

For example, the player tracking server 2000 may select, as valid images, candidate images in which the occlusion event related to the target sport participant is not detected.

On the other hand, the player tracking server 2000 may not select, as valid images, candidate images in which the occlusion event related to the target sport participant is detected. However, even though the occlusion event related to the target sport participant is detected, the player tracking server 2000 may be provided to select a corresponding candidate image as a valid image when it is determined that the occlusion event is not severe.

In operation S7300, in consideration of additional conditions, a single image may be selected from valid images selected in consideration of a result of detecting the occlusion event.

Specifically, when a plurality of valid images are selected in consideration of the result of detecting the occlusion event related to the target sport participant, a single image may be selected from the valid images in additional consideration of a condition related to the location of the target sport participant and the location of the image capture device that captures the valid image or conditions related to a lens distortion parameter of the image capture device that captures the valid image.

As an example, the accuracy of the location of the target sport participant may be different depending on the size or sharpness of the target sport participant included in the valid image. When the target sport participant included in the valid image has a large size or a high resolution, the location of the target sport participant determined from the corresponding valid image may be relatively accurate.

In this case, the size or resolution of the target sport participant included in the valid image may depend on the location of the target sport participant and a location of the image capture device that captures the valid image. For example, when the location of the target sport participant and the location of the image capture device that captures the valid image are relatively close to each other, the captured target sport participant may be large and clear. On the other hand, when the location of the target sport participant and the location of the image capture device that captures the valid image are relatively far from each other, the captured target sport participant may be relatively small and unclear.

Therefore, according to an embodiment, in operation S7300, the player tracking server 2000 may be implemented to select a single image from among the valid images in consideration of a condition related to the location of the target sport participant and the location of the image capture device that captures the valid image.

As another example, the accuracy of the location of the target sport participant may be different depending on the location of the target sport participant in the valid image and the degree of distortion for each region of the valid image.

For example, when the target sport participant is located in a region with less distortion of the valid image, the location of the target sport participant determined from the corresponding valid image may be relatively accurate.

As another example, when the target sport participant is located in the center of the valid image where the degree of distortion is relatively low, the accuracy of the location of the target sport participant determined from the corresponding valid image may be relatively high. On the other hand, when the target sport participant is located at an edge of the valid image where the degree of distortion is relatively high, the accuracy of the location of the target sport participant determined from the corresponding valid image may be relatively low.

In this case, the degree of distortion for each region of the valid image may depend on a lens distortion parameter. Therefore, according to an embodiment, in operation S7300, the player tracking server 2000 may be implemented to select a single image from among the valid images in consideration of a condition related to a lens distortion parameter of the image capture device that captures the valid image.

In operation S7300, a target image may be selected from the candidate images selected in operation S7200 in consideration of the type of the occlusion event related to the target sport participant. Preferably, the selection of the target image in consideration of the type of the occlusion event related to the target sport participant may be advantageously applied to a case in which the occlusion event related to the target sport participant is detected in all of the candidate images.

The type of occlusion event may include a first type in which the target sport participant hides another sport participant and a second type in which the target sport participant is hidden by another sport participant.

In the case of the first type, it may be relatively easy to specify a location of a pixel corresponding to the target sport participant. On the other hand, in the case of the second type, it may be relatively difficult to specify a location of a pixel corresponding to the target sport participant because the target sport participant is hidden by another sport participant.

Therefore, the player tracking server 2000 may be provided to select a candidate image corresponding to the first type as a target image. On the other hand, the player tracking server 2000 may be provided not to select a candidate image corresponding to the second type as a target image.

The player tracking server 2000 may determine the location of the target sport participant on the basis of the selected target image (S7400).

Specifically, the player tracking server 2000 may be provided to determine the location of the target sport participant in consideration of a pixel location corresponding to the target sport participant in the valid image, target image, or single image (hereinafter referred to as the valid image or the like) selected in operation S7300.

As an example, when the valid image or the like selected in operation S7300 includes a single valid image, the location of the target sport participant may be determined in consideration of a pixel location corresponding to the target sport participant in the selected image.

As another example, when the valid image or the like selected in operation S7300 includes a plurality of valid images, the location of the target sport participant may be determined in consideration of all or some pixel locations corresponding to the target sport participant in the plurality of valid images or the like. For example, the location of the target sport participant may be determined by averaging the pixel locations acquired from the plurality of valid images or the like.

Alternatively, when the valid image or the like selected in operation S7300 includes a plurality of valid images, the location of the target sport participant may be determined in further consideration of a condition related to the location of the target participant and a location of a camera that captures the at least one valid image or a condition related to a lens distortion parameter. For example, the location of the target sport participant may be determined in consideration of a pixel location corresponding to the target sport participant in a single image selected from the valid image or the like in consideration of a condition related to the location of the target participant and the location of the camera that captures the at least one valid image or a condition related to the lens distortion parameter.

As described above, although the description was focused on determining the location of the target sport participant on the basis of locations acquired from image data, it is obvious that the details of FIGS. 16 to 27 in which the location of the sport participant is determined in consideration of locations acquired from positioning sensor data may be applied.

The player tracking server 2000 according to an embodiment of the present disclosure will be described below.

According to an embodiment of the present disclosure, the player tracking server 2000 may acquire image data from the plurality of image capture devices 301, 302, 303, and 304 in order to determine a location of a sport participant. Also, the player tracking server 2000 may acquire positioning sensor data from the positioning sensor device 200 in order to determine the location of the sport participant. Also, the player tracking server 2000 may compute an image-based location from the acquired image data and compute a positioning sensor-based location from the acquired positioning sensor data. Also, the player tracking server 2000 may generate a virtual playfield or generate a matching table on the basis of the computed image-based location and positioning sensor-based location. However, according to a preferred embodiment, the player tracking server 2000 may generate the virtual playfield or generate the matching table on the basis of the positioning sensor-based location.

The details described with reference to FIG. 4 may be equally applied to the player tracking server 2000 according to an embodiment of the present disclosure. That is, the player tracking server 2000 may include a communication module 1100, a memory 1200, and a controller 1300. In particular, the details described with reference to FIG. 4 may be equally applied to the communication module 1100, the memory 1200, and the controller 1300, and thus a detailed description thereof will be omitted. Therefore, the following description will focus on details added to the player tracking server 2000.

Some operations performed by an example of the player tracking system 100 in association with the player tracking method will be described in detail below.

The player tracking system 100 according to this embodiment may acquire a plurality of pieces of image data from a plurality of image capture devices. Specifically, the player tracking server 2000 may acquire a plurality of pieces of image data captured by a plurality of image capture devices. Also, the player tracking system 100 may acquire arrangement information related to the locations and orientations of the plurality of image capture devices from the plurality of image capture devices. Also, the player tracking system 100 may acquire positioning sensor data from the positioning sensor device 200. Also, the player tracking system 100 may generate a virtual playfield and generate a matching table on the basis of positioning sensor data and arrangement information related to the image capture devices.

The player tracking server 2000 according to an embodiment of the present disclosure may determine the validity of the location of the sport participant acquired from the image data, which has been described above with reference to FIGS. 6 to 11.

For example, the player tracking server 2000 may detect an occlusion event in a plurality of pieces of image data acquired from the plurality of image capture devices 301, 302, 303, and 304 or determine whether an occlusion event has occurred.

Also, the player tracking server 2000 may determine the severity of the occlusion event in the plurality of pieces of image data acquired from the plurality of image capture devices 301, 302, 303, and 304.

The player tracking system 100 according to this embodiment may generate a virtual playfield. Specifically, the player tracking server 2000 may be provided to generate a virtual playfield on the basis of positioning sensor data and arrangement information related to the image capture devices. Specifically, the player tracking server 2000 may generate virtual points corresponding to the image capture devices on the basis of the arrangement information related to the locations of the image capture devices.

Also, the player tracking server 2000 may generate a plurality of moving points corresponding to a plurality of sport participants on the basis of positioning sensor data of the plurality of sport participants.

The player tracking system 100 according to this embodiment may be implemented to predict an occlusion event (or the severity of an occlusion event) on the basis of the generated virtual playfield. Specifically, the player tracking server 2000 may be implemented to predict an occlusion event between sport participants on the basis of arrangement information related to the orientations of the image capture devices and a location relationship between the plurality of moving points in the virtual playfield.

The player tracking system 100 according to this embodiment may be implemented to generate a matching table between the plurality of sport participants and the plurality of image capture devices on the basis of the generated virtual playfield.

Specifically, the player tracking server 2000 may compute a relationship between the plurality of sport participants and the plurality of image capture devices on the basis of relative locations between a plurality of moving points corresponding to the sport participants and a plurality of points corresponding to the image capture devices in the generated virtual playfield. In this case, the player tracking server 2000 may be implemented to generate a matching table between the sport participants and the plurality of image capture devices on the basis of the relationship and a result of predicting the occlusion event.

Figure 29:
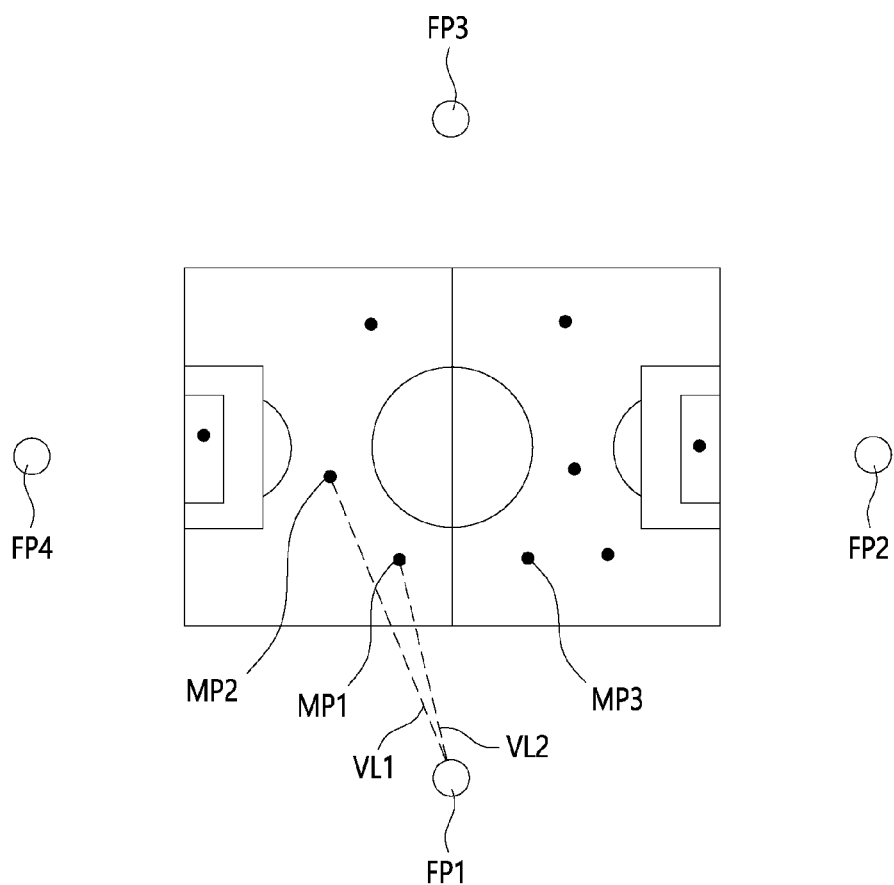
FIG. 29 is an exemplary diagram showing a virtual playfield according to an embodiment of the present disclosure.

The following description will refer to FIG. 29. FIG. 29 is an exemplary diagram showing a virtual playfield according to an embodiment of the present disclosure.

The player tracking server 2000 may generate a virtual playfield on the basis of location information of a plurality of sport participants and arrangement information of image capture devices.

The arrangement information of the image capture devices may include information regarding locations, lines of sight, and orientations of the plurality of image capture devices 301, 302, 303, and 304.

The location information of the plurality of sport participants may be acquired from positioning sensor data. Alternatively, the location information of the plurality of sport participants may be acquired from image data.

The player tracking server 2000 may generate a plurality of points corresponding to the plurality of image capture devices in a virtual playfield coordinate system in consideration of the arrangement information of the image capture devices.

In this case, the locations of the image capture devices may be changed or fixed.

When the locations of the image capture devices are changed, the player tracking server 2000 may generate a plurality of moving points corresponding to the plurality of image capture devices in the virtual playfield coordinate system in consideration of a change in the location information of the plurality of image capture devices according to the progress of a sport game.

When the locations of the image capture devices are fixed, the player tracking server 2000 may generate a plurality of fixed points FP1, FP2, FP3, and FP4 corresponding to the plurality of image capture devices in the virtual playfield coordinate system as shown in FIG. 29.

Also, the player tracking server 2000 may generate a plurality of points MP1, MP2, and MP3 corresponding to the plurality of sport participants in a virtual playfield coordinate system in consideration of the location information of the plurality of sport participants.

Also, the player tracking server 2000 may generate a plurality of points corresponding to the plurality of sport participants in the virtual playfield coordinate system in consideration of a change in the location information of the plurality of sport participants according to the progress of a sport game. That is, the plurality of points corresponding to the plurality of sport participants may be moving points MP1, MP2, and MP3.

Also, the player tracking server 2000 may compute a relationship between the plurality of sport participants and the plurality of image capture devices 301, 302, 303, and 304 on the basis of the generated virtual playfield.

Specifically, the player tracking server 2000 may compute a relationship between the plurality of sport participants and the plurality of image capture devices 301, 302, 303, and 304 on the basis of relative locations between moving points MP1, MP2, and MP3 of the virtual playfield corresponding to the plurality of sport participants and points FP1, FP2, FP3, and FP4 of the virtual playfield corresponding to the plurality of image capture devices 301, 302, 303, and 304.

Also, the player tracking server 2000 may predict whether an occlusion event has occurred between the plurality of sport participants on the basis of the relationship between the plurality of sport participants and the plurality of image capture devices 301, 302, 303, and 304.

For example, a plurality of virtual lines VL may be generated in the virtual playfield from the points FP1, FP2, FP3, and FP4 corresponding to the plurality of image capture devices 301, 302, 303, and 304 to the plurality of moving points MP1, MP2, and MP3 corresponding to the plurality of sport participants.

In this case, the player tracking server 2000 may predict whether an occlusion event has occurred between sport participants in consideration of at least one of the locations of the points FP1, FP2, FP3, and FP4 corresponding to the plurality of image capture devices 301, 302, 303, and 304, the locations of the plurality of moving points MP1, MP2, and MP3 corresponding to the plurality of sport participants, and angles between the plurality of virtual lines VL1 and VL2.

For example, referring to FIG. 29, the first virtual line VL1 extending from the first fixed point FP1 to the first moving point MP1 and the second virtual line VL2 extending from the first fixed point FP1 to the second moving point MP2 may be generated.

In this case, when the first virtual line VL1 and the second virtual line VL2 overlap or when the angle between the first virtual line VL1 and the second virtual line VL2 is less than a predetermined angle, the player tracking server 2000 may determine or predict that an occlusion event is likely to have occurred between a first sport participant corresponding to the first moving point MP1 and a second sport participant corresponding to the second moving point MP2.

In this case, additionally, the player tracking server 2000 may determine or predict that an occlusion event is likely to have occurred between the first sport participant corresponding to the first moving point MP1 and the second sport participant corresponding to the second moving point MP2 from the first image capture device 301 corresponding to the first fixed point FP1.

Also, the player tracking server 2000 may predict whether an occlusion event occurs between sport participants in further consideration of a difference in location between the first moving point MP1 and the second moving point MP2.

For example, referring to FIG. 29, even when the angle of the first virtual line VL1 is the same as the angle of the second virtual line VL2, whether an occlusion has occurred between the first sport participant corresponding to the first moving point MP1 and the second sport participant corresponding to the second moving point MP2 with respect to the first fixed point FP1 may differ depending on the difference in location between the first moving point MP1 and the second moving point MP2.

Therefore, the player tracking server 2000 may predict whether an occlusion event has occurred between sport participants in further consideration of the difference in location between the moving points corresponding to the plurality of sport participants.

Also, the player tracking server 2000 may predict whether an occlusion event has occurred between sport participants in consideration of the points of the virtual playfield corresponding to the plurality of image capture devices, the moving points of the virtual playfield corresponding to the plurality of sport participants, and information regarding the lines of sight of the plurality of image capture devices.

For example, a virtual line corresponding to a line of sight may be generated in consideration of a line of sight of the first image capture device 301 corresponding to the first fixed point FP1. In this case, when a first moving point and a second moving point are substantially located on the virtual line corresponding to the line of sight, the player tracking server 2000 may determine that an occlusion event has occurred between a first sport participant corresponding to the first moving point and a second sport participant corresponding to the second moving point.

Also, the player tracking server 2000 may predict whether an occlusion event has occurred between the plurality of sport participants later in consideration of orientation information of the plurality of image capture devices and velocity data (or acceleration data) of the plurality of sport participants.

For example, referring to FIG. 29, velocity data (or acceleration data) of the first sport participant and the third sport participant may be acquired by any suitable method. Also, orientation information of the first image capture device may be acquired. In this case, the player tracking server 2000 may predict that the first moving point MP1 corresponding to the first sport participant moves toward the third moving point MP3 corresponding to the third sport participant and that the third moving point MP3 corresponding to the third sport participant moves toward the first moving point MP1 corresponding to the first sport participant on the basis of the velocity data (or the acceleration data).

Also, the player tracking server 2000 may predict the orientation of the first fixed point FP1 corresponding to the first image capture device on the basis of the orientation information.

Accordingly, the player tracking server 2000 may predict an occlusion between the first sport participant corresponding to the first moving point MP1 and the second port participant corresponding to the second moving point MP2 with respect to the first image capture device corresponding to the first fixed point FP1 later.

Also, the player tracking server 2000 may be implemented to generate a matching table between a plurality of sport participants and a plurality of image capture devices on the basis of a relationship between the plurality of sport participants and the plurality of image capture devices computed based on relative locations between a plurality of moving points corresponding to the plurality of sport participants and a plurality of points corresponding to the plurality of image capture devices.

The player tracking server 2000 may generate a matching table between the plurality of sport participants and the plurality of image capture devices on the basis of the prediction of the occlusion.

As an example, virtual lines may extend from the plurality of fixed points FP1, FP2, FP3, and FP4 corresponding to the plurality of image capture devices 301, 302, 303, and 304 to the plurality of moving points (including MP1, MP2, and MP3) corresponding to the plurality of sport participants, and a table for a result of predicting the occlusion event based on angles between the virtual lines may be generated.

For example, referring to FIG. 29, it may be predicted from the first image capture device 301 corresponding to the first fixed point FP1 that an occlusion event has occurred between the first sport participant corresponding to the first moving point MP1 and the second sport participant corresponding to the second moving point MP2.

On the other hand, it may be predicted from the second, third, and fourth image capture devices 302, 303, and 304 corresponding to the second, third, and fourth fixed points that no occlusion event has occurred between the first sport participant corresponding to the first moving point MP1 and the second sport participant corresponding to the second moving point MP2.

In this case, the player tracking server 2000 may generate a matching table on the basis of whether an occlusion is predicted based on the locations of the plurality of fixed points FP1, FP2, FP3, and FP4 corresponding to the image capture devices 301, 302, 303, and 304, the locations of the moving points corresponding to the plurality of sport participants, and angles between the plurality of virtual lines.

Similarly, the player tracking server 2000 may generate a matching table on the basis of whether an occlusion is predicted according to the difference in location between the plurality of moving points corresponding to the plurality of sport participants.

Similarly, the player tracking server 2000 may generate a matching table on the basis of whether an occlusion is predicted according to the orientation information of the plurality of image capture devices and the velocity data (or acceleration data) of the plurality of sport participants.

The matching table generated as described above may be used to select and continuously monitor an image capture device most suitable for tracking the target sport participant.

Also, the matching table may be used to select an image capture device most suitable for capturing the target sport participant in association with broadcasting.

Also, the matching table may be used to select an image capture device most suitable for generating an individual highlight of the target sport participant.

The configuration and operation of the player tracking server 2000 according to an embodiment of the present disclosure have been described above. A player tracking method according to this embodiment will be described below. In the following description, the player tracking method according to this embodiment is performed by the above-described player tracking system 100. However, this is just for convenience of description, and thus the player tracking method according to this embodiment is not limited to the above-described player tracking system 100. That is, the player tracking method, which will be described below, does not necessarily have to be performed only by the player tracking system 100 but may be performed by another system or device having a function similar to that of the above-described player tracking system 100.

Figure 30:
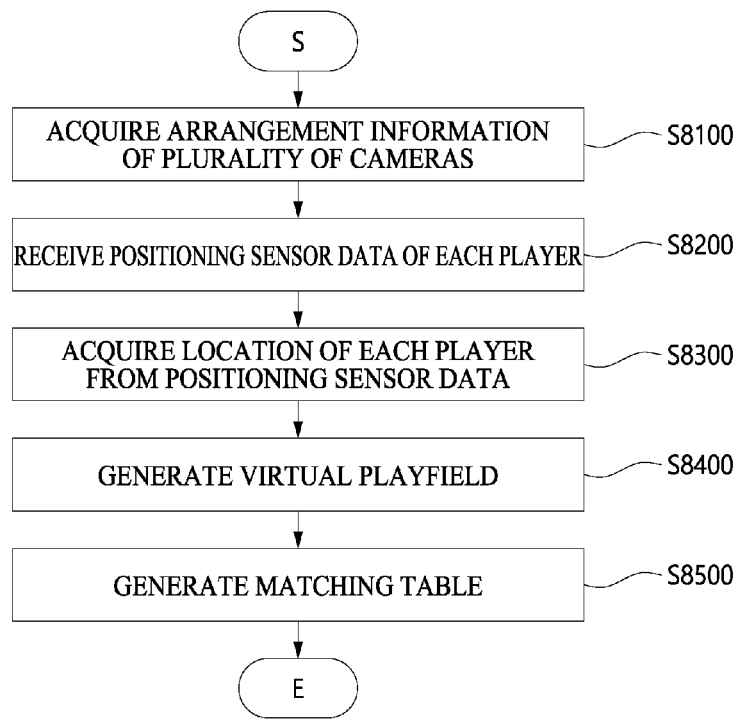
FIG. 30 is a flowchart illustrating a player tracking method using a plurality of image capture devices according to an embodiment of the present disclosure.

The following description will refer to FIG. 30. FIG. 30 is a flowchart illustrating a player tracking method using a plurality of image capture devices according to an embodiment of the present disclosure.

Referring to FIG. 30, a player tracking method using a plurality of image capture devices according to an embodiment of the present disclosure may include acquiring arrangement information of the plurality of image capture devices (S8100), receiving positioning sensor data of the plurality of sport participants (S8200), acquiring locations of the plurality of sport participants from the positioning sensor data (S8300), generating a virtual playfield (S8400), and generating a matching table (S8500).

The above-described operations will be described in detail below.

The player tracking server 2000 may acquire the arrangement information of the plurality of image capture devices (S8100). Specifically, in operation S8100, the player tracking server 2000 may acquire a plurality of pieces of image data captured by the plurality of image capture devices 301, 302, 303, and 304 and arrangement information related to the location and orientations of the plurality of image capture devices 301, 302, 303, and 304 through the communication module 1100.

The player tracking server 2000 may receive the positioning sensor data of the plurality of sport participants (S8200). Specifically, the player tracking server 2000 may acquire a plurality of pieces of image data from positioning sensor devices 200 worn by the plurality of sport participants through the communication module 1100.

In operation S8200, the player tracking server 2000 may acquire positioning sensor data transmitted from the positioning sensor devices 200 worn by the plurality of sport participants. The positioning sensor data may include sport participant-related location information, an identifier of a sport participant, and the reliability of a sensor signal.

The player tracking server 2000 may compute or acquire positioning sensor-based locations of the plurality of sport participants (S8300). Specifically, the player tracking server 2000 may acquire a plurality of pieces of positioning sensor data from positioning sensor devices 200 worn by the plurality of sport participants through the communication module 1100. Specifically, the player tracking server 2000 may acquire locations of the plurality of sport participants from the sport participant-related location information included in the positioning sensor data. Also, the player tracking server 2000 may acquire velocity- or acceleration-related information from the sport participant-related location information included in the positioning sensor data as well as the acquired locations.

Also, the player tracking server 2000 may generate a virtual playfield (S8400). In this case, the virtual playfield may include a plurality of points corresponding to the locations of the plurality of image capture devices and a plurality of moving points corresponding to the locations of the plurality of sport participants acquired in operation S8300.

The player tracking server 2000 may generate the plurality of points corresponding to the plurality of image capture devices on the basis of arrangement information related to the locations of the plurality of image capture devices 301, 302, 303, and 304 acquired in operation S8100.

Also, the player tracking server 2000 may generate the plurality of moving points corresponding to the plurality of sport participants on the basis of the locations of the plurality of sport participants acquired in operation S8300.

Also, the player tracking server 2000 may generate a plurality of virtual lines on the basis of the plurality of moving points corresponding to the plurality of sport participants and the arrangement information related to the orientations of the plurality of image capture devices 301, 302, 303, and 304 acquired in operation S8100.

In operation S8400, the player tracking server 2000 may be provided to compute a relationship between the plurality of sport participants and the plurality of image capture devices.

For example, the player tracking server 2000 may compute a location relationship between the plurality of moving points corresponding to the plurality of sport participants and the plurality of fixed points corresponding to the image capture devices generated in the virtual playfield.

As another example, the player tracking server 2000 may compute a location relationship between the plurality of moving points corresponding to the plurality of sport participants generated in the virtual playfield.

As another example, the player tracking server 2000 may compute a relationship such as an angle between the plurality of virtual lines generated in the virtual playfield.

Also, in operation S8400, the player tracking server 2000 may be implemented to predict whether an occlusion event has occurred between a plurality of sport participants.

As an example, the player tracking server 2000 may predict whether an occlusion event has occurred between a plurality of sport participants on the basis of relative locations between the plurality of moving points corresponding to the plurality of sport participants and the plurality of virtual lines generated in the virtual playfield.

Also, the player tracking server 2000 may determine from which image capture device an occlusion event between the plurality of sport participants has occurred.

For example, referring to FIG. 29 again, the first virtual line VL1 extending from the first fixed point FP1 to the first moving point MP1 and the second virtual line VL2 extending from the first fixed point FP1 to the second moving point MP2 may be generated.

In this case, when the first virtual line VL1 and the second virtual line VL2 overlap or when the angle between the first virtual line VL1 and the second virtual line VL2 is less than a predetermined angle, the player tracking server 2000 may determine or predict that an occlusion event is likely to have occurred between a first sport participant corresponding to the first moving point MP1 and a second sport participant corresponding to the second moving point MP2.

In this case, additionally, the player tracking server 2000 may determine or predict that an occlusion event is likely to have occurred between the first sport participant corresponding to the first moving point MP1 and the second sport participant corresponding to the second moving point MP2 from the first image capture device 301 corresponding to the first fixed point FP1.

As another example, the player tracking server 2000 may predict whether an occlusion event has occurred between a plurality of sport participants on the basis of a difference in location between the plurality of moving points corresponding to the plurality of sport participants.

For example, referring to FIG. 29, even when the angle of the first virtual line VL1 is the same as the angle of the second virtual line VL2, whether an occlusion has occurred between the first sport participant corresponding to the first moving point MP1 and the second sport participant corresponding to the second moving point MP2 with respect to the first fixed point FP1 may differ depending on the difference in location between the first moving point MP1 and the second moving point MP2.

Therefore, the player tracking server 2000 may predict whether an occlusion event has occurred between sport participants in further consideration of the difference in location between the moving points corresponding to the plurality of sport participants.

The player tracking server 2000 may generate a matching table (S8500).

The player tracking server 2000 may generate a matching table between the plurality of sport participants and the plurality of image capture devices on the basis of a result of predicting the occlusion between the plurality of sport participants, the relationship between the plurality of sport participants, and the plurality of image capture devices computed in operation S8400.

As an example, virtual lines may extend from the plurality of fixed points FP1, FP2, FP3, and FP4 corresponding to the plurality of image capture devices 301, 302, 303, and 304 to the plurality of moving points (including MP1, MP2, and MP3) corresponding to the plurality of sport participants, and a table for a result of predicting the occlusion event based on angles between the virtual lines may be generated.

As another example, the player tracking server 2000 may generate a matching table on the basis of whether an occlusion is predicted according to the difference in location between the plurality of moving points corresponding to the plurality of sport participants.

As another example, the player tracking server 2000 may generate a matching table on the basis of whether an occlusion is predicted according to the orientation information of the plurality of image capture devices and the velocity data (or acceleration data) of the plurality of sport participants.

However, the above description is just an example, and the matching table may be generated by any suitable method.

The above-described player tracking method, player tracking device, and player tracking system using a plurality of image capture devices according to an embodiment of the present disclosure can significantly reduce the possibility of an error in computing the location of a sport participant due to an occlusion event compared to a case in which a single image capture device is used.

Figure 31:
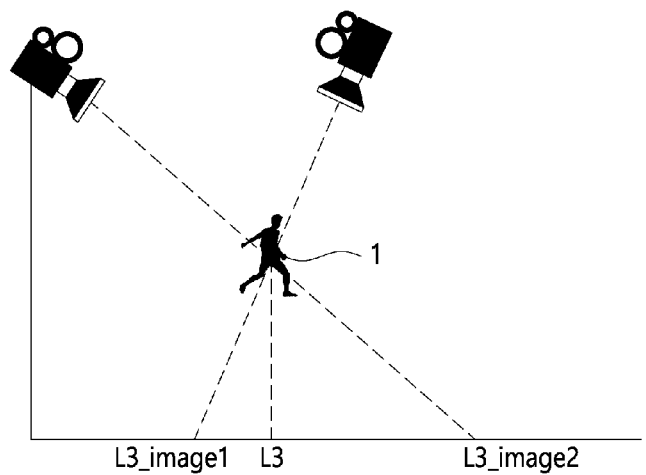
FIG. 31 is a schematic diagram illustrating a method of computing a sport participant's location through a player tracking method using a plurality of image capture devices according to an embodiment of the present disclosure.

The following description will refer to FIGS. 9 and 31. FIG. 31 is a schematic diagram illustrating a method of computing a sport participant's location through a player tracking method using a plurality of image capture devices according to an embodiment of the present disclosure.

Referring to FIG. 9B, when a single image capture device is used, an error due to a vertical movement of a sport participant 1 may occur between an actual location L2 and a location L2_image acquired from image data.

On the other hand, referring to FIG. 31, when a plurality of image capture devices are used, the error due to the vertical movement of the sport participant 1 between the actual location L3 and the location L3_image1 or L3_image2 acquired from the image data may be corrected.

For example, by considering the height of the plurality of image capture devices and the angles of the plurality of image capture devices with respect to the ground, a correction parameter for the location L3_image1 or L3_image2 acquired from the image data may be computed. By applying the computed correction parameter to the location L3_image1 or L3_image2 acquired from the image data, the actual location L3 of the sport participant 1 can be easily computed.

Also, in the case of using only a single image capture device, when an occlusion event occurs in image data acquired from the corresponding image capture device, there is a lack of an alternative method for acquiring an accurate location using only image data.

On the other hand, in the case of using a plurality of image capture devices, even when an occlusion event occurs in first image data, it is possible to accurately compute the location of a sport participant using second image data in which no occlusion event is detected.

Also, in the case of using the plurality of image capture devices, a panoramic view image or an image with improved quality may be generated by matching a plurality of pieces of image data acquired from a plurality of image capture devices.

In this case, a panoramic view image or an image with improved quality may be generated by matching a plurality of pieces of image data on the basis of references such as a reference point, a reference line, and a reference surface of a region where the plurality of pieces of image data overlap.

The player tracking method, the player tracking device, and the player tracking system according to the present disclosure may be used to analyze a sport participant. Specifically, the present disclosure may be applied to all sport analysis fields, such as the analysis of the movement, velocity, and acceleration of a sport participant and tactical analysis, which require the location of a sport player to be accurately computed.

Also, the above description has focused on soccer among sports, but this is just an example. The present disclosure may be applied to all sports that require the location of a sport player to be computed.

Also, the player tracking method, the player tracking device, and the player tracking system according to the present disclosure are capable of continuously tracking a sport player, and thus may be used even in various fields such as broadcasting related to video, video content related to highlight generation, etc.

According to an embodiment of the present disclosure, by calculating a player's location by fusion of image data and positioning sensor data, it is possible to precisely track the player's location.

According to an embodiment of the present disclosure, by choosing image data optimized for a location of a player to be tracked using a plurality of cameras and calculating the location of the corresponding player from the image data, it is possible to precisely track the player's location.

The features, structures, and effects described in the above embodiments are incorporated into at least one embodiment of the present disclosure but are not necessarily limited to only one embodiment. Moreover, features, structures, and effects exemplified in one embodiment can easily be combined and modified for another embodiment and then be carried out by those skilled in the art. Therefore, these combinations and modifications should be construed as falling within the scope of the present disclosure.

While the present disclosure has been described with reference to embodiments, these are just examples and do not limit the present disclosure. It will be understood by those skilled in the art that various modifications and applications may be made therein without departing from the essential characteristics of the embodiments. That is, elements described in the embodiments above in detail may be modified. Furthermore, differences associated with such modifications and applications should be construed as being included in the scope of the present disclosure defined by the appended claims.

What is claimed is:

1. A multi-modal tracking method, the method comprising:
   receiving, from a positioning sensor being disposed at a sports participant, a sensor signal;
   obtaining a sensor-based location of the sports participant based on the sensor signal;
   obtaining a first credibility information related to a credibility of the sensor-based location;
   receiving a sports image captured at a camera disposed peripheral to a playfield, the sports image including the sports participant in the playfield;
   obtaining an image-based location of the sports participant based on a pixel-location of the sports participant in the sport image;
   obtaining a second credibility information related to a credibility of the image-based location, wherein the credibility of the image-based location is related to at least one of: an occlusion related to the sports participant, a vertical movement related to the sports participant and a change of the image-based location from a previous image-based location;
   calculating a weight value based on the first credibility information and the second credibility information, the weight value includes a sensor-based weight value and an image-based weight value; and
   calculating a location of the sports participant, wherein the location of the sports participant is derived from the sensor-based location according to the sensor-based weight value and the image-based location according to the image-based weight value.

2. The method according to claim 1,
   wherein the credibility of the sensor-based location is related to at least one of: a change of the sensor-based location from a previous sensor-based location, and a credibility information related to the sensor signal which is included in the sensor signal.

3. The method according to claim 1,
   wherein the vertical movement related to the sports participant is obtained based on a movement of the sport participant in a vertical direction relative to the reference plane having a same height with the playfield obtained from an inertial sensor disposed at the sport participant.

4. The method according to claim 1,
   wherein the credibility of the sensor-based location and the credibility of the image-based location are related to a disparity index between the sensor-based location and the image-based location, and wherein the disparity index is obtained from a difference of the sensor-based location and the image-based location.

5. A multi-modal tracking method, the method comprising:
   receiving, from a positioning sensor being disposed at a sports participant, a sensor signal;
   obtaining a sensor-based location of the sports participant based on the sensor signal;
   preparing a credibility map corresponding to a playfield, wherein the credibility map comprises a first plurality of regions which are assigned first credibility information, and the first credibility information is related to a credibility of the sensor-based location;
   receiving a sports image captured by a camera disposed peripheral to the playfield, the sports image including the sports participant in the playfield;
   obtaining an image-based location of the sports participant based on a pixel-location of the sports participant in the sport image;
   determining a specific region being occupied by the sports participant based on the sensor-based location;
   determining a first weight value and a second weight value according to the credibility information of a specific region among the first plurality of regions in the credibility map; and
   determining a location of the sports participant based on a weighted average of the sensor-based location and the image-based location according to the first weight value and the second weight value.

6. The method according to claim 5,
wherein the first credibility information related to the sensor-based location is related to at least one of: a change of the sensor-based location from a previous sensor-based location, and a credibility information related to the sensor signal which is included in the sensor signal.

7. The method according to claim 5,
wherein the credibility map includes a second plurality of the regions which are assigned a second credibility information related to a credibility of the image-based location.

8. The method according to claim 7,
wherein the second credibility information is related to at least one of: an occlusion related the sports participant, a vertical movement related to the sports participant and a change of the image-based location from a previous image-based location.

9. The method according to claim 8,
wherein the first weight value and the second weight value are determined according to the second credibility information of the specific region.

* * * * *